(12) United States Patent
Nitsan et al.

(10) Patent No.: US 9,333,287 B2
(45) Date of Patent: May 10, 2016

(54) BODY PASSAGE CLEANSING DEVICE

(75) Inventors: David Nitsan, Tel-Aviv (IL); Shay Dubi, Tel-Aviv (IL); Nadav Ben-Da'At, Karkur (IL); Anat Kerem-Angel, Tel-Aviv (IL); Jacek Krzyzanowski, Etobicoke (CA)

(73) Assignee: Jet Prep Ltd., Yoqne'am (IL)

( * ) Notice: Subject to any disclaimer, the term of this patent is extended or adjusted under 35 U.S.C. 154(b) by 505 days.

(21) Appl. No.: 12/923,796

(22) Filed: Oct. 7, 2010

(65) Prior Publication Data
US 2011/0092892 A1    Apr. 21, 2011

Related U.S. Application Data

(63) Continuation-in-part of application No. PCT/IL2009/000346, filed on Mar. 26, 2009.

(60) Provisional application No. 61/043,136, filed on Apr. 8, 2008, provisional application No. 61/078,873, filed on Jul. 8, 2008, provisional application No. 61/298,265, filed on Jan. 26, 2010.

(51) Int. Cl.
*A61M 31/00* (2006.01)
*A61M 3/02* (2006.01)
(Continued)

(52) U.S. Cl.
CPC .......... *A61M 3/0283* (2013.01); *A61B 1/00068* (2013.01); *A61M 1/0064* (2013.01); *A61B 1/12* (2013.01); *A61M 3/0295* (2013.01)

(58) Field of Classification Search
CPC ... A61M 1/0064; A61M 1/0058; A61M 3/02; A61M 3/0279; A61M 3/0295; A61M 3/0283; A61B 1/12; A61B 1/00068
USPC ............. 604/275, 28, 35, 524, 523, 246, 278, 604/277; 600/114, 115; 606/192
See application file for complete search history.

(56) References Cited

U.S. PATENT DOCUMENTS 3,109,426 A * 11/1963 Noonan et al. ................... 604/33
4,767,404 A *  8/1988 Renton ........................... 604/48
(Continued)

FOREIGN PATENT DOCUMENTS

JP    52024393 A    2/1977
JP    61293472 A   12/1986
(Continued)

OTHER PUBLICATIONS

International Search Report for PCT/IL2009/000346, mailed Aug. 5, 2009.

(Continued)

*Primary Examiner* — Theodore Stigell
*Assistant Examiner* — Tiffany Legette
(74) *Attorney, Agent, or Firm* — William D. Schmidt, Esq.; Sorell, Lenna & Schmidt, LLP

(57) ABSTRACT

The present invention provides a body passage cleansing device suitable for being passed through an internal channel of an endoscope, comprising a distal plug having a proximal end and a distal end, wherein said plug comprises channels, apertures and/or nozzles which are capable of allowing the passage of a fluid therethrough from said proximal end to said distal end, wherein said plug is connected to the distal end of a wire or other actuating means; wherein at least an outer portion of said distal plug is capable of being elastically deformed such that the external diameter and/or outline thereof may be reduced in response to inwardly-directed compression forces exerted thereon; and wherein said channels, apertures and/or nozzles are in a closed conformation when said distal plug is subject to said compression forces, and in an open conformation when said plug is not subject to said compression forces.

31 Claims, 29 Drawing Sheets

(51) Int. Cl.
*A61B 1/00* (2006.01)
*A61M 1/00* (2006.01)
*A61B 1/12* (2006.01)

(56) References Cited

U.S. PATENT DOCUMENTS

| | | | |
|---|---|---|---|
| 5,575,694 A | 11/1996 | Hawkins | |
| 5,630,795 A * | 5/1997 | Kuramoto | A61B 1/00068 600/153 |
| 5,908,403 A * | 6/1999 | Bosma et al. | 604/43 |
| 5,957,900 A * | 9/1999 | Ouchi | 604/264 |
| 6,309,379 B1 * | 10/2001 | Willard et al. | 600/467 |
| 7,234,651 B2 * | 6/2007 | Mousavi et al. | 239/201 |
| 7,951,073 B2 | 5/2011 | Freed | |
| 2003/0078616 A1 * | 4/2003 | Ginn | A61B 17/0057 606/213 |
| 2005/0159648 A1 * | 7/2005 | Freed | A61B 17/32056 600/159 |
| 2007/0005002 A1 * | 1/2007 | Millman | A61B 19/2203 604/30 |
| 2007/0015965 A1 * | 1/2007 | Cox | A61B 1/00082 600/114 |

FOREIGN PATENT DOCUMENTS

| | | |
|---|---|---|
| JP | 08155038 A | 6/1996 |
| JP | 2001087393 A | 4/2001 |

OTHER PUBLICATIONS

Written Opinion of the International Searching Authority for PCT/IL2009/000346, mailed Aug. 5, 2009.

* cited by examiner

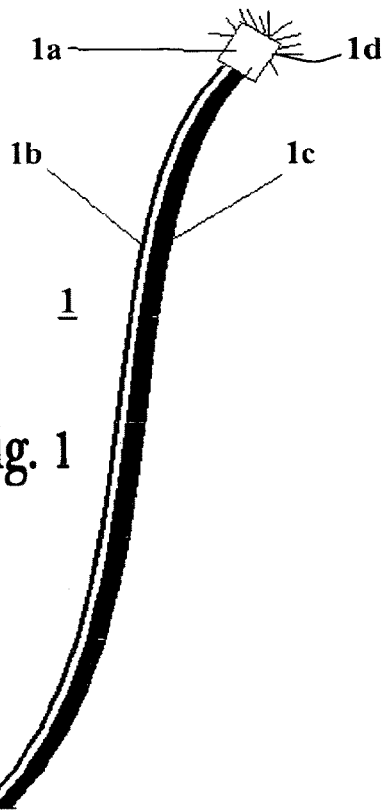
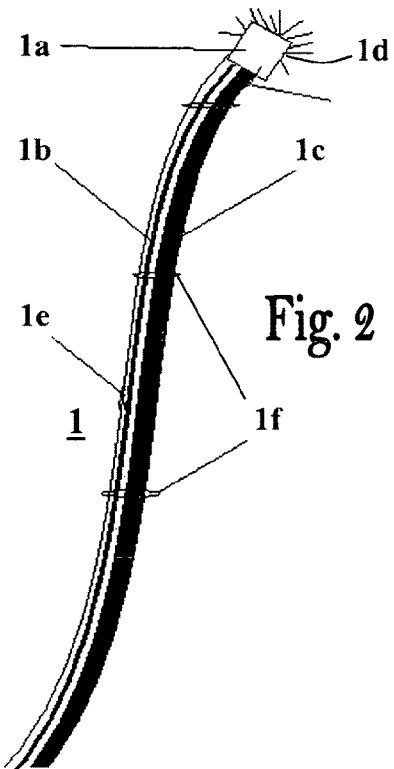
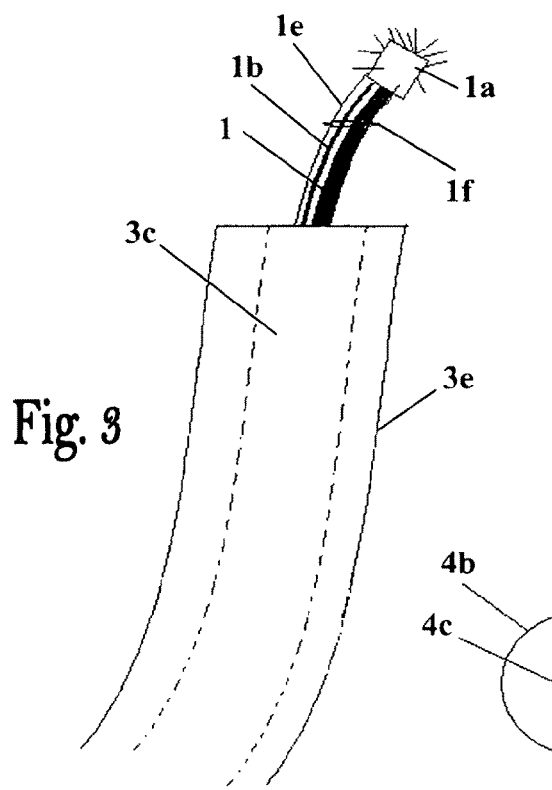
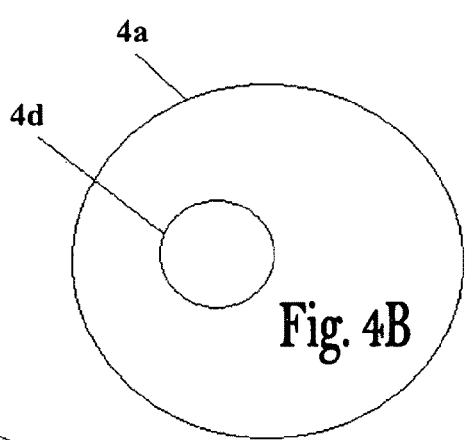
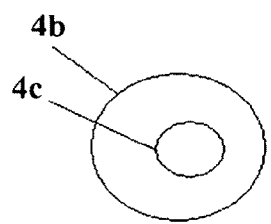

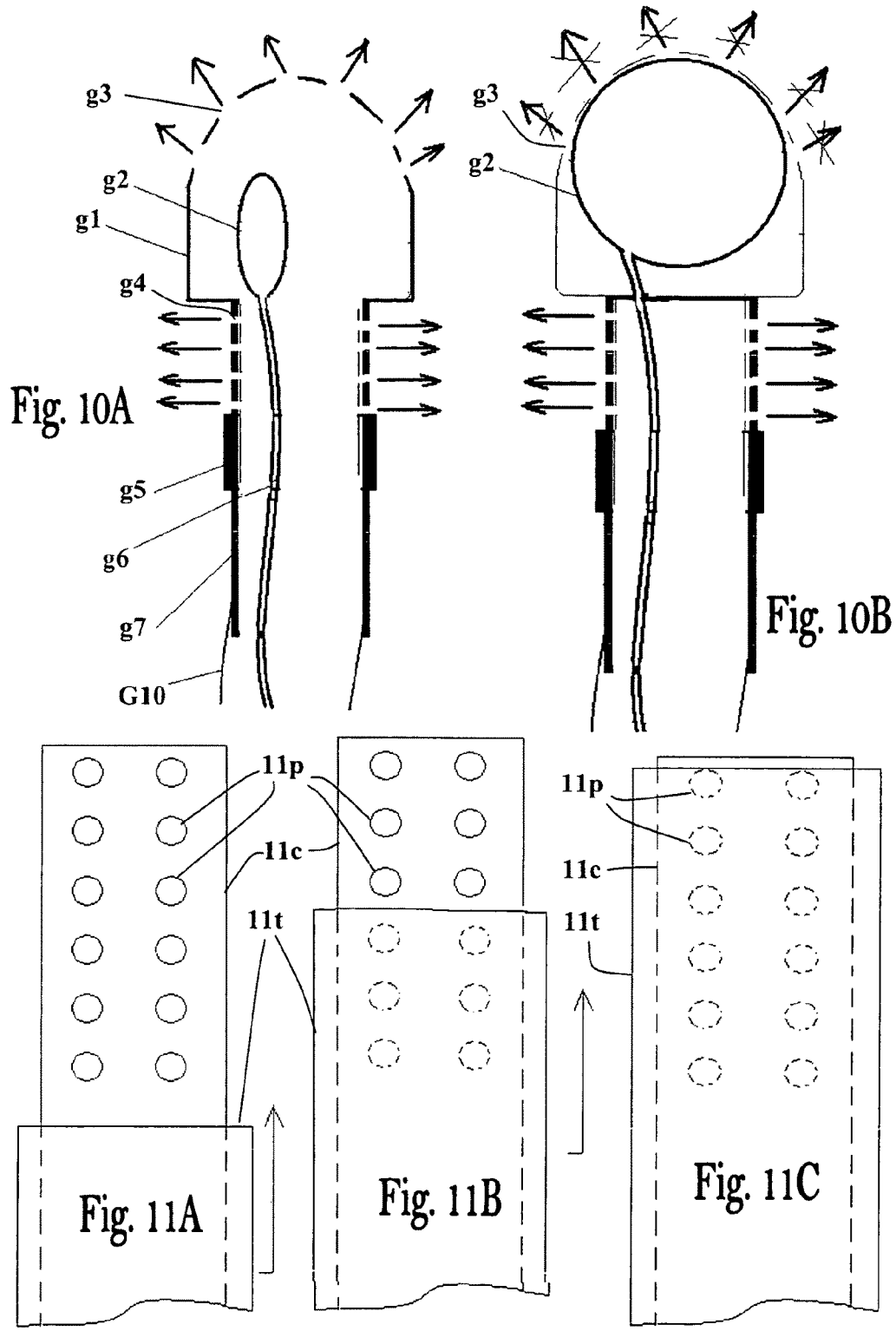

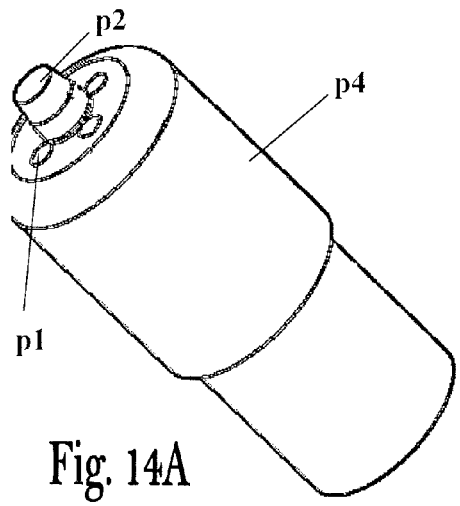
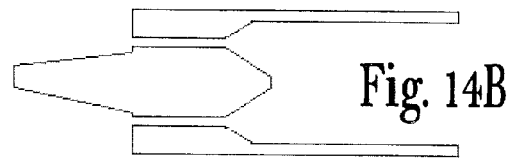
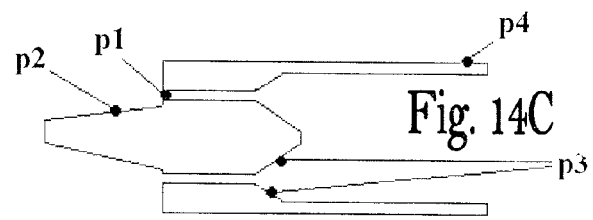
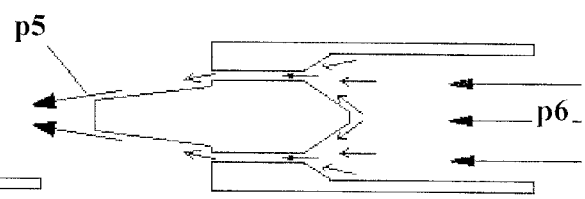
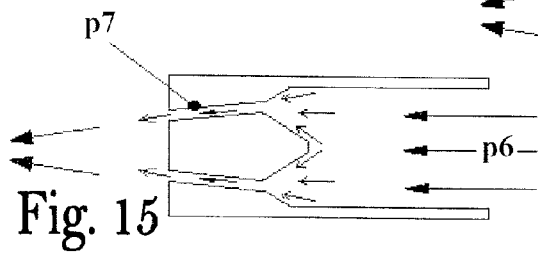
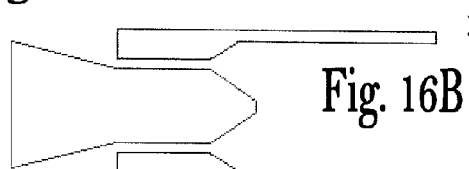
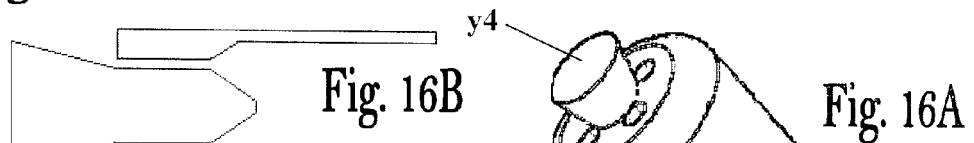
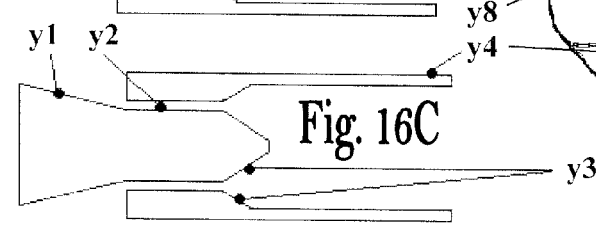
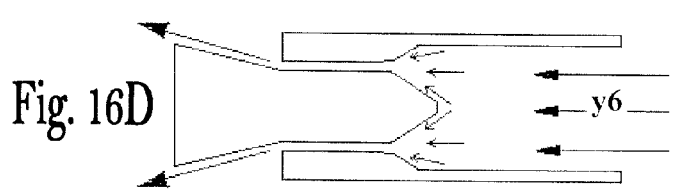
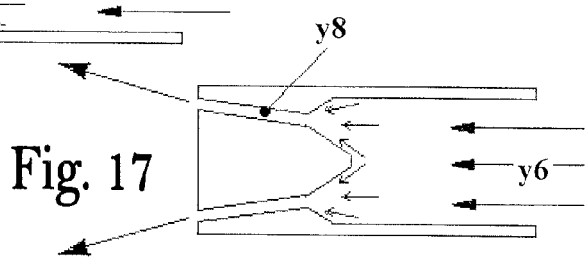

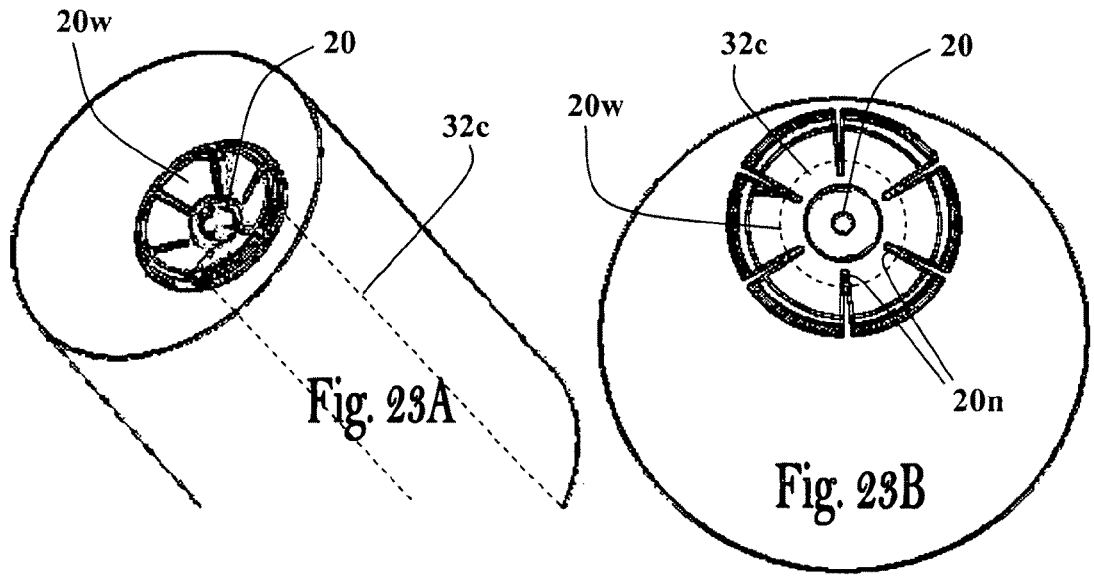
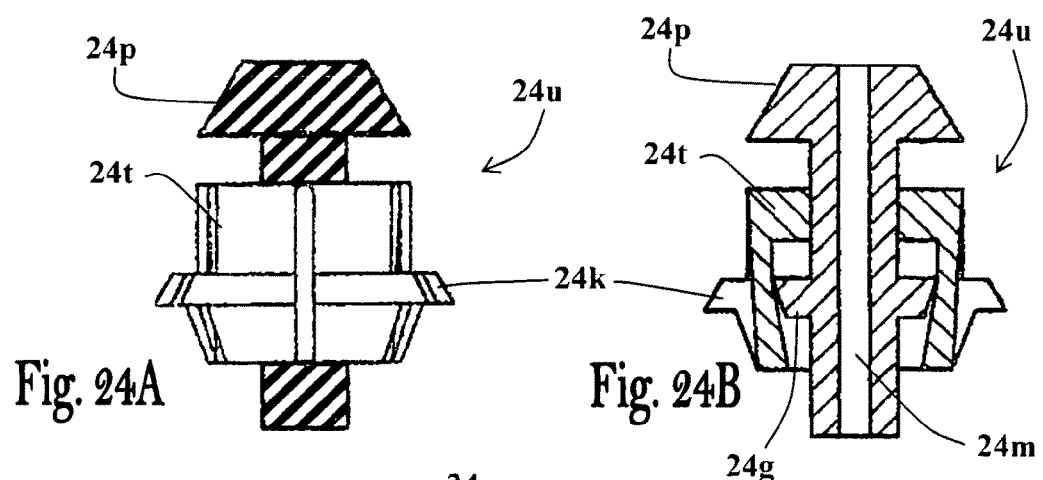
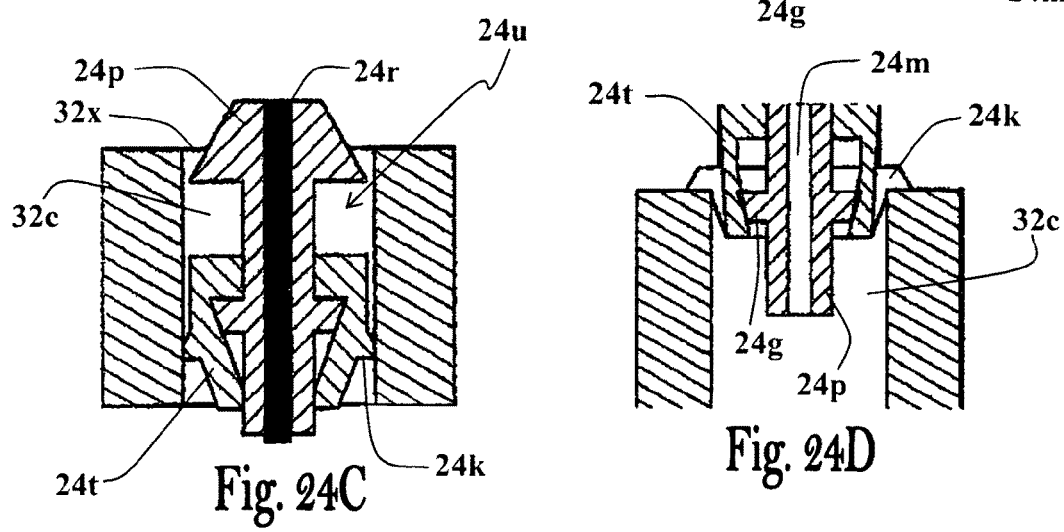

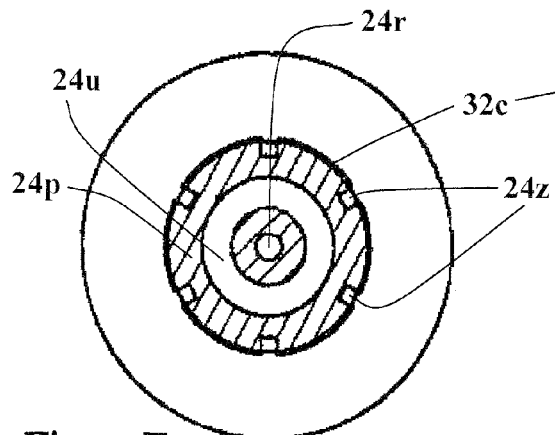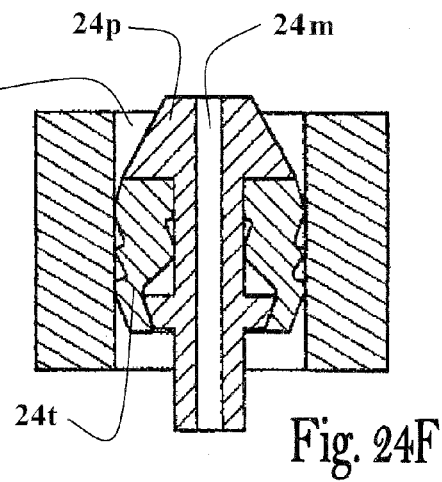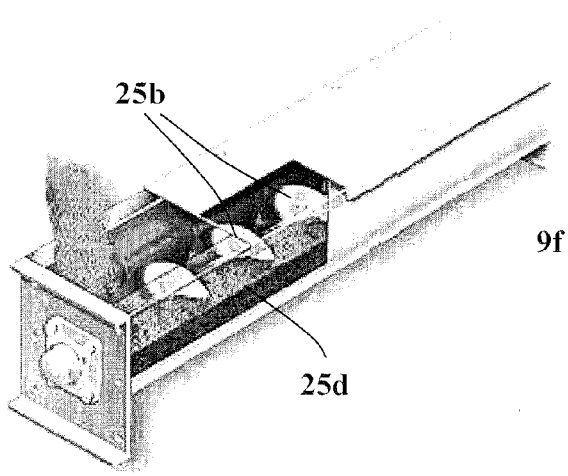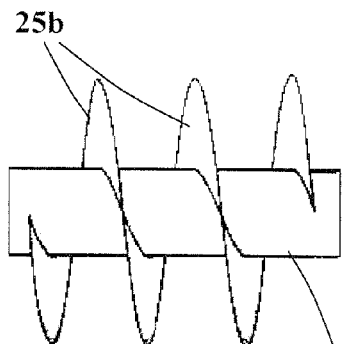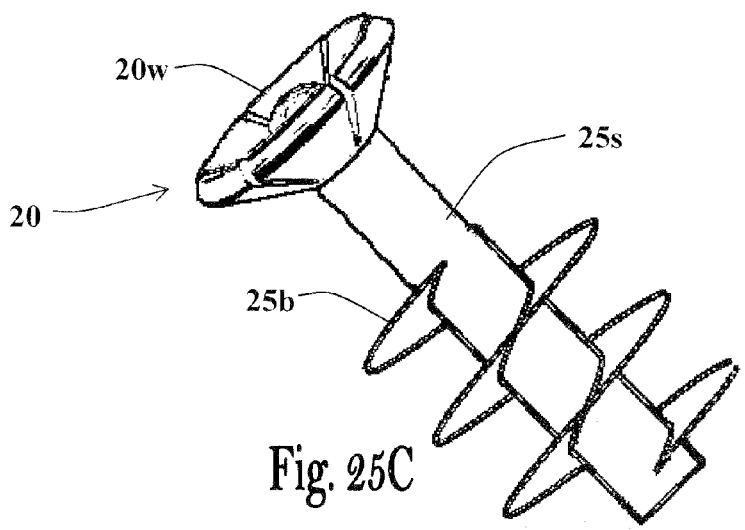

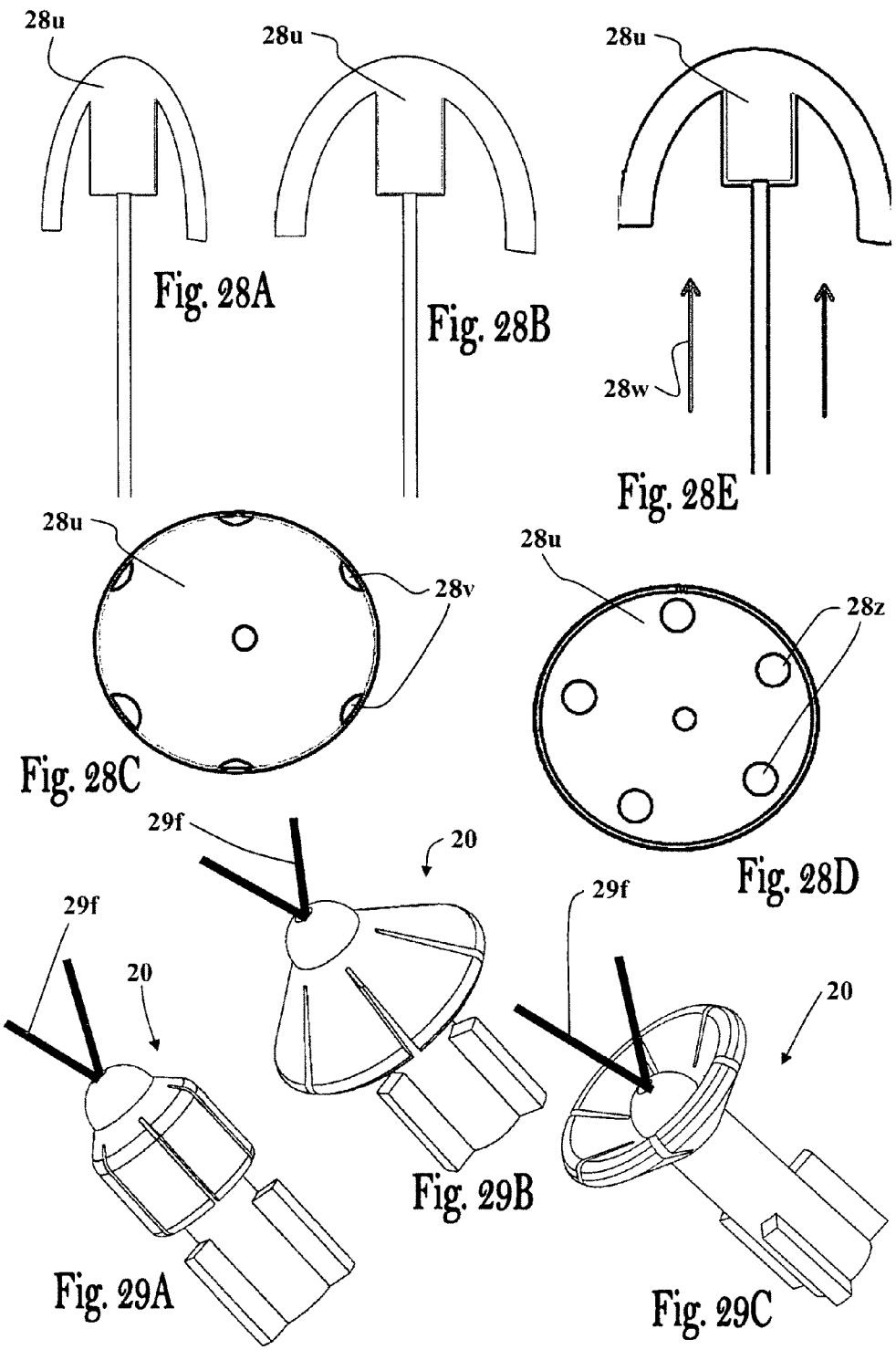

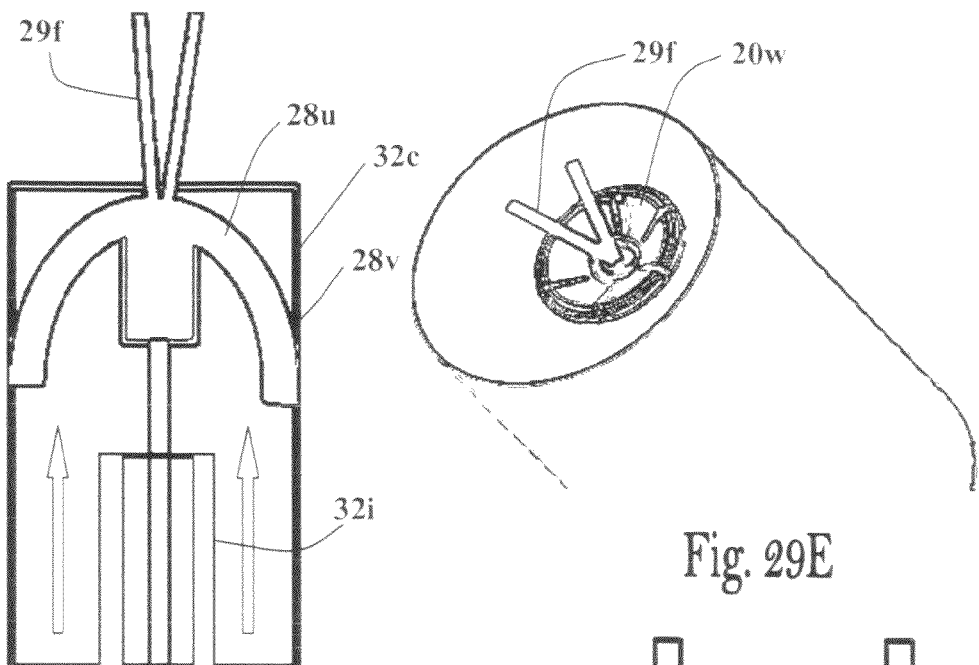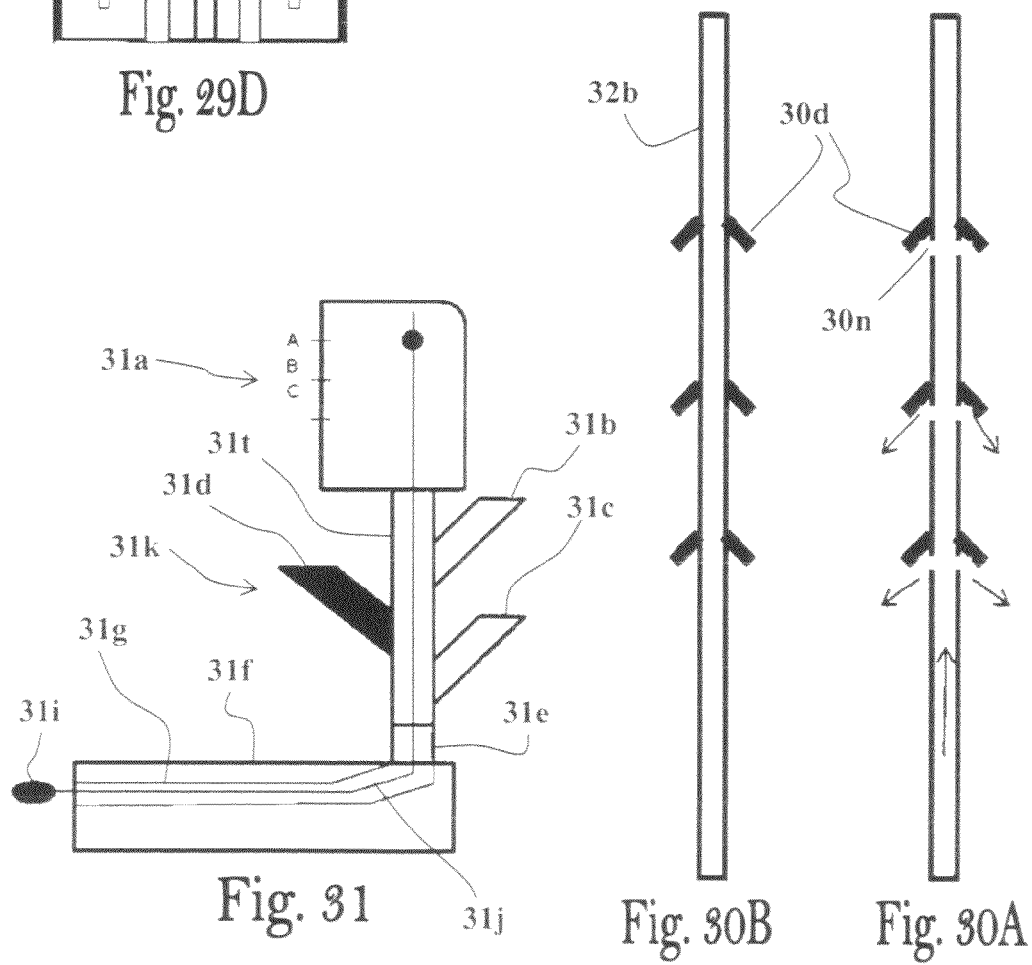

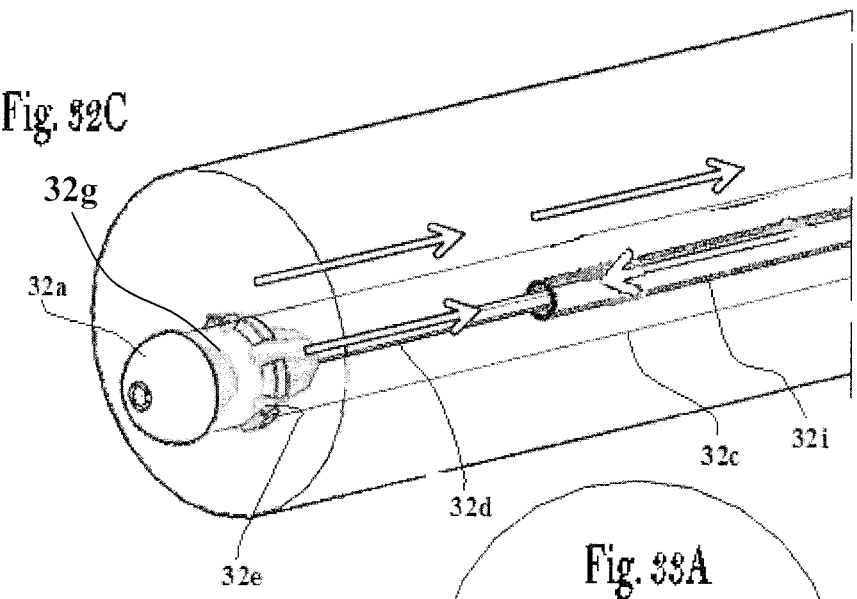
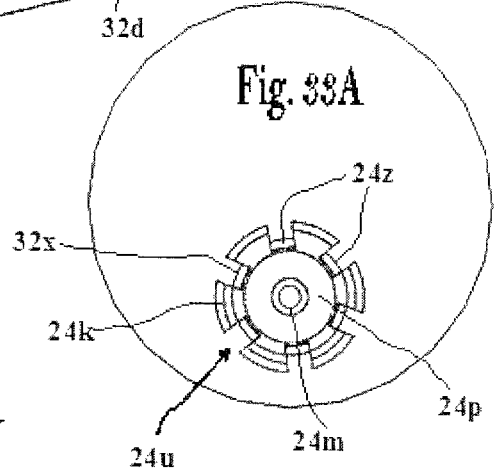
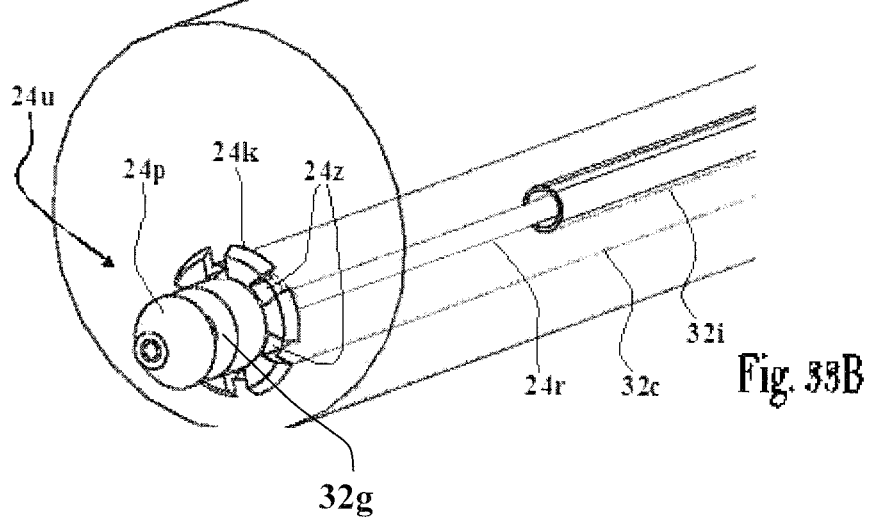

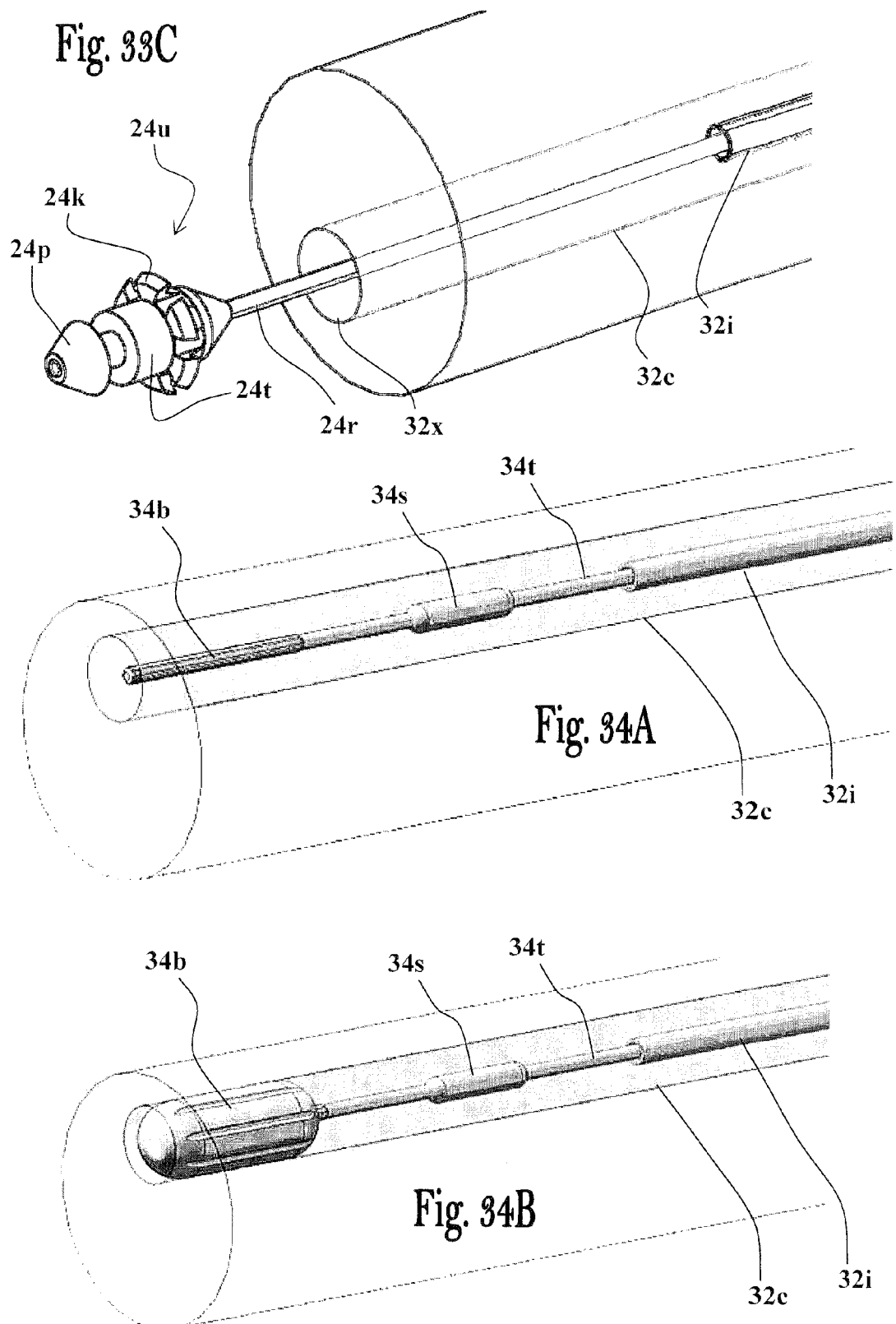

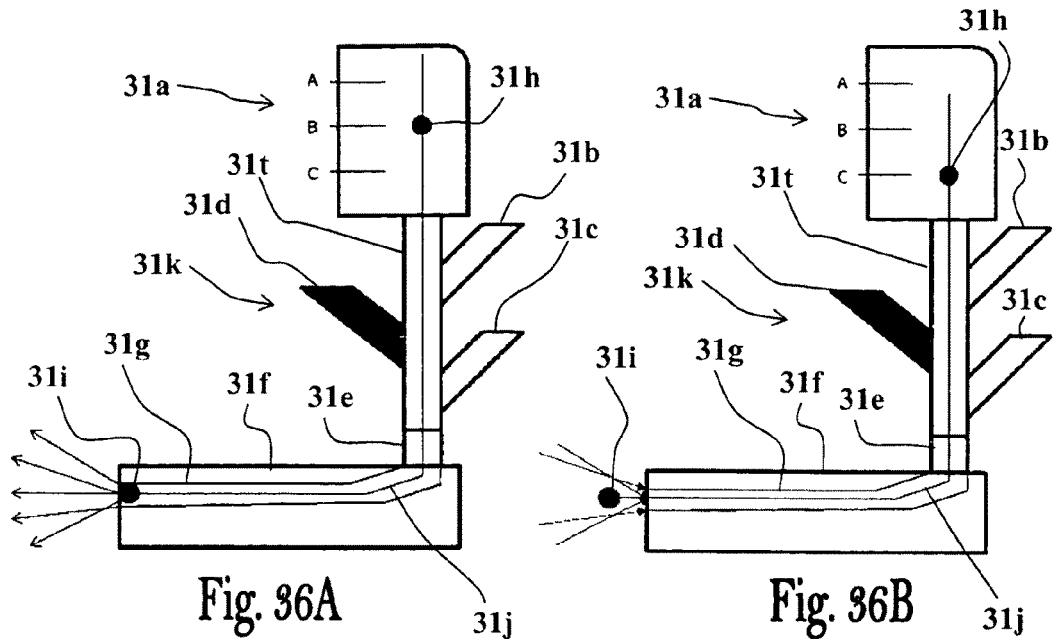
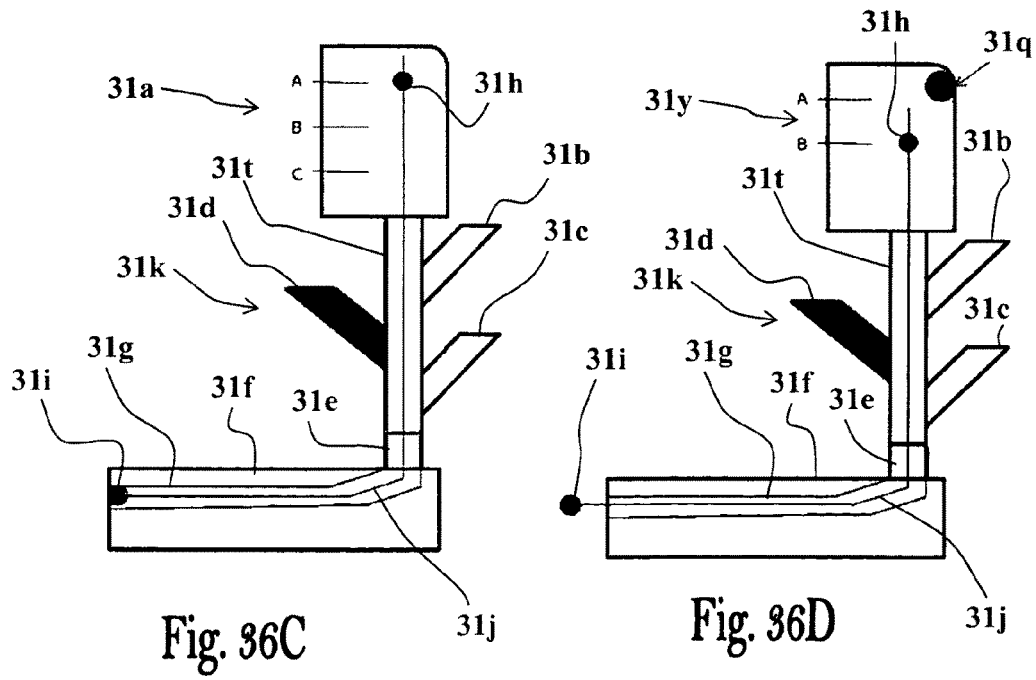

BODY PASSAGE CLEANSING DEVICE

This application is a Continuation-In-Part of International Application No. PCT/IL2009/000346, filed 26 Mar. 2009, which designated the U.S. and claims the benefit of US Provisional Application Nos. 61/043,136, filed 8 Apr. 2008; and U.S. Provisional Application No. 61/078,873 filed 8 Jul. 2008, the application also hereby claims priority on U.S. Provisional Application No. 61/298,265, the entire contents of which is hereby incorporated by reference.

FIELD OF THE INVENTION

The present invention relates to a device for cleaning the lumen of the colon or other body cavity. More specifically, said device is constructed such that it permits both optimal irrigation of the body passage and large-volume aspiration of the irrigation fluid and debris.

BACKGROUND OF THE INVENTION

During endoscopic procedures the physician inserts a flexible endoscope manually and navigates the device by visualizing the internal path using the integrated camera. In Colonoscopy, despite the use of various pre-colonoscopy cleansing regimes, in many cases the operator's field of view is severely restricted by fecal debris and other particulate matter that is left behind in the colonic lumen or other body passage.

Various attempts have been made to provide procedures and means for washing the colonic lumen prior to performing a colonoscopic investigation. The diagnostic accuracy and the therapeutic safety of colonoscopy (as well as of other diagnostic/therapeutic procedures such as virtual colonoscopy, sigmoidoscopy, barium enemas and pill camera) depend, to a large extent, on the quality of the colonic cleansing or preparation. The ideal preparation for colonoscopy would be one that is acceptable to the patient, cleans the bowel and reliably empties the colon of all fecal material in a rapid fashion without causing damage to the colonic tissues. An ideal preparation would also minimize or eliminate any patient discomfort. Common preparations for cleansing include diet in combination with a cathartic agent, polyethylene glycol preparations, gut lavage and phosphate preparations (oral sodium phosphate and tablet form of sodium phosphate). The use of each of these techniques, however, has significant limitations.

Various attempts have been made to provide procedures and means for washing the colonic lumen during the endoscopic procedure by means of flushing water through the working channel onto the gastro-intestinal (GI) tract walls to spray the mucosa and cleanse it of areas of bleeding, fecal remains etc., and aspirating the liquids and remains through the working channel. In certain endoscopes there exists a separate small channel (e.g. 0.8 mm diameter) for irrigation, in addition to the aspiration channel. It has been found that flushing liquids through the working channel and/or the abovementioned smaller channel is not effective. Thus, when the working channel is used for this purpose, the fluids do not have sufficient force momentum to wash the debris and is only effective for cleansing minor areas of bleeding and for very soft feces. In the case of the small channel, it is possible to achieve higher liquid momentum that could, in principle, be used to cleanse fecal material, but such a procedure is not effective since it has only one point focus and would require the endoscope head to be moved in order to cleanse a larger area.

In prior art methods, aspiration has been achieved using vacuum pressure through the endoscope working channel. While this is relatively effective when aspirating liquid remains and/or extremely soft solid fecal material, it is less so when dealing with thicker and harder fecal material. It has previously been suggested that endoscopes with a larger channel (up to 6 mm) may be used, but this solution is limited since the main limitation of the aspiration, in addition to the limited aspiration channels, is the vacuum pressure force that is limited to 1 atm.

In principle, it should be possible to use the endoscope working channel both for insertion of endoscopic accessories such as: biopsy forceps, polypectomy snares, injection needle, spray catheters etc and for insufflation and suction of air that assist the insertion of the endoscope. It is further used for passage of cleansing fluid to the region of the colon immediately distal to the distal end of the endoscope and for the aspiration and removal of said fluid together with fecal debris. However, when using the working channel of the endoscope the irrigation has no momentum since only minimal resistive pressure exists and the irrigation fluid introduced has very low efficacy. One way to overcome this problem would be to use a catheter that is introduced to the working channel with a build in nozzle on the distal end of the catheter to enable efficient cleansing. However, a major drawback of such an approach is the fact that the presence of an irrigation catheter in the working channel would restrict the available volume that may be used for aspiration. Furthermore, the restriction in working channel volume would also prevent said volume being used for the passage of endoscopic tools or for insufflation and/or aspiration of air and aspiration of debris.

It is therefore a primary aim of the present invention to provide a device that permits effective and higher-pressure irrigation of a body cavity via an endoscopic working channel while still allowing for the use of the same working channel for other purposes, most particularly the aspiration of fluid and debris from said body cavity.

A further aim of the present invention is to provide a device that will permit irrigation and cleansing of the working channel of an endoscopic instrument without the removal of said instrument from the body, such that blockages of said channel by fecal material and debris may be prevented or removed.

A further aim of the present invention is to provide a device that will permit irrigation, cleansing and aspiration for additional applications such as: upper and lower GI bleeding, bronchoscopy, cystoscopy, gastrostomy trauma surgery where no preparation was available and endo-surgery preparation. It is a primary objective to irrigate and aspirate blood and clots as well as feces and remains in an effective way without blockage of the aspiration channel by clots and/or feces.

A further aim of the invention is to permit the upgrading of all endoscopic devices by integrating them together with a nozzle assembly, thereby not requiring the replacement of tools (for example biopsy forceps, snares, injection needles, and so on) during the procedure.

Further aims and objectives will be discussed as the description proceeds.

SUMMARY OF THE INVENTION

The present inventors have unexpectedly found that it is possible to utilize a single working channel of an endoscope (or internal lumen of another elongate medical instrument such as a catheter or cannula) for both passing irrigation fluid distally and aspirating fluid and solid debris proximally, wherein both of these processes may be performed in a highly effective manner as part of a procedure for cleansing internal body passages and cavities.

The present invention is primarily directed to a body passage cleansing device suitable for passage through an endoscopic channel, comprising at least one distal plug having a proximal end and a distal end, wherein said plug comprises channels, apertures and/or nozzles which are capable of allowing the passage of a fluid therethrough from said proximal end to said distal end,
- wherein said plug is connected to the distal end of an actuating element (such as a wire, tube, cord or rod);
- wherein at least an outer portion of said distal plug is capable of being elastically deformed such that the external outline or diameter thereof may be reduced in response to inwardly-directed compression forces exerted thereon;
- and wherein said channels, apertures and/or nozzles are in a closed conformation when said distal plug is subject to said compression forces, and in an open conformation when said plug is not subject to said compression forces.

In one particularly preferred embodiment of this aspect of the invention, the actuating element is a wire (also referred to herein as a guidewire).

It should be noted that for the purpose of the present disclosure the term "distal spray head unit" and the like are sometimes used interchangeably with the term "distal plug". It should further be noted that the term 'distal' refers to the direction away from the operator and towards the center of the patient's body. Consequently, the term 'proximal' is taken to refer to the opposite direction.

In one preferred embodiment of the invention, the external diameter of the distal plug when not subjected to inwardly-directed radial compression forces is slightly larger than the internal diameter of an endoscope working channel. In many cases, the internal diameter of the working channel in a colonoscope is 3.8 mm, and generally in the range of 2-4 mm.

In one particularly preferred embodiment of the device, the distal plug comprises an O-ring.

In a particularly preferred embodiment of the aforementioned device, said device further comprises a partial length inner tube surrounding the wire in a coaxial manner,
- wherein said inner tube extends from the proximal end of said wire;
- and wherein the length of said tube is less than the length of said wire, such that a portion of the distal region of said wire is left unenclosed by said tube.

In a further particularly preferred embodiment of the aforementioned device, said device further comprises an outer tube disposed such that it surrounds the aforementioned inner tube, guidewire and distal spray head of said device Thus, a further preferred embodiment of the present invention is directed to a body passage cleansing device suitable for passage through an endoscopic channel, comprising a distal plug having a proximal end and a distal end, wherein said plug comprises channels, apertures and/or nozzles which are capable of allowing the passage of a fluid therethrough from said proximal end to said distal end,
wherein said plug is connected to the distal end of a wire;
wherein at least an outer portion of said distal plug is capable of being elastically deformed such that the external diameter thereof may be reduced in response to inwardly-directed radial compression forces exerted thereon;
and wherein said channels, apertures and/or nozzles are in a closed conformation when said distal plug is subject to said compression forces, and in an open conformation when said plug is not subject to said compression forces;
wherein said device further comprises a partial length inner tube surrounding the wire in a coaxial manner, wherein said tube extends from the proximal end of said wire, and wherein the length of said tube is less than the length of said wire, such that a portion of the distal region of said wire is left unenclosed by said tube;
and wherein said device further comprises a partial length outer tube surrounding said inner tube and actuating means in a coaxial manner.

It should be noted that for the purpose of the present disclosure the term "distal spray head unit" and the like are sometimes used interchangeably with the term "distal plug".

In another particularly preferred embodiment, the device further comprises a proximal control handle,
- wherein the proximal end of the tube is connected to said handle;
- wherein the proximal end of the actuating means is movably connected to said handle;
- wherein said handle comprises means for changing the distance between said handle and the distal end of said actuating means;
- wherein said handle comprises one or more passages for connecting a fluid-supply channel to one of two or more fluid outlet channels;
- and wherein said handle comprises means for switching between the fluid outlet channels to which said fluid-supply channel is connected.

Preferably, the proximal handle disclosed immediately hereinabove comprises one fluid outlet channel in fluid communication with the lumen of the partial length tube, and a second fluid outlet channel in fluid communication with the space surrounding the external surface of said tube. When inserted into the working channel of an endoscope, this latter space will be bounded externally by the walls of said channel.

Preferably, the means for changing the distance between the handle and the distal end of the actuating means comprises a slider mounted on said handle.

The present invention also encompasses an additional preferred embodiment of a proximal handle that may be used to operate endoscopic instruments, such as the colonic cleansing device of the present invention. In this embodiment, which will be described in more detail hereinbelow, the handle incorporates a novel mechanism for directing flow to different lumens and conduits. It is to be emphasized that in addition to its use in conjunction with the colonic cleaning device incorporating the partial length outer tube disclosed above, said proximal handle may also be used together with variants of this device (e.g. not comprising an outer tube) and indeed with other endoscopic instruments.

Thus, a cleansing device of the present invention may further comprise a proximal handle,
- wherein the proximal ends of both the inner and outer tubes are connected to said handle;
wherein the proximal end of the actuating means is movably connected to said handle;
wherein said handle comprises means for changing the distance between said handle and the distal end of said actuating means;
wherein said handle comprises switching means for directing the output of a fluid-supply channel to one or more fluid outlet channels;
and wherein said handle comprises coupling means for coordinating the aforementioned switching between the fluid outlet channels with said means for changing the distance between said handle and the distal end of the actuating means.

In one preferred embodiment of this preferred embodiment of the proximal handle, the aforementioned switching means comprises a multi-way fluid valve.

In one preferred embodiment, the coupling means comprises a mechanical actuator (for example in the form of an elongated strip or bar) which is connected to both the aforementioned slider mechanism and to said switching means.

Preferably, the proximal handle disclosed immediately hereinabove comprises one fluid outlet channel in fluid communication with the lumen of the partial length inner tube, and a second fluid outlet channel in fluid communication with the space located between the external surface of said tube and the inner wall of the outer tube.

In another aspect, the present invention provides a body passage cleansing device suitable for passage through an endoscopic channel, comprising a distal head spray unit fitted with channels, apertures and/or nozzles formed therewithin,
  wherein said distal head spray unit is connected to the distal end of a collapsible catheter and to the distal end of an associated stiffening wire;
  wherein said collapsible catheter is capable of adopting an expanded conformation when a fluid stream is passed through it and of adopting a collapsed conformation in the absence of the passage of a fluid stream therethrough.

In one preferred embodiment of this aspect of the invention, the collapsible catheter is a single lumen catheter. In another preferred embodiment, said catheter is a bilumen or multilumen catheter.

In a further aspect, the present invention also provides a system for cleansing body passages comprising:
a) a device according to any one of the embodiments disclosed hereinabove and described in detail hereinbelow;
b) an aspiration pump;
c) an irrigation pump;
d) relays, transformers and computer equipment for controlling the functioning of said device and pumps.

The present invention further provides a method for cleansing a body passage comprising:
a) inserting an elongate medical device into said body passage such that the distal end thereof becomes located close to, and on the proximal side of, the area of said passage to be cleansed;
b) passing a distal plug fitted with channels, apertures and/or nozzles formed therewithin through an internal channel of said elongate medical device such that said plug becomes located beyond the distal exit of said internal channel and in contact with the distal face of said medical device;
c) introducing irrigation fluid into said internal channel at a pressure that is sufficient to cause said fluid to form a spray or jet upon passing through the channels, apertures and/or nozzles formed in said distal plug;
d) allowing said spray or jet to cleanse the region of the body passage that is situated immediately distal to the end of said channel;
e) causing said distal plug to move distally such that there is no contact between said plug and the distal face of said elongate medical instrument within the body passage;
f) applying a negative pressure to the proximal end of the internal channel of the elongate medical instrument, in order to cause aspiration of fluid and solid particulate matter through said internal channel;
g) if necessary, bringing said distal plug back to the location defined in step (b) and repeating steps (c) to (f).

In a particularly preferred embodiment of this method, the elongate medical instrument is an endoscope and the internal channel is a working channel contained therein. In one especially preferred embodiment, the endoscope is a colonoscope and the body passage to be cleansed is a portion of the large intestine.

In one preferred embodiment of this method, the aforementioned distal plug is attached to a guidewire.

In a particularly preferred embodiment of this method, the guidewire is surrounded (in a coaxial fashion) by a partial length inner tube that extends distally from the proximal end of said guidewire, wherein the length of said tube is less than the length of said wire, such that a portion of the distal region of said wire is left unenclosed by said tube. In a particularly preferred embodiment of this version of the method, said method further comprises the steps of:
i) withdrawing the distal plug into the distal end of the internal channel such that said plug is radially compressed, thereby causing its external diameter to be reduced, thereby sealing the distal end of said internal channel;
ii) introducing irrigation fluid into the lumen of the partial length tube such that when said fluid leaves the distal end of said tube, the positive fluid pressure provided thereby assists in preventing or removing blockages in the distal portion of the internal channel of the elongate medical device.

In a further preferred embodiment of the method disclosed immediately hereinabove, the partial length tube is surrounded coaxially by an outer tube.

The present invention further provides a method for cleansing a body passage comprising:
a) inserting an elongate medical device into said body passage such that the distal end thereof becomes located close to, and on the proximal side of, the area of said passage to be cleansed;
b) passing a device comprising a distal head spray unit fitted with channels, apertures and/or nozzles formed therewithin through an internal channel of said elongate medical device, wherein said distal head spray unit is connected to the distal end of a collapsible catheter and to the distal end of an associated stiffening wire, such that said distal spray head unit becomes located beyond the distal exit of said internal channel;
c) introducing irrigation fluid into the lumen of said collapsible catheter at a pressure that is sufficient to cause said fluid to form a spray or jet upon passing through the channels, apertures and/or nozzles formed in said distal spray head unit;
d) allowing said spray or jet to cleanse the region of the body passage in which said distal spray head unit is located;
e) closing the supply of irrigation fluid to the lumen of said collapsible catheter, and optionally applying a negative pressure to the proximal opening of said lumen, such that the walls of said catheter collapse thereby decreasing the volume of the internal channel occupied by said catheter;
f) applying a negative pressure to the proximal end of the internal channel of the elongate medical instrument, in order to cause aspiration of fluid and solid particulate matter through said internal channel;
g) if necessary, repeating steps (c) to (f).

Other advantages and features of the invention will become apparent as the description proceeds

BRIEF DESCRIPTION OF THE DRAWINGS

The present invention is illustrated by way of example in the accompanying drawings, in which similar references consistently indicate similar elements and in which:

FIG. 1 schematically illustrates one preferred embodiment of a single lumen collapsible catheter of the invention;

FIG. 2 schematically illustrates an embodiment of the single lumen collapsible catheter shown in FIG. 1, having a control wire and flexible tie wrap rings;

FIG. 3 schematically illustrates the catheter shown in FIG. 2 when introduced via a working channel of an endoscope;

FIGS. 4A and 4B respectfully illustrate an irrigation tube and a colonoscope of the prior art;

FIGS. 10A and 10B schematically illustrate an irrigation catheter of the invention in which a balloon is employed for controlling irrigation modes, where in FIG. 10A the balloon is in a deflated state and in FIG. 10B it is in an inflated state;

FIGS. 11A to 11C schematically illustrate a distal spray head embodiment of the invention employing slideable overtube for controlling the jet spray in a proximal-most position state in FIG. 11A, in a partially cover state in FIG. 11B, and in a distal-most position in FIG. 11C;

FIGS. 14A to 14D schematically illustrate a distal spray head embodiment configured to direct the flow of irrigation fluid in a convergent direction, wherein FIG. 14A shows a perspective view of the distal spray head, and FIGS. 14B to 14D show sectional views illustrating the flow passing thereinside;

FIG. 15 shows a sectional view of a distal spray head embodiment of the invention configured to direct the flow of irrigation fluid in a convergent direction by means of a pre-set internal nozzle angle;

FIGS. 16A to 16D schematically illustrate a distal spray head embodiment of the invention configured to provide a divergent flow, wherein FIG. 16A shows a perspective view of the distal spray head, and FIGS. 16B to 16D show sectional views illustrating the flow passing thereinside;

FIG. 17 schematically illustrate a distal spray head embodiment of the invention configured to provide a divergent flow by means of a pre-set internal nozzle angle;

FIGS. 19A and 19B schematically illustrate an embodiment of the cleansing catheter of the invention comprising a filter, wherein FIG. 19A shows the filter assembled on the distal part of catheter tube and FIG. 19B shows the catheter and filter when introduced via a colonoscope;

FIGS. 20A and 20B show perspective views of one preferred embodiment of the distal head unit of the invention in a "closed" conformation, wherein FIG. 20A shows a perspective front view and FIG. 20B shows a perspective back view;

FIGS. 21A and 21B show perspective views of the distal head unit shown in FIGS. 20A and 20B in a conical/frusto-conical conformation, wherein FIG. 21B shows a perspective front view and FIG. 21A shows a perspective back view;

FIGS. 22A and 22B shows perspective views of the distal head unit shown in FIGS. 20A and 20B in a second frusto-conical conformation, wherein FIG. 22A shows a perspective front view and FIG. 22B shows a perspective back view;

FIGS. 23A and 23B respectively show perspective and front views of the spray head unit shown in FIGS. 20 to 22 in the irrigation mode when placed over the exit opening of the working channel;

FIGS. 24A to 24F show side and sectional views of one preferred embodiment of the spray head unit constructed from a flexible plug placed over an inner rigid element, wherein FIG. 24A shows a side view of the spray head unit, FIG. 24B shows a sectional view of the spray head unit, FIG. 24C shows a sectional view of the spray head unit when advanced inside the working channel, FIGS. 24D and 24E respectively show sectional and top views of the spray head unit in the irrigation mode wherein it is placed over the exit opening of the working channel, and FIG. 24F shows a sectional view of the spray head unit when it is retracted back into, and sealably lock the passage through, the working channel;

FIGS. 25A to 25C illustrate an exemplary mechanism which may be used with the device of the invention for removal of solid debris;

FIGS. 27A to 27D schematically illustrate a preferred embodiment of the invention wherein the spray head unit is provided in the form of a small balloon, wherein FIG. 27A shows a front view of the balloon in a deflated state, FIG. 27B shows the balloon in an inflated state, FIG. 27C shows the balloon in an inflated state inside the working channel, and FIG. 27D shows the balloon in a deflated state inside the working channel;

FIGS. 28A to 28E schematically illustrate an embodiment of the spray head unit provided in the form of a flexible mushroom-shaped valve, wherein FIG. 28A shows flexible mushroom-shaped valve in a reduced state, FIG. 28B shows flexible mushroom-shaped valve in an expanded state, FIGS. 28C and 28D show possible nozzle implementations in the flexible mushroom-shaped valve, and FIG. 28E show the flexible mushroom-shaped valve when expanded by a flow of irrigation fluid;

FIGS. 29A to 29E schematically illustrate distal spray head units of the invention comprising biopsy forceps;

FIGS. 30A and 30B schematically illustrate a possible embodiment wherein deflectors are mounted on the wire/tube of the catheter device, wherein FIG. 30A further illustrates an embodiment wherein a hollow wire or tube is used which further include washing apertures;

FIG. 31 schematically illustrate a cleansing device of the invention when introduced via a working channel of an endoscope/colonoscope;

FIGS. 32A to 32C depicts perspective views of three different states of a particularly preferred embodiment of the cleansing device in the working channel of the endoscope/colonoscope, where in FIG. 32A the rear portion of the distal spray unit is positioned in the distal end opening of the working channel, in FIG. 32B the distal spray unit is positioned entirely outside of the working channel, and in FIG. 32C a significant portion of the distal spray unit is sealably positioned inside working channel;

FIGS. 33A to 33C show further views of the spray head unit shown in FIG. 24 in the irrigation and aspiration modes, wherein FIGS. 33A and 33B respectively show front and perspective views of the spray head unit in the irrigation mode, wherein it is placed over exit opening of the working channel, and FIG. 33C shows a perspective view showing the state of spray head unit in the aspiration mode, wherein it is advanced further distally away from the exit opening of working channel;

FIGS. 34A to 34E shows a preferred embodiment of the invention wherein the catheter device comprises nozzle and sealing balloons, wherein FIG. 34A shows the catheter device inside working channel when both balloons are in a deflated state, FIGS. 34B and 34C show the catheter device inside working channel in the irrigation mode wherein nozzle balloon is in an inflated state and sealing balloon is in a deflated state, FIG. 34D shows the catheter device inside working channel in an aspiration mode wherein both balloons are in a deflated state, and FIG. 34E shows the catheter device inside working channel in a clearing mode wherein the nozzle balloon is in a deflated state and the sealing balloon is in an inflated state;

FIGS. 36A to 36D schematically illustrate changing operation modes of the device of the invention by means of a proximal control handle, wherein FIG. 36A illustrate setting the device into the irrigation mode by means of handle component, FIG. 36B illustrate setting the device into the aspiration mode by means of handle component, FIG. 36C illustrate setting the device into the clearing mode by means of handle component, and FIG. 36D schematically illustrates a proximal control handle further comprising a trigger for setting the device into the clearing operation mode;

FIGS. 38A to 38C schematically illustrate an embodiment of the catheter device of the invention wherein sealing of the distal end of the endoscope working channel is accomplished by means of a balloon mechanism, wherein FIG. 38A shows the device with the balloon in a deflated state, and FIGS. 38B and 38C show the device with the balloon in an inflated state;

FIGS. 40A and 40B schematically illustrate a preferred embodiment of a proximal control handle, wherein FIG. 40A shows the state of proximal control handle in the irrigation mode of operation and FIG. 40B show the state of proximal control handle in the working channel clearing mode of operation;

Figure 5A:
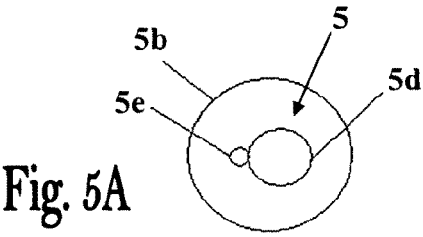
FIGS. 5A and 5B schematically illustrate cross-sectional views of an embodiment of the collapsible tube of the invention having an externally attached stiffening wire, where in FIG. 5A the tube is in an expanded state and in FIG. 5B it is in a collapsed state.

It should be noted that the embodiments exemplified in the Figures are not intended to be to scale and are in diagrammatic form to facilitate ease of understanding and description.

DETAILED DESCRIPTION OF PREFERRED EMBODIMENTS

The present invention provides two general solutions to the abovementioned technical problem that is encountered when using the endoscope working channel for both irrigation of a body passage (such as the colon) and for large-volume aspiration of the irrigation fluid (together with displaced solid and semi-solid debris). In the first of these two approaches, the device of the present invention incorporates a collapsible catheter which provides both a large volume irrigation lumen (when in its non-collapsed state) and a large volume aspiration lumen (i.e. the working channel volume) when said catheter is in its collapsed state.

In the second approach, the device comprises a novel distal plug/spray head mounted on the distal end of a guidewire. In one highly preferred embodiment of this approach, as will be described hereinafter, the device of the present invention further comprises a partial length non-collapsible catheter or sheath extending from the proximal end of the guidewire and ending a few centimeters short of the distal end of said guidewire. This partial length tube, in most cases, is non-collapsible, but in some embodiments may be provided in the form of a collapsible catheter. As will be explained further, this unique structure combines optimum irrigation and aspiration of the body cavity being treated or cleansed with the ability to prevent and free blockages of the endoscopic working channel which would otherwise occur during the cleansing process.

Collapsible Catheter Approach:

Two main embodiments of the collapsible catheter device will now be described: a single lumen catheter and a multi-lumen catheter.

First Main Embodiment

Single Lumen Collapsible Catheter

The first embodiment comprises a device that is introduced through the working channel of an endoscope to cleanse the colon. As shown in FIG. 1, the cleansing (or irrigation) catheter 1 comprises a collapsible sheath 1c and a metal (e.g. stainless steel or aluminum) stiffening wire 1b. The distal end of the sheath is in fluid connection with a jet spray head 1a that is fitted with nozzles 1d which are capable of directing the irrigation fluid spray, as will be described in more detail hereinbelow. The purpose of the distal end of the stiffening wire 1b, which is connected to the spray head 1a, is to permit insertion and advancement of catheter 1, even when the sheath is in its flaccid, collapsed state. In order to assist the operator in guiding the device of the invention, the stiffening wire 1b may contain one or more radiopaque materials at various points along its length (not shown). These radiopaque markers may be used to locate the device by means of real time visualization using X-ray imaging. The use of such markers is particularly important in upper GI endoscopic procedures, for example when introducing endoscopic tooling trough the papilla.

Figure 39:
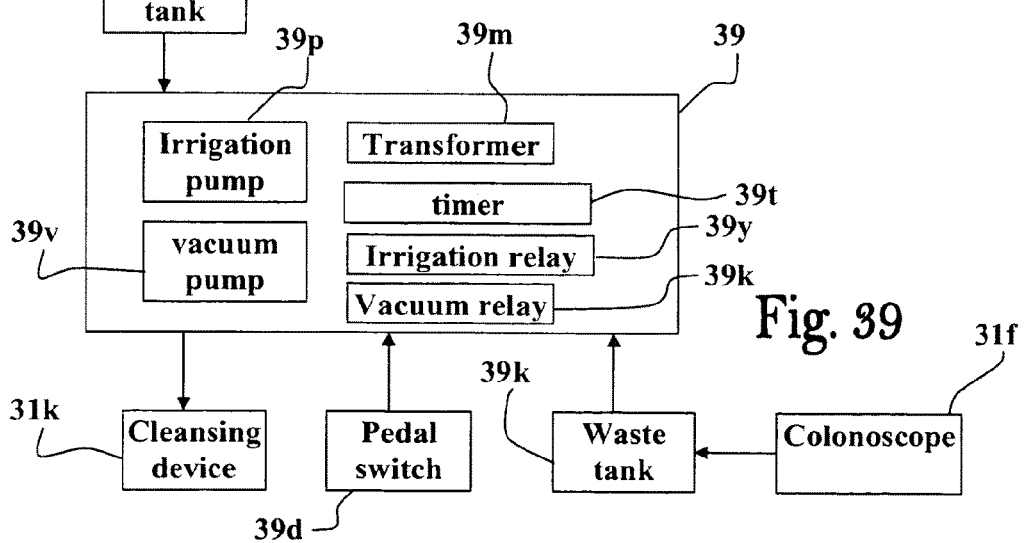
FIG. 39 is a block diagram illustrating a possible implementation of a console for operation of the cleansing device of the invention.

The proximal end of the catheter is connected to a source of irrigation fluid (e.g. saline) and suitable pumping apparatus shown in FIG. 39. When said irrigation fluid is pumped through catheter 10, the collapsible sheath adopts its fully expanded conformation, thereby allowing maximum transfer of the irrigation fluid to the jet spray head 1a. When the irrigation fluid ceases to flow through the catheter (e.g. as a result of both turning off the irrigation fluid pump and connecting the proximal end of the sheath to a negative pressure source), the collapsible sheath loses its source of structural rigidity (the column of irrigation fluid) and returns to its flaccid, collapsed state, thereby increasing the volume of the working channel that is external to the irrigation catheter. This is highly advantageous, for at least the following three reasons:
 a) maximum space for aspiration of irrigation fluid and fecal debris through the working channel is provided;
 b) additional space for the introduction and passage of endoscopic surgical tools (without the need to remove the irrigation catheter) is created; and
 c) insufflation of the body cavity (e.g. colon) may be performed in the presence of the collapsed catheter.

In the absence of the collapsible sheath of the present invention, it would be necessary to entirely remove the irrigation catheter from the working channel prior to applying suction thereto or inserting endoscopic tools therein. Thus, the collapsible catheter of the present invention has the distinct advantage of obviating the tedious and labor-intensive need for removing and re-inserting said catheter several times during the cleansing procedure.

As shown in FIG. 2, this embodiment of the device of the invention may also further comprise a control wire 1e for directing the distal jet spray head 1a during irrigation and aspiration, when said head is caused to leave the distal exit of the working channel. The distal end of control wire 1e is connected to the jet spray head 1a, while the proximal end remains outside of the patient's body (optionally terminating in a control handle, as is commonly used in endoscopic procedures).

While the stiffening wire 1b may be unconnected to the collapsible sheath 1c, in one preferred embodiment of the invention, said wire and said sheath may be mutually connected by means of plurality of flexible tie wrap rings 1f, as shown in FIG. 2 or be inserted inside the collapsible tube.

With reference to FIG. 3, as explained hereinabove, irrigation catheter 1 is inserted into the proximal end of a working channel 3c of an endoscope 3e and advanced distally until the distal end of said catheter leaves the working channel and enters the colonic lumen.

FIG. 4A is a cross-sectional view of a simple irrigation tube 4b of the prior art, having a lumen 4c which diameter is approximately 1-3 mm, passing through a 3.8 mm diameter working channel 4d of a conventional colonoscope 4a shown is FIG. 4B. It will be seen that this non-collapsible catheter occupies a significant fraction of the available cross-sectional area (and hence volume) of the working channel 4b.

Figure 5B:
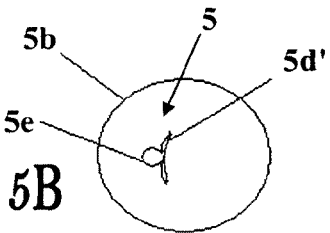

FIGS. 5A and 5B are cross-sectional views of an embodiment of the present invention showing collapsible tube 5d in its expanded form in FIG. 5A, and in FIG. 5B, in its collapsed state (5d'), connected to a relatively small diameter (e.g., ~0.25-0.6 mm) rigid metal wire 5e passing through a working channel 5b. FIG. 5A depicts catheter 5 in its expanded state, i.e. when irrigation fluid is pumped through the sheath, in order to cleanse the body cavity (e.g. colon). When negative pressure is applied to the proximal end of the sheath, it collapse and shrinks (5d'), as shown in FIG. 5B. For optimal collapsing a one way valve may be used.

In order to pump irrigation fluid into the sheath, the device may be connected to a positive pressure liquid pump (centrifugal, peristaltic or other) or to a manual injector. To cause collapse of the sheath, it can be connected to a manual injector or through a negative pressure vacuum pump.

An additional advantage of the present invention is that it permits the use of larger diameter irrigation catheters, thereby reducing the tubing resistance, thus enabling the use of an irrigation pump that generates a lower pressure, while maintaining the same water jet force.

Figure 6A:
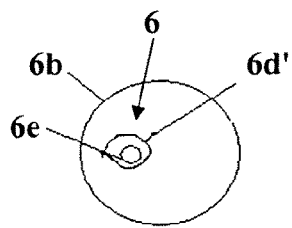
FIGS. 6A and 6B schematically illustrate cross-sectional views of an embodiment of the collapsible tube of the invention having an internally attached stiffening wire, where in FIG. 6A the tube is in a collapsed state and in FIG. 6B it is in an expanded state.
Figure 6B:
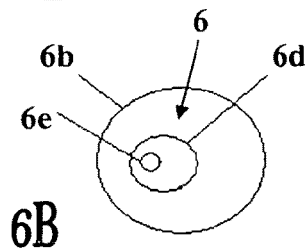

FIGS. 6A and 6B illustrate an alternative configuration, wherein the metal stiffening wire 6e (e.g., having a diameter of about 0.25 mm-0.6 mm) is located inside the collapsible sheath 6d (shown in FIG. 6A in a collapsed state—6d'), which in turn passes through working channel 6b. When irrigation fluid is pumped through the sheath under positive pressure, said fluid is directed to the body cavity that is being cleansed (e.g. the colon). Conversely, when a negative pressure source is connected to the proximal end of the device, the sheath collapses (6d' in FIG. 6A), thereby creating a larger free volume within the working channel 6b. In order to create optimal sheath collapse, a one way valve may be used.

The collapsible irrigation catheter 6 may be constructed from a non-compliant material such as nylon, Pebax (or a blend thereof), polyurethane and polyethylene terephthalate (PET). In such a case, the empty (i.e. evacuated) sheath has a random flat shape (6d'), which becomes circular (6d in FIG. 6B) in cross section when expanded with irrigation fluid. In another embodiment, the collapsible irrigation catheter may be made from a compliant material such as silicone or a thermoplastic elastomer (TPE), wherein said catheter is able to expands in the same manner as a compliant balloon Second Main Embodiment Multi-Lumen Collapsible Catheter The second embodiment similarly comprises a device suitable for passage through the working channel of an endoscope. However, in contradistinction to the first embodiment, described hereinabove, the device of this embodiment comprises a multi-lumen catheter tube, in which at least one wall of at least one of the lumens is collapsible. The multi-lumen tube is in fluid connection, via at least one of its lumens to a jet spray head located at the distal end of said tube. In one preferred embodiment, the multi-lumen tube is a bilumen tube, wherein one lumen is suitable for passing the irrigation liquid forward (i.e. in a distal direction) to the aforementioned jet spray head, while the second lumen may be used as a "virtual working channel", which may be used for a number of purposes, including aspiration and removal of fecal debris and the passage of endoscopic tools (such as: forceps, baskets, polypectomy devices, and so on).

Figure 7A:
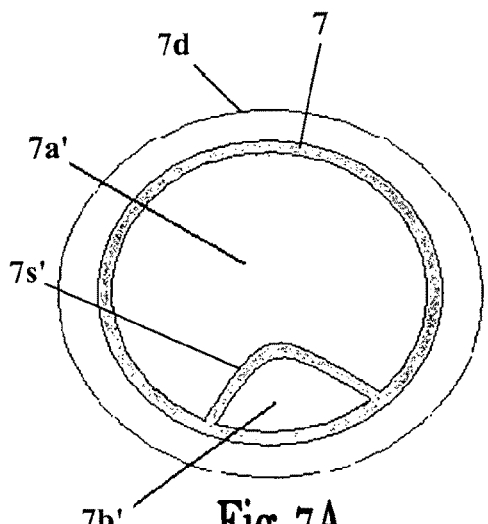
FIGS. 7A and 7B schematically illustrate cross-sectional views of a multi-lumen catheter having a collapsible internal wall, where in FIG. 7A the internal wall in a collapsed state and in FIG. 7B it is in an expanded state.
Figure 7B:
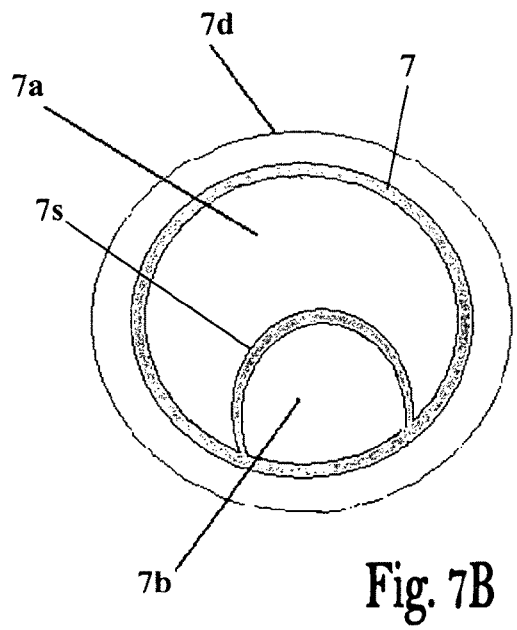

FIGS. 7A and 7B depict an exemplary preferred embodiment of a bilumen catheter tube 7 of the present invention. These figs. provide cross-sectional views of bilumen catheter 7 situated within the lumen of the working channel of a colonoscope 7d, wherein an internal wall 7s separates a larger "virtual working channel" (or aspiration lumen) lumen 7a, from a smaller irrigation lumen 7b. In FIG. 7B, the irrigation lumen 7b is shown in its expanded state, that is, while it is filled with irrigation fluid (such as saline). In FIG. 7A, the irrigation lumen is shown in its collapsed state (7b') after the irrigation fluid has been removed from said lumen, by means of a negative pressure source which has been connected to its proximal end. It may be seen from FIG. 7A that when the irrigation lumen 7b' is in its collapsed state, internal wall is shrunk (7s') and the larger aspiration (or "virtual working channel") lumen 7a' has a significantly larger volume, thereby permitting said lumen to fulfill its intended functions (aspiration and/or passage of surgical tools) with greater efficiency.

In one preferred embodiment, the collapsible wall(s) of the multi-lumen conduit may be constructed of a flexible, non-compliant material (e.g. Nylon or Pebax). Alternatively, said collapsible wall(s) may be made of a compliant material such as silicone rubber.

Figure 8:
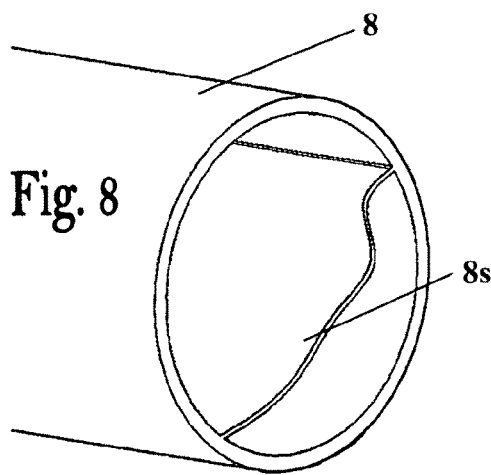
FIG. 8 schematically illustrates a perspective view of a bilumen embodiment with a partly-collapsed state internal wall.

A perspective view of the bilumen embodiment 8, with the irrigation lumen internal wall 8s in a partly-collapsed state, is shown in FIG. 8.

Figure 9:
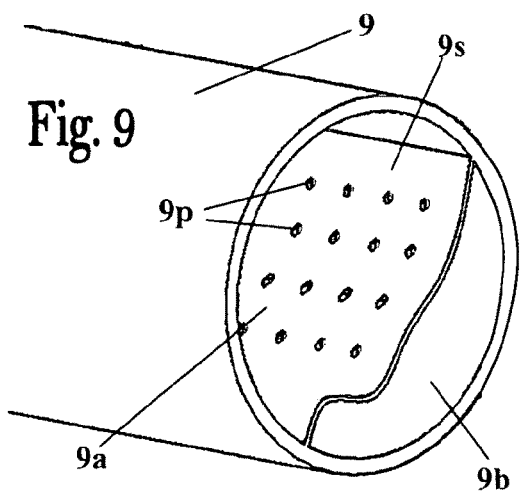
FIG. 9 schematically illustrates a perspective view of a bilumen embodiment with a partly-collapsed state internal wall, wherein said wall is perforated by a series of apertures.

An alternative embodiment of a bilumen catheter 9 of the present invention, in which the internal wall 9s of the irrigation lumen (also referred to as the bilumen partition) is perforated by a series of apertures 9p, is depicted in FIG. 9. Apertures 9p permit the passage of a portion of the irrigation fluid from the smaller, irrigation lumen 9b into the larger aspiration lumen 9a. The irrigation fluid which streams through apertures 9p will assist in the breakdown of fecal material which has been aspirated into aspiration lumen 9a. This further breakdown of particulate matter will inter alia assist in preventing blockages of aspiration lumen 9a and the negative pressure line and apparatus connected at the proximal end thereof.

The multi-lumen catheter tubes of the present invention may be produced by means of incorporating internal partitions within a single tube, or alternatively, by connecting two or more single lumen tubes in a side-by-side manner.

Control of Distal Jet Spray

In addition to providing externally-collapsible conduits (first main embodiment) or internally-collapsible conduits (second main embodiment), for the purpose of allowing expansion of the aspiration (or virtual working channel) lumen, the present invention also provides various novel solutions for the control of the irrigation jet spray through the distal spray head and the portion of the catheter that is located immediately proximal to said distal spray head.

FIG. 10A schematically depicts the distal spray head region of one preferred embodiment of the invention. Whilst generally similar to the first main embodiment of the invention described hereinabove (and illustrated in FIG. 1-6), the presently-described embodiment also comprises a number of additional features. Thus, referring to FIG. 10A, the distal spray head g1 may be seen comprising a plurality of spray nozzles g3 in its distal part. The rigid wire g6 differs from that described hereinabove, in that in the presently-described embodiment, wire g6 has an internal lumen which is in fluid contact at its distal extremity with a balloon g2, and is in fluid contact at its proximal extremity with a source of inflation fluid and a pumping apparatus (not shown). Adjoining the distal head on its proximal side is a sleeve g7 fitted with a series of lateral apertures g4. The collapsible catheter sheath g10 is affixed to sleeve g7 with a biocompatible glue (e.g. UV glue) and further mechanically affixed with a pressure ring (g5). Thus, when it is desired to direct the jet spray in a forward (distal) direction, the balloon g2 is left in its non-inflated state, thereby permitting free flow of irrigation fluid through both the distal spray nozzles g3 and the lateral apertures g4, as shown in FIG. 10A.

However, when the operator desires the jet spray to exit via the lateral apertures g4 only, the balloon g2 is inflated such that it blocks the distal jet apertures g3, as shown in FIG. 10B. The operator may choose to pump irrigation fluid distally through the catheter for a prolonged period with occasional inflation or deflation of balloon g2, in order to direct the fluid as required. Alternatively, during the irrigation the balloon may be inflated/deflated at a high frequency (for example ~10-20 Hz) thereby enabling the irrigation fluid to apply a vibration force, thus enhancing the cleansing operation.

In a further preferred embodiment, the device of the invention further comprises means for blocking the lateral apertures described hereinabove, thus allowing the operator to either permit or prevent an irrigation fluid jet spray exiting said lateral apertures. These means may be used in conjunction with the above-described balloon element, thereby permitting the selection of jet spray through:
  i. distal spray nozzles only;
  ii. distal spray nozzles and lateral apertures; or
  iii. lateral apertures only.

Alternatively, the device may comprise the lateral blocking means only, that is, the aforementioned balloon element is not incorporated therein.

In one preferred embodiment, the lateral aperture blocking means comprise a slideable overtube (11t) assembled around the catheter tube (11c) in the region of the lateral apertures (11p). FIGS. 11A to 11C schematically illustrate three different positions of this overtube 11t in relation to apertures 11p. Thus, in FIG. 11A, overtube 11t is in its proximal-most position, thereby exposing all of the lateral apertures 11p, and thus permitting the jet spray to leave the side of the distal portion of the catheter tube. In FIG. 11B, overtube 11t has been moved such that it partially covers the side apertures 11p, thereby reducing the area of the distal part of the catheter which is available for emitting a jet spray. Finally, in FIG. 11C, overtube 11t has been drawn into its distal-most position, thereby completely blocking all of the lateral apertures 11p.

Figures 12A, 12B, 12C:
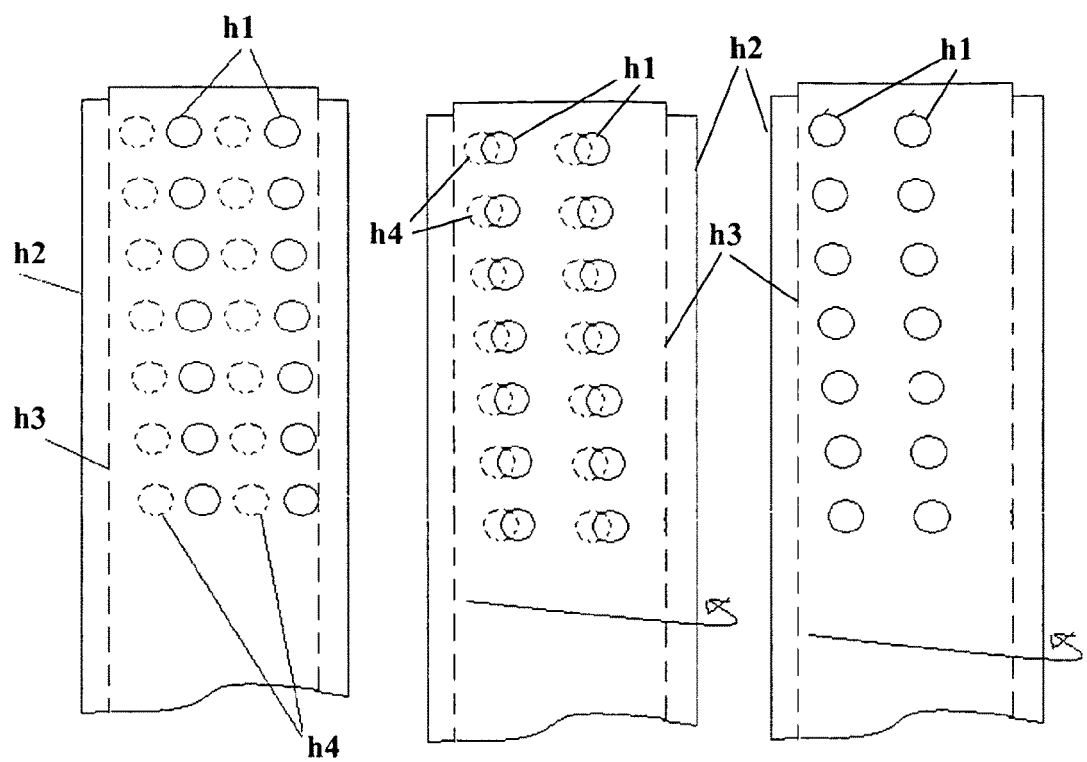
FIGS. 12A to 12C schematically illustrate a distal spray head embodiment employing a rotatable overtube for controlling the jet spray in a misaligned state in FIG. 12A, in a partially overlapping state in FIG. 12B, and in a precise alignment state in FIG. 12C.

In an alternative embodiment, as shown in FIGS. 12A to 12C, a rotatable (rather than slideable) overtube h2 is fitted with its own series of lateral apertures h4 corresponding exactly to apertures h1 present in the catheter tube h3. Thus, in FIG. 12A, the rotatable overtube h2 is positioned such that the apertures h1 therein are located such that they are not in alignment with the lateral apertures h4 of catheter tube h3, thereby preventing any jet spray from leaving said lateral apertures h1. In FIG. 12B, however, the overtube h2 has been rotated into an intermediate position, such that the two sets of apertures, h1 and h4, partially overlap, leading to a series of reduced-area jet spray channels. Finally, FIG. 12C illustrates the situation after overtube h2 has been rotated further, such that the apertures h1 therein are in precise alignment with the lateral apertures (h4, not shown) of the catheter tube h3, thereby permitting the maximal volume of jet spray through said apertures.

One of the key advantages offered by the nozzle-blocking mechanisms described hereinabove is that aspiration and irrigation operations may be performed independently (together or separately), thus enabling flexibility and higher efficiency of liquid usage. Consequently:

When it is required to irrigate the colon it is desirable that there should be the maximal momentum of flow passing through the distal spray head. In such a case, the lateral apertures would be blocked.

When it is required to aspirate the fecal material through the working channel it is desirable that the spray jets be focused sideways, in order to effect maximal fecal breakdown and dilution while passing through the working channel.

It should be noted that the aspiration and dilution of fecal material using the lateral apertures may be done continuously (aspirating diluted/broken down feces while the lateral apertures are exposed and functioning with the catheter sleeve in its 'inflated' state). Alternatively, it is possible to switch between aspiration and lateral aperture spray, such that each time aspirate is performed, the catheter sleeve collapses (due to the application of internal negative pressure) and then inflated again in order to cause fecal breakdown. This process is then repeated until the desired result is obtained.

In other preferred embodiments of the present invention the following two configurations may be used either separately or together, in order to increase the efficiency of aspiration of broken-down fecal material:

1) Using jet sprays emanating from the lateral apertures for breaking down the feces that have been aspirated through the working channel.
2) Using a spring-like configuration made of thin mesh wires that employ a high frequency 20-50 Hz linear movement to dismantle the feces in a manner similar to that of a food processor.

Figure 13:
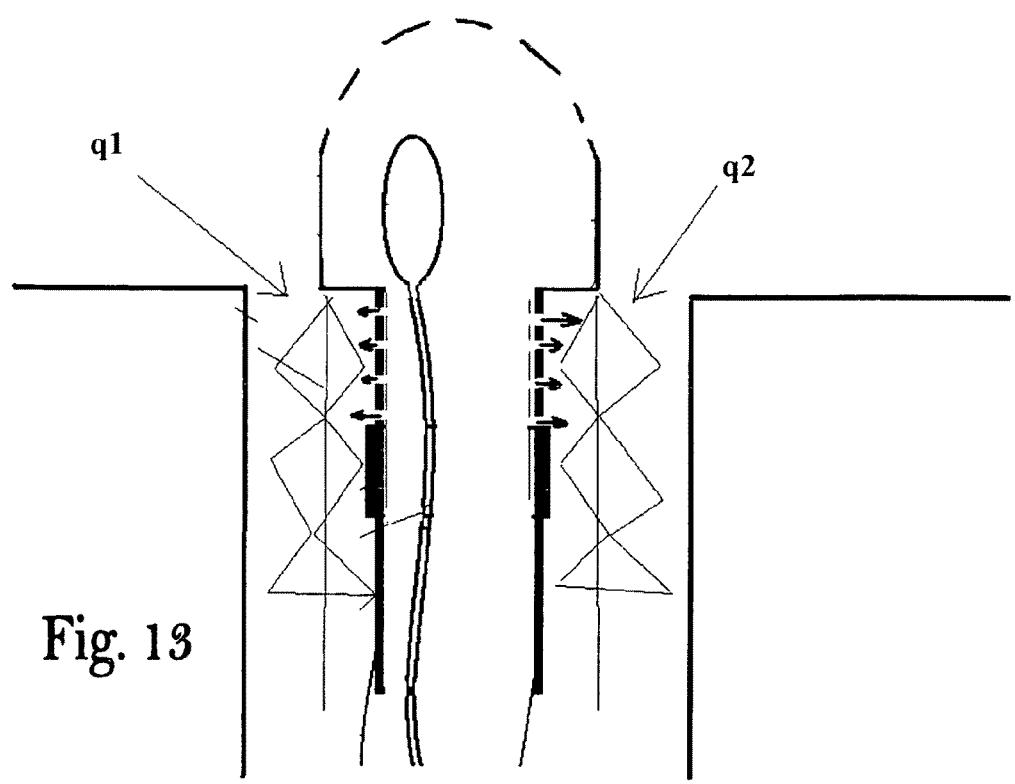
FIG. 13 schematically illustrates a distal spray head embodiment of the invention utilizing dismantle springs.

The second of the above two configuration is illustrated schematically in FIG. 13 showing a possible embodiment employing spring-like thin mesh wires q1 and q2.

The present invention also encompasses distal spray head units that are capable of directing the flow of irrigation fluid, either inwardly or outwardly:

Inward Direction of Flow

The configuration illustrated in FIGS. 14A to 14D may be used to direct the flow of irrigation fluid out of the distal spray head p4 in a predefined convergent (i.e. inwardly-pointing) direction. The flow p6 may pass through an optimization entrance p3 to avoid local turbulences. It then passes through a fine nozzle p1 (e.g., having a diameter of about 0.2-0.4 mm) and finally exits spray head P4 by flowing across the surface of nipple p2 using the tension surface principle. Substantially all of the irrigation fluid is thus directed inwardly toward a focusing point p5.

In an alternative configuration, as shown in FIG. 15, the flow p6 may be directed by means of a pre-set internal nozzle angle p7.

Outward Direction of Flow

The configuration shown in FIGS. 16A to 16D may be utilized to direct the flow out of the distal spray head y4 in a divergent manner. The flow y6 may pass trough an optimization entrance y3 designed to avoid local turbulences. It then passes through a fine nozzle y2 (e.g., having a diameter of about 0.2-0.4 mm) and finally exits spray head y4 by flowing across the surface of nipple y1 using tension surface principle. As shown in FIG. 16D, substantially all of the irrigation fluid is thus directed in a divergent manner.

In an alternative configuration, as shown in FIG. 17, the flow y6 may be directed by means of a pre-set internal nozzle angle y8.

Figure 18:
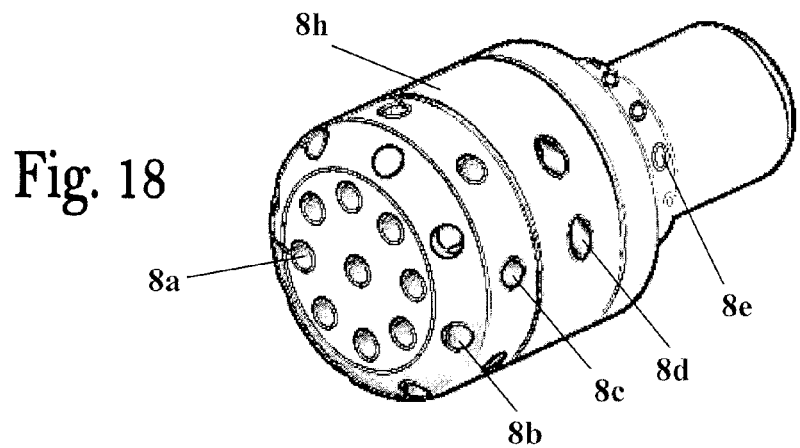
FIG. 18 shows a perspective view of one preferred embodiment of a distal spray head of the invention.

FIG. 18 depicts one preferred embodiment of a distal spray head $8h$ that may be used as part of the present invention. This particular version of the spray head comprises a combination of jet spray apertures ($8a$, $8b$, $8c$, $8d$, $8e$) located at different points along the surface of the head, and angled at various directions. The apertures and nozzles labeled in the figure are as follows:

A. Forward-pointing jets (via apertures $8a$) to cleanse the colonic lumen (or other body cavity) distal to the leading edge of the device;
B. Jet nozzles $8b$ directed at an angle other than 90 degrees to the distal face of the device (e.g. angled out toward the colonic wall);
C. Radially outward-pointing jets $8c$;
D. The force of the irrigation water provides sufficient force to cause a ring comprising slanted apertures $8d$ to rotate and thus propel the washing liquids radially;
E. Backward-pointing jets (via apertures $8e$) either for device advancement or for breaking up fecal material just before it is aspirated through the working channel and/or cleansing the endoscope lens and illumination LEDs.

Filtering and Breakdown/Dilution of Fecal Material

Figure 19A:
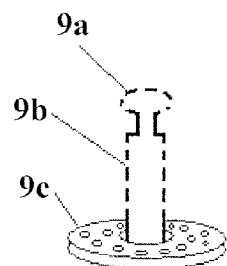
Figure 19B:
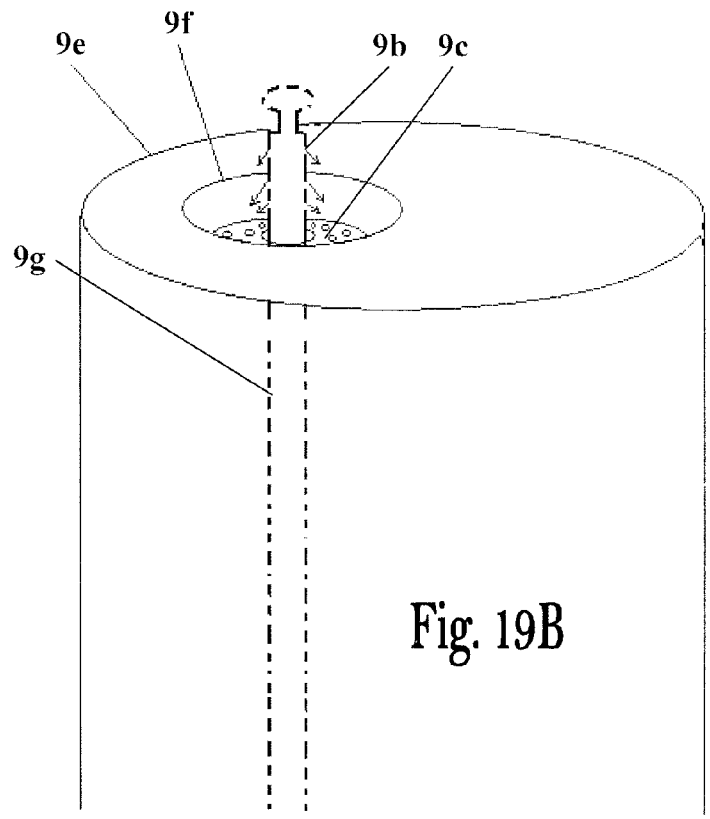

In another preferred embodiment, as depicted in FIGS. 19A and 193, the device may further comprise a filter unit $9c$ which is assembled on the distal part of catheter tube $9g$. Filter $9c$ is capable of blocking any material that is larger than the filter pore size. Using the lateral apertures $9b$, which may be directed backwards, the feces that arrive to the filter are broken down until they are sufficiently diluted such that they are able to pass through the filter pores with the assistance of negative pressure applied at the proximal end of the working channel $9f$ of colonoscope $9e$.

Further Technical Features

In an additional configuration, the rigid wire disclosed hereinabove may have an internal lumen (as described in the context of the embodiment fitted with a distal balloon). In this particular embodiment, said wire lumen may be used to insert air into the distal spray head, thereby enabling a mixture of air and irrigation fluid to be used for cleansing the colon or other body cavity.

In yet another embodiment of the device nozzles or apertures are located along at least the distal 2-5 cm, or alternatively along the entire length of the tube. The presence of such nozzles permit:

the insertion and maneuverability of the device through the colon and working channel;
self propelling navigation through the colon or other body cavity;
Internal working channel cleansing, i.e. causing breakdown of fecal material that was aspirated into the working channel and may potentially obstruct the aspiration channel.

In a still further embodiment, the device may comprise an asymmetric collapsible tube which, when inflated with water, is capable of pushing the fecal material that is still inside the working channel outwards by a peristaltic force. Such a working arrangement may be achieved either by inflating the tube one sections at a time (in ~1 cm sections, for example) from the distal part to the proximal part of the colonoscope.

In a yet further embodiment, the device may be inflated/deflated in such a way that it is capable of applying a peristaltic force onto the internal wall of the colonoscope working channel, thereby assisting the breakdown of the remaining fecal material inside the working channel.

In a still further embodiment of the invention, the device may further comprise an additional, parallel, lumen running along the length of the collapsible catheter sheath. This additional lumen may be used for a number of purposes including: injection of therapeutic agents, injection of iodine (for chromo-endoscopy), application of very cold water in order to arrest bleeding, and delivery of tumor-specific bio-markers. In addition, the extra lumen may be used to introduce air for insufflation of air mixture with the irrigation fluid. It is to be noted that the additional lumen may have a very small diameter (e.g. 0.2-1 mm) and may be contained within a collapsible tube.

In one alternative embodiment, the distal spray head unit described above may be connected to a flexible tube that does not change its diameter under the liquid pressure (i.e. it is non-collapsible). Such a configuration may be advantageous when it is required mainly to irrigate a specific location without necessarily allocating more space to the working channel. This configuration may also be advantageously employed in situations wherein the space between the working channel and the lumen of the irrigation water is sufficiently large to allow aspiration and/or insertion of additional tooling through the working channel. This particular embodiment, while employing a conventional catheter tube is characterized by the following notable features:

- Miniaturization of the distal spray head unit to 2-3 mm overall diameter enables insertion through small lumens such as the working channel of a colonoscope.
- The irrigation fluid is directed through the distal spray head cap assembled on the distal part of the tube and through holes in the tube.
- It is required to design specific nozzles to optimize the pressure flow and avoid turbulences wherever possible.
- The invention apparatuses described above are intended to enable MAXIMUM LIQUID MOMENTUM WITH MINIMAL LIQUID VOLUME. For example, if the irrigation liquid is transformed to a spray wherein the liquid drops are very small no cleansing effects can be achieved. Alternatively, if the nozzle is too large (e.g. 0.8 mm-3.8 mm) to provide the cleansing momentum required for irrigation an impractically-large volume of irrigation fluid will be required.
- The irrigation nozzles are focused forward (in an inward, outward angles or straight), thus enabling the physician maximum efficiency and maximum effective force (liquid momentum) in the direction where the colonoscope camera is directed.
- Automatic cleansing in 360° to enable irrigation where no vision is available (for example, out of the FOV or in diverticulosis).

Distal Plug-Guidewire Approach:

As explained above, the present invention aims to provide means and techniques for supplying cleaning fluid to a spray head or nozzle situated at the distal end of an endoscope working channel, at a pressure that is sufficiently high in order to permit generation of a jet spray that will allow efficient cleaning of the colon or other body cavity which lies distally to the distal end of said endoscope without causing trauma and tissue injury. The key technical problem that needs to be solved in fulfilling this aim is the generation of a sufficiently high pressure head in order that a jet spray may be formed, without the need for a separate catheter to supply the irrigation fluid to the spray head. As explained hereinabove, the use of such fluid-supply catheters within the working channel is undesirable, since the presence of such a catheter reduces the working channel cross section and volume which are required for aspiration of solids and liquids and increase the friction surface.

The solutions provided by these embodiments of the present invention further comprise, in their most general form, a distal spray head unit or plug which is mounted on a thin guidewire (e.g., having a diameter of about 0.3-0.8 mm) or (in some embodiments) a very small diameter tube (e.g., having a diameter of about 0.4-1.5 mm). This spray head effectively functions as a perforated plug that may be caused to partially or completely block the distal exit of the working channel. Thus, when partially blocking said distal exit, irrigation fluid is supplied through the working channel, said fluid being caused to exit the spray head at a higher pressure, in the form of a jet scatter directed towards the region of the body cavity (e.g. colon) located immediately distal to the distal end of said working channel.

The irrigation fluid may be supplied to the spray head unit in the following manner: the irrigation fluids fed into the endoscope working channel using a positive pressure water pump (peristaltic, centrifugal pump, dosing pump, gearwheel pump, etc.) at a pump outlet pressure of between 2 and 10 atmospheres, resulting in a pressure range of 2-8 atm in the outlet nozzle. The flow rate may range between 0.2 and 2 l/min. Sealing elements, adaptors and connectors using standard Luer components may be used. It is to be emphasized that the abovementioned pressure and flow parameters are for the purpose of illustration only, and do not limit the invention in any way.

It is to be noted that throughout the disclosure and description of the distal head-guidewire solution, the terms "distal plug", "distal head spray unit" and the like are used interchangeably.

A typical arrangement is shown in FIG. 31, illustrating endoscope 31*f* having a working channel 31*g* into which the cleansing device 31*k* of the invention is introduced via endoscope port 31*e*. Cleansing device 31*k* comprises guidewire/tube 31*j* having a distal head 31*i* attached at its distal end and a proximal handle 31*a* to which the proximal end of the guidewire/tube 31*j* is attached. Guidewire/tube 31*j* passes through a tube 31*t* attached to proximal handle 31*a* and which is capable of being sealably connected to endoscope port 31*e*. Tube 31*t* comprises irrigation ports 31*b* and 31*c* for supplying irrigation fluid into working channel 31*g* therethrough, and aspiration port 31*d* to which a vacuum pump may be connected. As will be discussed in details herein later, proximal handle 31*a* advantageously comprises control mechanism capable of setting several working states (designated by letters A, B and C) of the endoscope/cleansing device assembly (31*f*/31*k*).

In order to fulfill this function, the distal plug is constructed such that it may be caused to move between the following two conformations:

a) A first conformation, wherein the spray head unit has a size that permits its distal passage through the working channel prior to irrigation and aspiration, and its proximal passage following the end of those procedures. This conformation is also used for sealing the distal exit of the working channel, such that it may assist in cleansing the endoscope working channel utilizing a partial length tube or sleeve (the distal end of which ends a few centimeters from the distal end of the guidewire) to supply high pressure irrigation fluid to the distal part of the endoscope working channel. In this way, positive hydrostatic pressure forces are added to the vacuum pressure, thereby significantly increasing the efficiency with which particulate matter may be moved proximally from the distal end of the working channel and thus preventing and/or clearing blockages therein. Generally, this first conformation is adopted when the device is contained within the confines of the endoscope working channel (other narrow instrument channel). The external diameter of the distal plug is generally constructed to be only slightly larger (by a few millimeters) than the internal diameter of the working channel, such that when said plug is contained within the channel, its outer diameter becomes reduced, and the previously open channels and apertures in the plug become closed.

b) a second conformation, wherein the spray head unit has larger external dimensions than in the first position. This occurs when the spray head unit (distal plug) leaves the confines of the working channel (at its distal end). A proximally-directed force is then applied such that the distal plug makes contact with the distal exit of the working channel, effectively providing a fluid seal over said exit, such that the only fluid transfer between the working channel and the region of the body cavity located beyond the distal end thereof is by way of channels, apertures and/or nozzles formed within said spray head unit;

All of the abovementioned conformations may be incorporated into one device.

In use, the spray head unit, while in its second, expanded conformation may be moved distally from its seated position over the working channel exit (as described immediately hereinabove) such that free fluid transfer between said working channel and the region of the body cavity located beyond the distal end thereof is once again possible. In this state, the working channel may be employed as a suction channel for the aspiration of fluid and solid debris from the body cavity, as well as for the passage of endoscopic tools.

It is to be emphasized that the potential use of the working channel as an aspiration channel is facilitated by the fact that the spray head unit is mounted on the aforementioned very small diameter wire or tube made of either metal or plastic resin), rather than on a fluid-supply catheter that would occupy a correspondingly larger fraction of the available working channel volume. This wire or small diameter tube is sufficiently rigid that it allows the operator to advance the distal plug through the working channel and out into the body passage lumen. However, it also needs to be sufficiently flexible in order to negotiate bends and convolutions within said body passage. is to The present invention also overcomes another problem of the latter device, namely that a fluid-supply catheter having a very small diameter would require the use of a much higher pressure pump than is currently used, due to the high resistance.

The presently-disclosed device may also be used to fulfill the second of the principle aims of the present invention that were mentioned hereinabove, namely irrigation and cleansing of the working channel of an endoscopic instrument, in a manner such that blockages of said channel by fecal material may be prevented or removed. Thus, whenever the working channel becomes blocked by feces (and/or other solid and semi-solid material), or alternatively before it is thus blocked, a spray head unit, of the present invention (as will be described in more detail hereinbelow) is mounted on a flexible wire, which in turn passes through a hollow tube through which irrigation fluid can pass. This tube may have side apertures formed along its entire length or a portion thereof and/or an aperture at the distal end. As an alternative to the above-described wire within tube assembly, an additional embodiment comprising a hollow wire or thin tube having side apertures formed along either its entire length or a portion thereof and/or aperture at the distal end, may also be used. A cleaning fluid (such as water or a special dissolving solution) is pumped or injected into the proximal end of the hollow wire/tube such that said fluid is caused to exit through the apertures, thereby causing reduction in the size of the solid debris. In the case of large obstructions caused by the accumulation of solid material within the working channel, the distal spray unit head can be repeatedly advanced (either manually or automatically) and retracted, thereby making a mechanical contribution to the breakup of said obstruction. The combination of this mechanical effect and the fluid spray thereby permits the effective removal of solid material that may otherwise obstruct the working channel.

In addition to the fluid causing reduction in the size of the solid debris an additional usage of the fluid is to create a positive hydrostatic pressure force (e.g. between 3 and 8 atm) in order to help push the feces and blockage backwards, in addition to the vacuum force which is limited to a maximum of −1 atm of pressure. In practice, the vacuum pressure actually achieved at the distal part of the endoscope may be much less than −1 atm. In this configuration it is necessary to seal the distal end of the endoscope.

In another particularly preferred embodiment of the present invention, the above-defined aim of preventing or disrupting blockages within the working channel during use of the presently-disclosed device is achieved using a version of said device in which the guidewire, for most (but not all) of its length passes through a partial-length tube or sheath. The proximal end of said partial-length tube is fixed within a proximal handle (as will be described in more detail hereinbelow). The distal end of the partial-length tube ends a few centimeters before (i.e. proximal to) the distal end of the guidewire, to which is affixed a distal head spray unit of the present invention. While any of the distal head spray units that will be described hereinbelow may be used to implement this particularly preferred embodiment, the spray head referred to as the "second spray head unit embodiment" is especially suitable.

As disclosed hereinabove, in one preferred embodiment, the distal plug-guidewire device of the present invention may further comprise an outer tube that is arranged such that it surrounds both the inner tube and guidewire in a co-axial manner. The presence of this outer tube confers a number of distinct advantages on the cleansing device, all of which will be described in more detail hereinbelow. One of the most important of these advantages is the fact that, functionally, the outer tube may be considered to replace the endoscopic working channel in which the above-disclosed embodiments are contained when in use. Thus, the presence of the outer tube enables the cleansing device described herein to function either within the working channel (or any other instrumental lumen) or within a naturally-occurring channel or passageway (such as the colonic lumen). Thus, while for the sake of convenience, much of the detailed description of this embodiment (hereinbelow) assumes that the device of the present invention is to be placed within an endoscope working channel, it is to be recognized that said device may equally be used directly in a natural body passageway, such as the colon.

The additional outer tube defined hereinabove provides the colonic cleansing device with the following additional advantages:

- A stand alone configuration which permits the use of the device in any lumen (natural or instrumental) including endoscopic working channels.
- The device may extend beyond the distal end of the working channel and/or other natural or instrumental lumen.
- A camera may be included on the outer tube and it will enable to view further areas while performing the cleansing.
- Aspiration and irrigation will be done through the gap between the outer tube and the inner tube
- The outer tube may be constructed such that it has a flexible, semi rigid or rigid configuration.

Since (as will be described) the distal-proximal location of the distal end of the guidewire is altered during use, while the position of the partial-length tube is fixed (with reference to the proximal handle), the precise distance between the distal end of the partial-length tube and the more distally placed distal end of the guidewire will also alter, and will generally be in the range of about 1 cm to about 4 cm. In general, the total length of the guidewire (which is typically constructed of 0.5-0.6 mm diameter) will be in the range of about 150 cm-210 cm, depending on the endoscope length used as well as the external extension tubing length. Extension tubing is assembled between the endoscope working channel adaptor and the handheld device, typically having a length of 50-70 cm with an internal diameter of similar to the working channel diameter (commonly 3.8 mm). The distal end of the guidewire is attached to the distal spray head unit by means of glueing, bonding or laser welding/soldering of the metal guide wire and the distal plug. The partial-length tube is generally constructed of PTFE tubing (for low friction) or ETFE, depending on the sterilization method of the device to be used, and has an external diameter of about 1-mm-1.6 mm and a wall thickness of about 0.25 mm. It is to be recognized, however, that these measurements are given only as a general guide and do not limit the scope of the present invention in any way.

In some embodiments of this version of the device, said device incorporates means for assisting the operator to recognize and detect the position of the distal spray head during use. In one such embodiment, one half of a ratchet mechanism is fitted to the distal face of the endoscope adjoining the distal exit of the working channel. A complementary ratchet surface is incorporated into the proximal face of the spray head unit, such that when said unit is brought into contact with the distal exit of the working channel a clicking sound (caused by the ratchet mechanism) is emitted, thus informing the operator that the distal head unit is in close apposition with the endoscope distal face. Other embodiments incorporate different mechanisms for signaling the position of the distal head, including remote sensors or transmitters located on the distal face of the endoscope that communicate with receivers or transmitters located on the proximal handle.

Figure 32A:
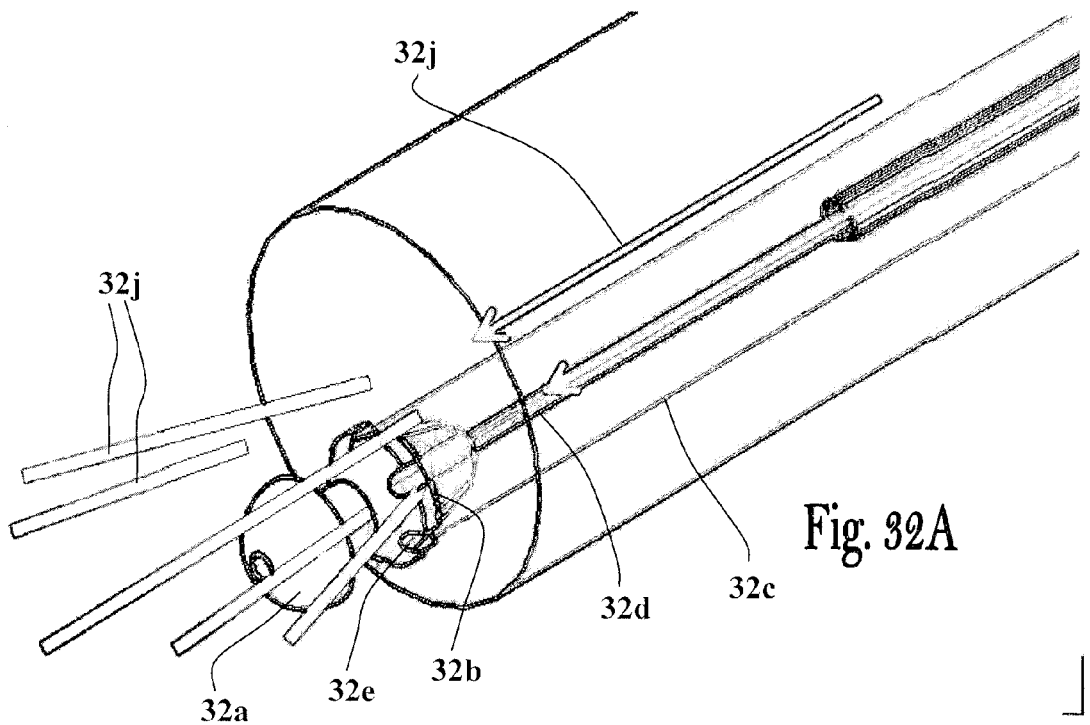
Figure 32B:
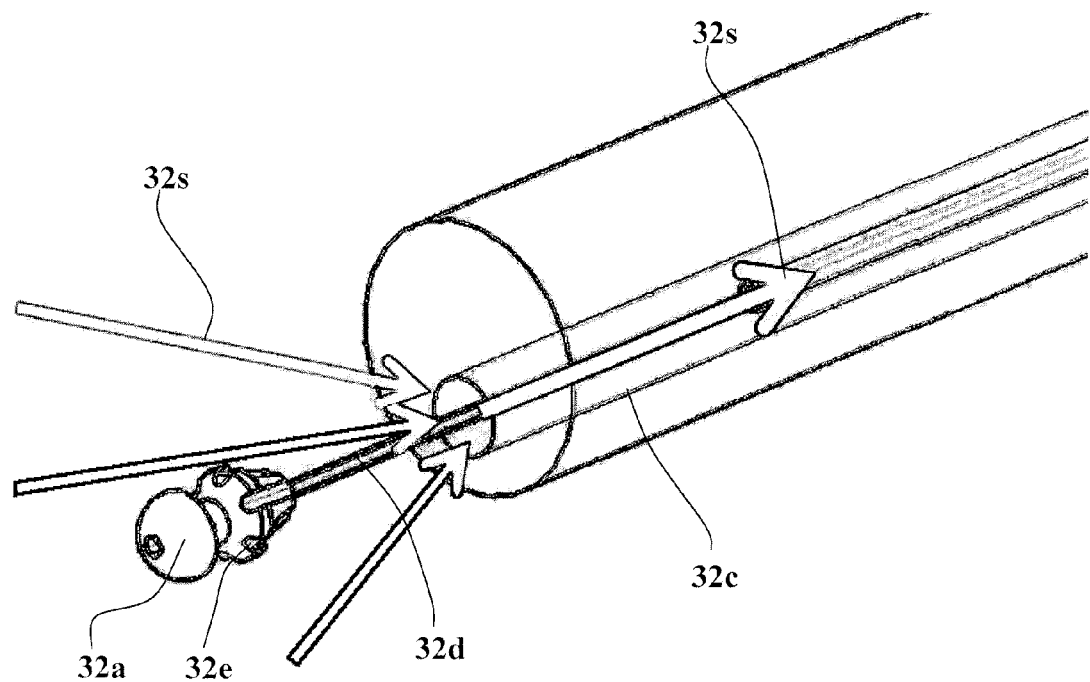

This particularly preferred embodiment of the device of the present invention is illustrated in FIGS. 32A to 32C. Thus, FIG. 32A depicts the distal spray unit 32a (mounted on guidewire 32d) located in the distal exit 32b of the colonoscope working channel 32c. Irrigation of the colonic lumen is achieved by passing the irrigation fluid through the working channel 32c. The irrigation jets (32j) pass through spray nozzle apertures 32e located between the spray head unit 32a and the working channel circumference (32b).

In FIG. 32B, the spray head unit 32a is located outside of the working channel 32c enabling free aspiration (32s) of irrigation liquid and solid and semi-solid debris through the large space that exists between the guidewire (or tube) 32d and the working channel 32c.

FIG. 32C depicts the manner in which the nozzle seals the endoscope working channel 32c to enable the fluid pressure force coming from the irrigation fluid that is diverted distally through the lumen of the partial length sleeve 32i to actively push the liquids and fecal remains in a distal-to-proximal direction through the lumen of the working channel 32c, between the partial length tube 32i and the inner wall of the working channel.

In order to move between the three different operational modes of this particularly preferred embodiment of the device (i.e. irrigation, aspiration and working channel clearing), it has been found most convenient to incorporate a dedicated proximal handle into the device, whereby the operator is able to adjust the mode of operation by means of operating manual controls that cause change in the position of the distal spray head unit as well as the path by which the irrigation fluid is brought to the distal end of the device. Details of a suitable device will be described hereinbelow and illustrated in FIGS. 40A and 40B.

Figure 41:
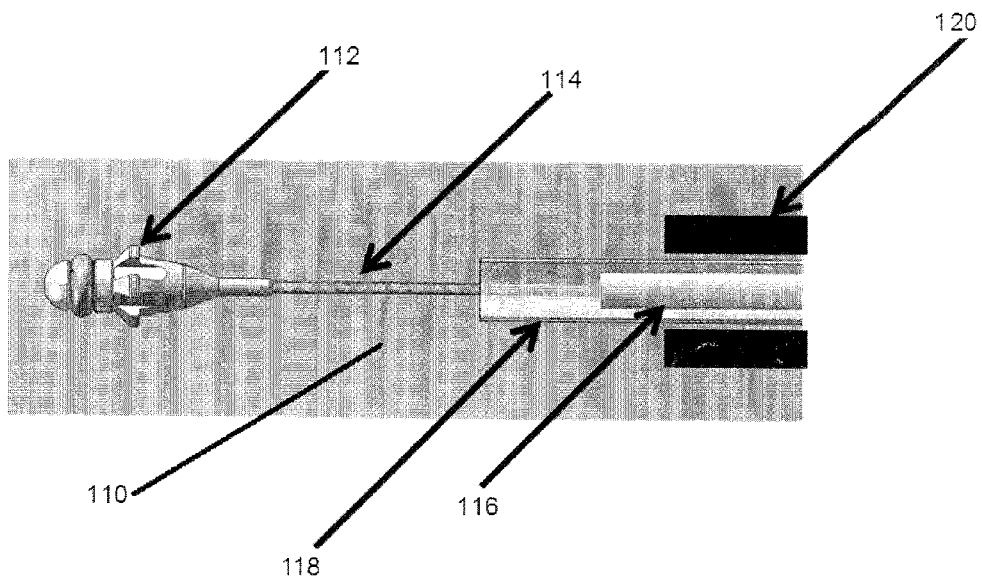
FIG. 41 illustrates an embodiment of the device of the present invention that further comprises an outer tube.

As disclosed hereinabove, in another preferred embodiment, the device of the present invention may further comprise an outer tube or sleeve that surrounds both the inner tube and guidewire in a coaxial manner. A typical example of the device of the present invention 110 is depicted in FIG. 41. A distal spray head 112 is shown mounted on a flexible guidewire 114, which in turn is disposed coaxially (and movably) within the lumen of partial length inner tube 116. Said inner tube is enclosed by outer tube 118, which itself is partially contained within the lumen of an endoscope working channel 120 or some other instrumental or natural lumen. It is to be noted that in the event that the device is to be used in an endoscope working channel (or similar instrumental lumen), an attachment seal is inserted around the device at the proximal entrance to said working channel. This sealing element, which may be constructed of a flexible material such a biocompatible rubber, plastics or metal, prevents irrigation and debris being sprayed on the operator. In addition, its presence is necessary for maintaining integrity of the negative aspiration pressure that is applied to the space between the inner and outer tubes of the device.

The presence of the above-described outer tube in the device of the present invention results in liquid and debris aspiration taking place through said device (in the space between the inner and outer tubes) rather than through the working channel itself. This arrangement therefore requires the inclusion of a Y-connector at the proximal end of the working channel, in order to direct the aspirated liquid and solid material—via a one-way valve—along a waste line to a collection container.

The spray head unit of the present invention is capable of being moved between the various above-described conformations by virtue of possessing one or more structural or functional features that permit the dimensions of the head unit to be altered by the operator, for example, by using linear shift of the head unit from inside the endoscope working channel to outside and vice versa. The present invention, is not, however, limited to such a mechanism but rather encompasses further embodiments that may include other mechanical mechanism or inflatable mechanisms that can be used to alter the spray head conformation and the use of flexible resin silicone or rubbers.

Several different embodiments of the distal spray head unit will now be described. It is to be recognized, however, that there may be many other structural variants which may fulfill the functional requirements set out hereinabove, and that said variants are equally considered to be within the scope of the present invention.

First Spray Head Unit Embodiment

Figure 20A:
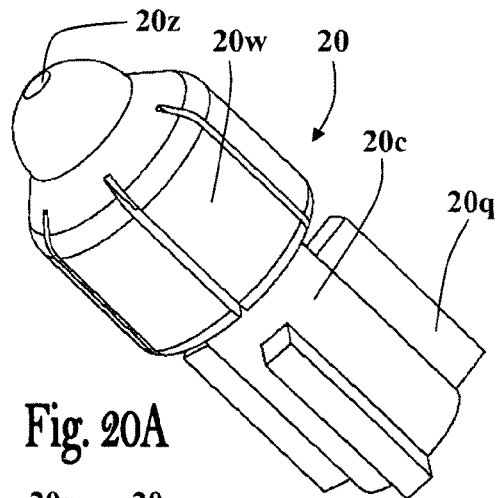
Figure 20B:
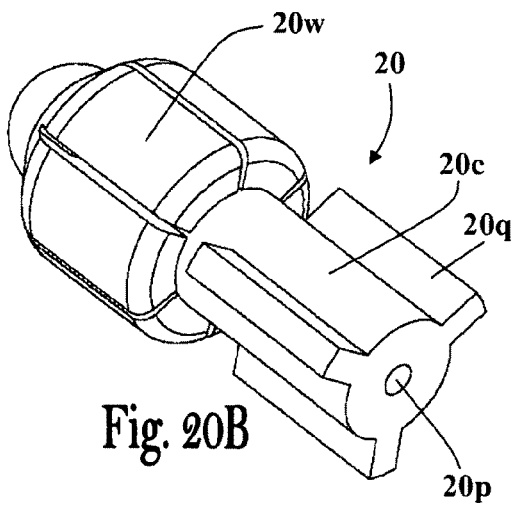
Figure 21A:
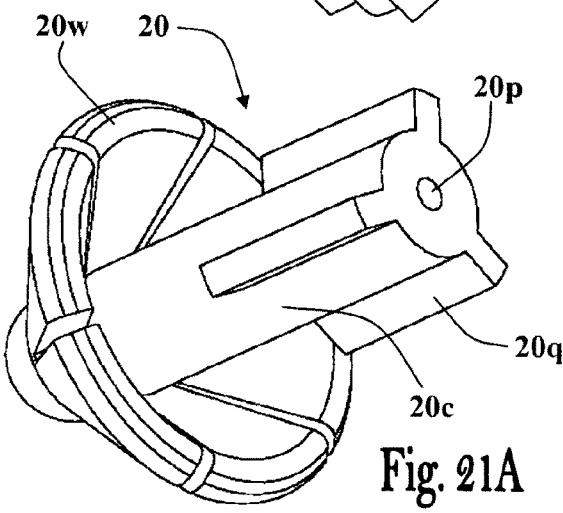
Figure 21B:
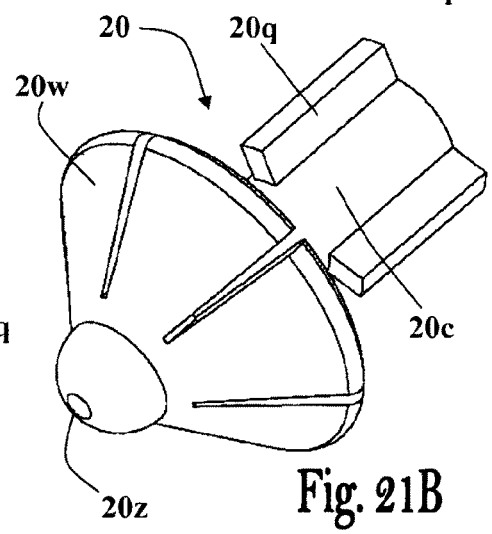
Figure 22A:
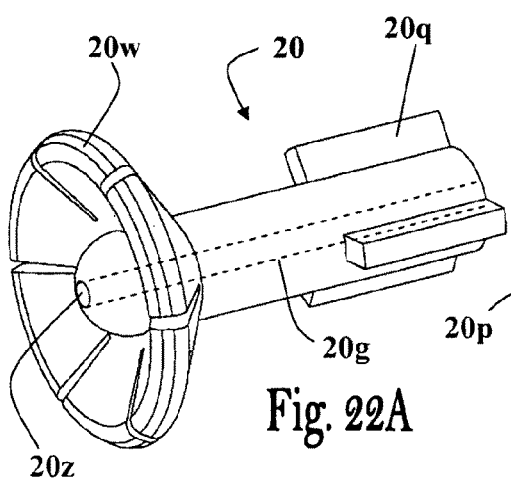
Figure 22B:
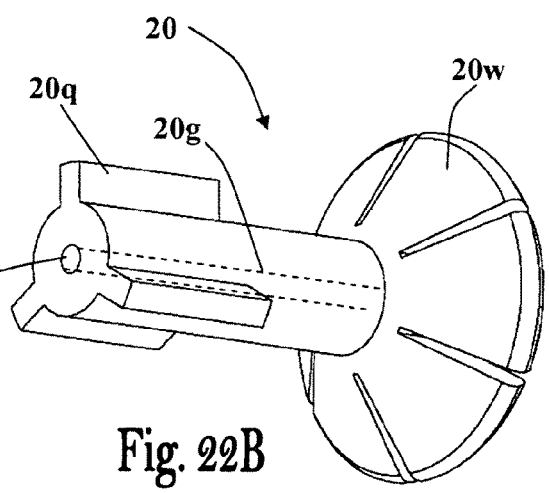
Figure 26:
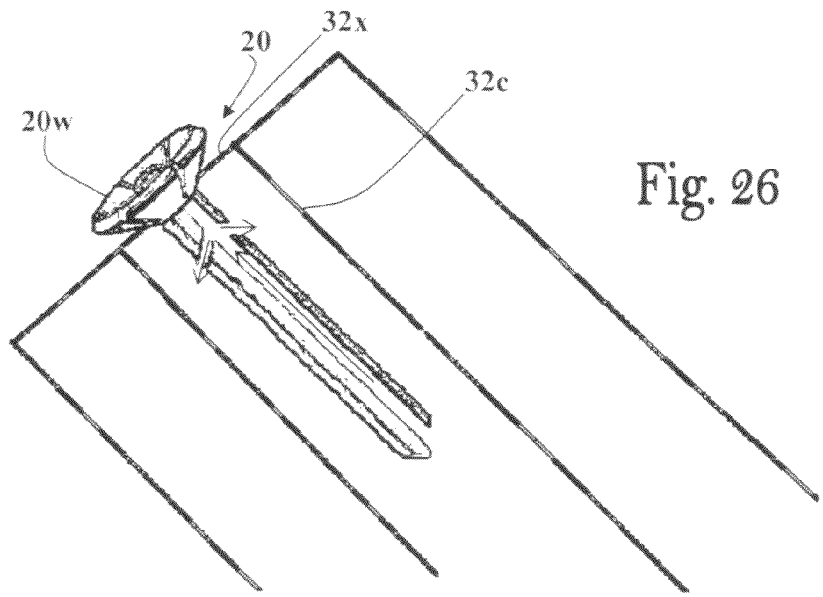
FIG. 26 schematically illustrates a possible aspiration method with the device of the invention.
Figure 27A:
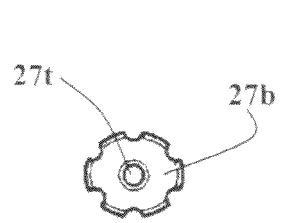
Figure 27B:
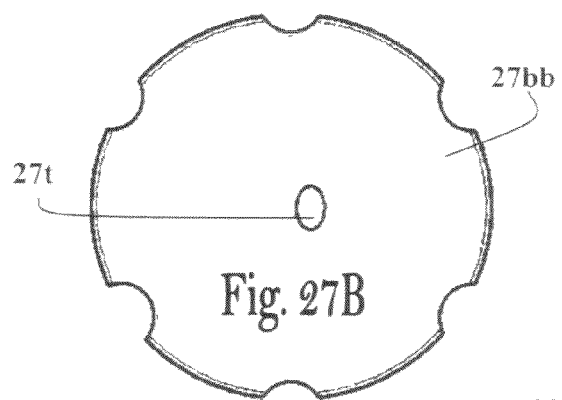
Figure 27C:
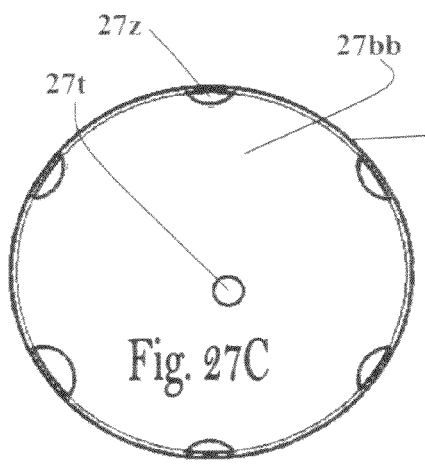
Figure 27D:
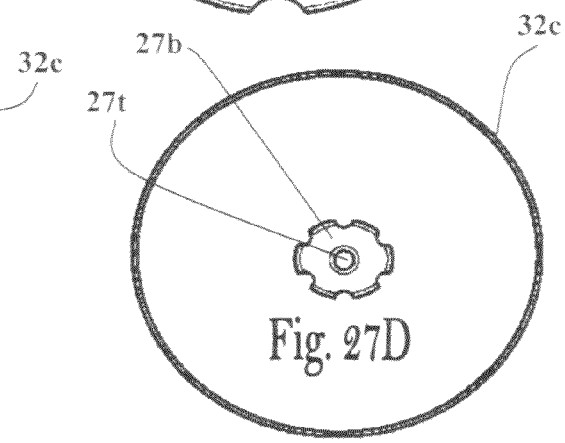

In this embodiment, as shown in FIGS. 20 to 22, the distal spray head unit 20 is constructed of a central portion 20c surrounded by series of wings 20w or petal-like elements that, when in their resting state (illustrated in FIGS. 21A and 21B), are arranged to form a generally conical or frusto-conical structure. However, when the device is inserted into the working channel, the petal-like elements are caused to adopt a closed, reduced-diameter, conformation as shown in FIGS. 20A and 20B. In order to bring the device into its second, open conformation (as defined hereinabove), the head unit 20 is further advanced distally such that it leaves the working channel through its distal exit. As shown in FIGS. 22A and 22B, the petal-like elements 20w are then further opened. This is achieved by a combination of forces that are exerted during withdrawal of the head and the resistance of the working channel exit] such that they adopt a second frusto-conical conformation that has a directionality opposite to that shown in FIGS. 21A and 21B. The head unit 20 is then moved proximally (i.e. backwards towards the operator) such that it finally comes to rest over the distal exit of the working channel 32c, as shown in FIGS. 23A and 23B. In conformation, the narrow spaces between the lateral portion of the petal-like elements 20w and the wall of the working channel distal exit, as well as the narrow spaces between each of said elements, form "virtual nozzles" (indicated by 20n in FIG. 23b). Thus, when cleaning fluid is pumped through the working channel 32c, said fluid will be caused to leave the head unit 20 through these "virtual nozzles" 20n in the form of a high-pressure spray which may be used to cleanse the portion of the colon or other body cavity that is located immediately distally to the distal exit of the working channel 32c.

As illustrated in FIGS. 22A and 22B distal head unit 20 further comprises an internal passage 20g adapted to receive a distal portion of a guidewire, or suitable tube, thereinside via proximal opening 20p. The inner passage 20g may be further employed for applying an irrigation stream via nozzle 20z provided at the distal end of distal head unit 20 by connecting a hollow guidewire or tube, to opening proximal 20p. On the proximal portion of central portion 20c there may be fixedly attached stabilizing members 20q adapted to facilitate the movement of distal head unit 20 inside the working channel.

It is to be emphasized that the "virtual nozzles" (20n) described hereinabove provide only one example of spray-forming exits that may be formed within this embodiment of the distal head unit 20, and that other nozzle or aperture forms may be incorporated therein without deviating from the scope of the present invention.

Second Spray Head Unit Embodiment

A further embodiment of the distal spray head unit 24u of the present invention is illustrated in FIGS. 24A to 24D. As shown in FIG. 24A, this embodiment comprises two concentrically arranged portions, the first of which is an inner rigid (for example plastic or metal) portion 24p that is tubular in its proximal (lower) part and is formed into a frusto-conical cap at its distal (upper) end. As seen in FIG. 24C, the spray head unit 24u is mounted on a guidewire 24r which passes through the inner lumens 24m of both the tubular and cap parts of the inner rigid portion 24p. The second portion is a flexible plug 24t containing a central lumen (through which the tubular part of the inner rigid portion 24p is inserted) and is fitted on its external aspect with an angled skirt-like element 24k. The inner portion 24p is fitted within the lumen of the outer portion 24t such that it may be caused to slide distally or proximally therein. This relation between the inner and outer portions of this embodiment is shown in the longitudinal section view provided in FIG. 24B. It will be noted from this figure that the tubular part of the inner, rigid portion 24p of the device 24u is fitted with lateral wings 24g that are sized such that they do not interfere with the distal-proximal movement of said inner portion 24p within the lumen of the outer portion 24t. In the view provided in FIG. 24B, the lateral wings 24g are situated approximately half way along the length of the lumen of the outer, flexible portion 24t of device 24u.

FIG. 24C is a longitudinal section view showing the spray head unit 24u placed within the lumen of a working channel 32c, close to the distal exit of said channel. It will be noted that as device 24u is advanced manually by the operator in a distal direction, the inner portion lateral wings 24g are caused to move distally in relation to the outer, flexible portion 24t, such that they come to rest on the inner surface of the upper (distal) face of said outer portion. It will also be seen from this figure that the angled skirt element 24k of the outer, flexible portion 24t of device 24u is compressed by the inner wall of the endoscopic working channel 32c.

As shown in FIG. 24D, device 24u may be advanced still further in a distal direction, such that it leaves working channel 32c through the distal exit thereof 32x. On leaving the channel 32c, the previously-compressed angled skirt element 24k is allowed to return to its expanded, rest position, such that upon slight proximal retraction of device 24u, said skirt element 24k acts as a mechanical stop, blocking off the distal exit 32x of working channel 32c and preventing the proximal return of device 24u back into said channel. In this first working position (also termed herein as "irrigation mode"), irrigation fluid may be pumped through working channel 32c such that it leaves said channel in the form of a high-pressure spray through the nozzles (24z, FIG. 24E) present in the upper and lateral surfaces of the rigid cap 24p. Examples of suitable nozzles 24z are shown in the transverse section view of the upper region of device 24u provided in FIG. 24E.

When the operator wishes to perform aspiration (hereinafter also referred to "aspiration mode", also illustrated in FIG. 33C) of the irrigation fluid and/or debris through the working channel he or she will simply advance the spray head unit 24u slightly in the distal direction such that the distal exit of the working channel becomes unblocked, thereby "freeing" the working channel, and permitting aspiration.

Following the irrigation and aspiration procedures, the operator can then manually withdraw the device through the working channel 32c, as shown in FIG. 24F. This stage initially requires the application of a briefly-applied force of greater magnitude than previously used in the procedure, in order to compress the skirt element 24k such that it can once more enter the working channel 32c. In this state the compressed skirt 24k blocks the passage via working channel 32c and which may advantageously be exploited for washing the working channel 32c (herein after "clearing mode") with a stream of fresh water supplied via an inner tube (32i in FIGS. 32-33) of the cleansing catheter of the invention.

Additional three-dimensional views of the above-described embodiment are shown in FIGS. 33A to 33C, wherein FIGS. 33A and 33B respectively show front and perspective views of the spray head unit 24u in the irrigation mode, wherein it is placed over exit opening 32x of working channel 32c, and FIG. 33C show a perspective view showing the state of spray head unit 24u in the aspiration mode, wherein it is advanced further distally away (e.g., about 40 mm) from exit opening 32x of working channel 32c.

In another version of this embodiment of the spray head unit; said unit comprises an external o-ring constructed of a flexible material such as silicone. The presence of this o-ring assists in providing a smooth transition between the various head unit positions when moving from one operational mode to another. The use of such an o-ring is of particular value when the device of the present invention is used in conjunction with an endoscope that has an internal taper at the distal end of the working channel. In such a case, the passage of the distal head unit through the working channel will largely be friction-free until said head unit enters the narrowed distal portion of the working channel.

Third Spray Head Unit Embodiment

In another preferred embodiment of the present invention, schematically illustrated in FIGS. 27A to 27D, the spray head unit is provided in the form of a small balloon 27b with a predefined shape, such that the outer surface of said balloon does not form a smooth unbroken arc, but rather has a furrowed, or rugose outline. This head unit is then assembled on the distal part of a small diameter tube or hollow wire 27t which serves both as a guiding wire and for inflating the balloon 27b. The balloon 27b is navigated to the distal part of the endoscope through the working channel 32c in its deflated state (27b) until it reaches the distal exit of said channel. At this point, the balloon is inflated (27bb) to partially block the flow and to form virtual nozzles 27z between the recessed outer surface of the balloon 27bb and the working channel 32c. Fluid supplied through the working channel will then leave said channel via the aforementioned virtual nozzles 27z, in the form of a high pressure jet spray.

After irrigation is completed the balloon can be deflated in order to allocate space for aspiration. The shape of the balloon may be designed such that it incorporates various special design features, such as: different wall thicknesses, different inflation shapes, etc.

The advantage of such an embodiment is that it is not required to push forward the nozzle in order to allocate the space for aspiration, and thus may simplify the user interface mechanism by using only an inflation pump with an optional pedal instead of mechanically moving a device into and out from the endoscope.

The balloon 27b for use in this embodiment may be constructed, for example, from silicone rubber or latex by means of molding and/or heat extrusion techniques and/or use of pebax, polyester, etc. . . . as are well known in the art.

To enable cleansing of the aspiration channel and/or assisting the aspiration an additional balloon may be assembled before or after the shaped nozzle balloon to seal the exit of the endoscope, thus enabling the high pressure water flushed in the distal part of the endoscope through the inner tube to flush back the irrigation liquid. This embodiment (containing an additional sealing balloon) is depicted in FIGS. 34A to 34E.

To operate both balloons a multilumen/bi-lumen tube may be used to operate independently all of the options. Thus, FIG. 34A shows this embodiment of the device with both the spray head unit balloon 34b (nozzle balloon) and the sealing balloon 34s in their deflated state. Also shown is the inflation tube 34t, the lumen of which is connected to the lumen of said balloons.

Figure 34C:
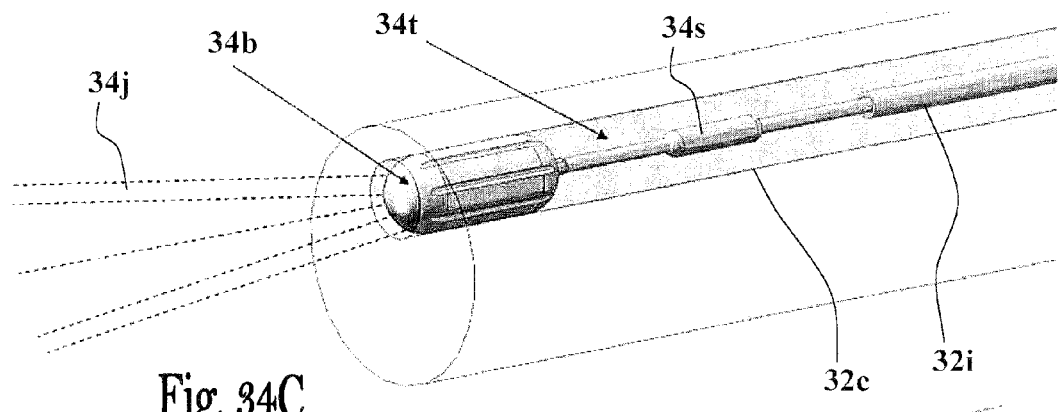

In FIG. 34B, the nozzle balloon 34b has been inflated into its working position, i.e. in the distal most portion of the working channel lumen 32c. It is to be noted that at this stage, the sealing balloon 34s is still in its deflated state. FIG. 34C illustrates the use of the device in this conformation for irrigation (illustrated as doted lines 34j) of the body passage (irrigation mode) that is situated distal to the distal end of the device.

Figure 34D:
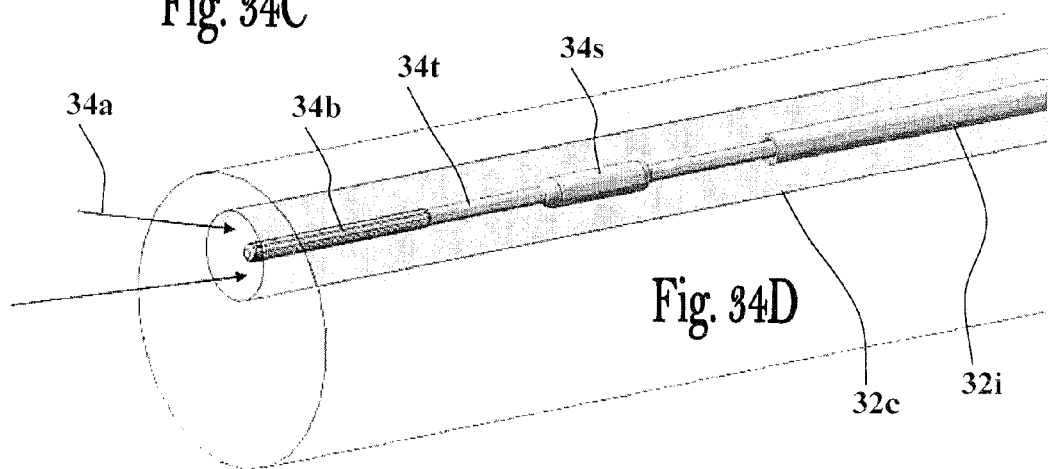
Figure 34E:
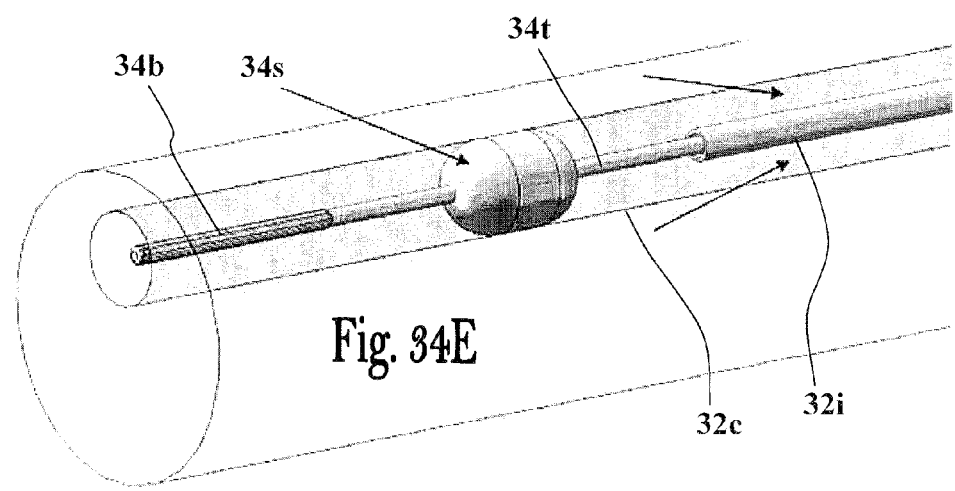

In FIG. 34D, both the nozzle balloon 34b and the sealing balloon are in their deflated states, thereby increasing the space available within the distal portion of the working channel 32c and permitting aspiration (illustrated by arrows 34a) of fluid and fecal debris therethrough (aspiration mode). In FIG. 34E, the drawing shows the sealing balloon 34s in its inflated state (with the nozzle balloon 34b deflated), and illustrates the way in which this configuration may be used to assist the aspiration of fluid and fecal debris through the working channel 32c by means of high pressure flushing in a proximal direction (clearing mode).

Fourth Spray Head Unit Embodiment

In this preferred embodiment of the present invention, shown in FIGS. 28A to 28D, the spray head unit 28u is provided in the form of a flexible mushroom-shaped valve (FIG. 28A), which is designed to increase its overall diameter upon increase in hydraulic pressure within the working channel (FIG. 28B). Thus, upon pumping irrigation fluid into the working channel (illustrated by arrows 28w in FIG. 28E) the mushroom-shaped head unit 28u expands until it causes partial obstruction of the distal exit of the working channel, the only flow that is possible being via the nozzles (28z shown in FIG. 28D) and/or "virtual nozzles" (28v shown in FIG. 28C) that are formed in said spray head unit. The mushroom-shaped valve used in this embodiment may be constructed, for example, from a flexible resin such as polyurethane or flexible silicon rubber of shore A 20-60.

Fifth Spray Head Unit Embodiment

In one preferred version of the device of the present invention, a distal spray head unit (for example, in accordance with the first or fourth embodiments described hereinabove, and which may also incorporate the mechanism enabling improved aspiration described above) may be constructed such that it incorporates biopsy forceps (or other surgical instruments) as indicated as item 29f in FIGS. 29A to 29E. This modified spray head unit permits the cleansing of the colon (or other body cavity) at specific locations immediately prior to taking a tissue biopsy. In one variant of this embodiment, the forceps opening mechanism will enable the creation of spray nozzles. Such an arrangement is particularly advantageous in endo-surgery procedures where it is necessary to replace the endoscopic tools by an irrigation nozzle and/or allocate room for aspiration. Additionally the inner tube (32i in FIG. 29D) may be assembled to enable increased aspiration force and working channel clearing together with the sealing mechanism described above.

The device described herein may be incorporated within any endosurgery device (snare, forceps, biopsy forceps, injection needle, cutter etc) where the guidewire will be replaced by the shaft of the endosurgery device and the other sub assemblies of the device (nozzle, inner tube, sealing) will be assembled as well (FIG. 29D items 28v and 32i). Item 28v describes the nozzle and the optionally sealing.

In the various embodiments described hereinabove, it is clearly necessary for the operator to control the position of distally-placed elements (such as various elements of the spray head unit, biopsy scissors etc.) from the proximal end of the endoscope. This may be achieved in various ways, by the use of various different elements including:

1. Simple handle to hold the wire and tubes to pull/push the distal head in and out of the working channel distally as well as place the nozzle on the distal part exit.
2. Control strings to hold the device in its closed state and/or open state.
3. Trigger to fix the distal part in place at one or more positions.
4. Proximal part—wire connected to a plug.
5. Torque mechanisms.

Figure 35:
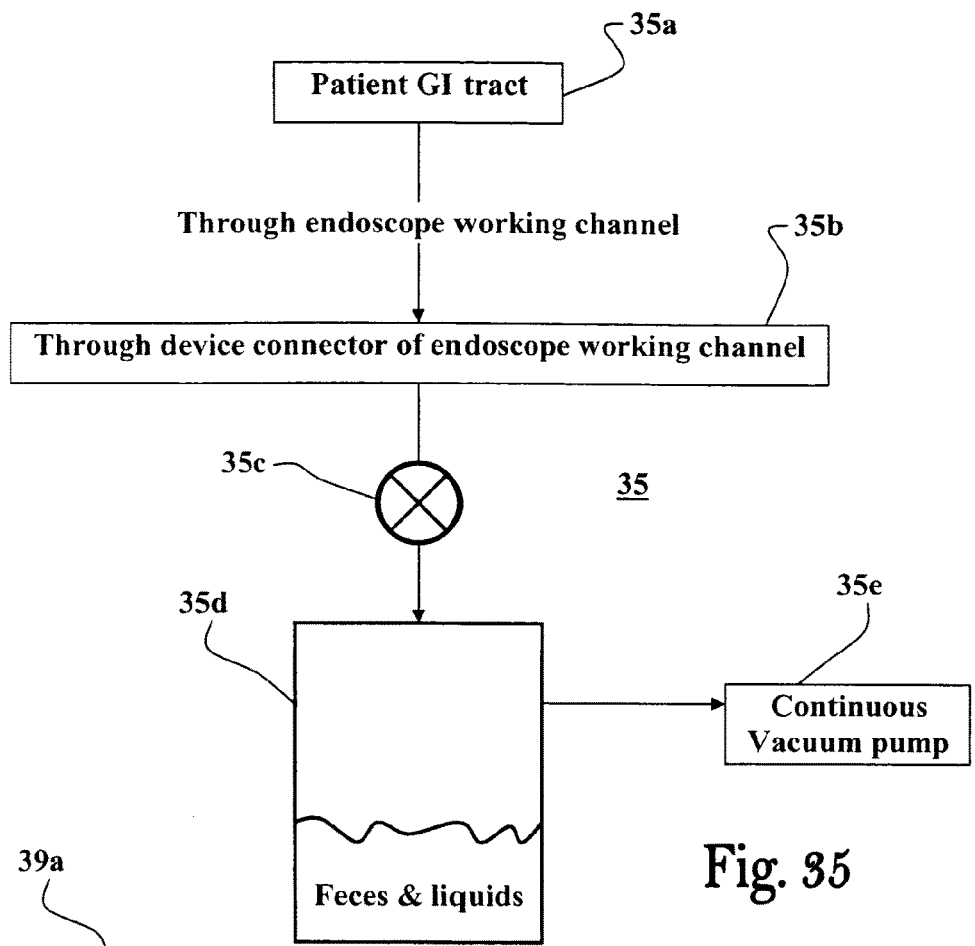
FIG. 35 is a block diagram exemplifying one possible type of aspiration system of the invention.

As explained hereinabove, one of the advantages of the device of the present invention is that it permits aspiration of solid and thick materials through the working channel of the endoscope with a reduced probability to obstruct the channel. An example of one type of aspiration system 35 is shown schematically in FIG. 35. It may be seen from this figure that this embodiment of the aspiration system 35 provides a pathway allowing the transfer of aspirated liquids and fecal material from the patient's body cavity 35a through the endoscope working channel 35b to the waste container 35d. Of particular note is the fact that system 35 does not require the use of a special pump filter. Rather, the waste container 35d functions as a pressure buffer. Thus, the vacuum applied by vacuum pump 35e is allowed to build up within the waste container 35d and connected tubing, thereby enabling the operator to perform aspiration by means of simply opening a valve 35c.

Vacuum system 35 may be operated such that the aspiration forces are repeatedly turned on and off, thereby creating rapid pressure changes enabling aggregations of solid debris to advance proximally in a step-wise manner.

As explained hereinabove, certain embodiments of the guidewire device of the present invention (notably those that comprise a partial-length tube or sleeve surrounding the guidewire for most of its length), permit enhanced clearance of particulate and liquid material from the working channel, thereby preventing blockage thereof. In this case, the method involves pulling the distal head (32a in FIG. 32C) into the working channel (32c) to a greater degree than described above (i.e. in relation to the irrigation stage), such that O-ring 32g is pulled into the working channel, thereby totally blocking the exit of the working channel. Once the exit is blocked and the working channel is partially filled with feces and other debris, a high positive pressure pulse of liquid (or air) may be directed distally through the lumen of the partial-length sleeve (32i in FIG. 32C), thereby applying positive pressure to the distal part of the working channel, and thus applying much higher forces to the solid debris than would otherwise be possible (i.e. by the use of a maximum negative 1 atm produced by the vacuum force), as illustrated in FIG. 32C.

In addition to the vacuum forces and the side jets used for irrigating the fecal debris inside the working channel (as described hereinabove), additional mechanisms may be employed in order to apply mechanic forces to the solid debris. One example of such a mechanism is shown in FIGS. 25A to 25C. This mechanism will apply a mechanical force on the feces and debris and will push the debris backwards. Such a mechanism is possible as long as the friction forces applied on the blades 25b correlate with the moment applied on the shaft 25s from the exterior without reaching plastic deformation.

Alternatively, as explained hereinabove, it is possible to use linear motion where the wire moves back and forth for a few mm or cm thus creating mechanical vibration and mechanical dismantling action helping to avoid the creation of obstruction and pushing the solid debris chunks downward (i.e. proximally).

The linear motion described above can be made more effective if some mechanical elements, such as small deflectors (30d) are mounted on the wire (32d), as exemplified in FIGS. 30A and 30B. As shown in FIG. 30A, in case a hollow wire or tube 32d is used it may further include washing apertures 30n located adjacent to deflectors 30d for washing debris during a clearing mode by streaming a washing liquid inside hollow wire or tube 32d.

Additional embodiments of the device may include washer like filters assembled on the distal part of the wire to prevent large particles of feces and/or blood clots from entering the working channel, which may otherwise potentially obstruct said channel. In some embodiments the nozzle head may also function as a built-in filter.

Sixth Spray Head Unit Embodiment

Figure 37A:
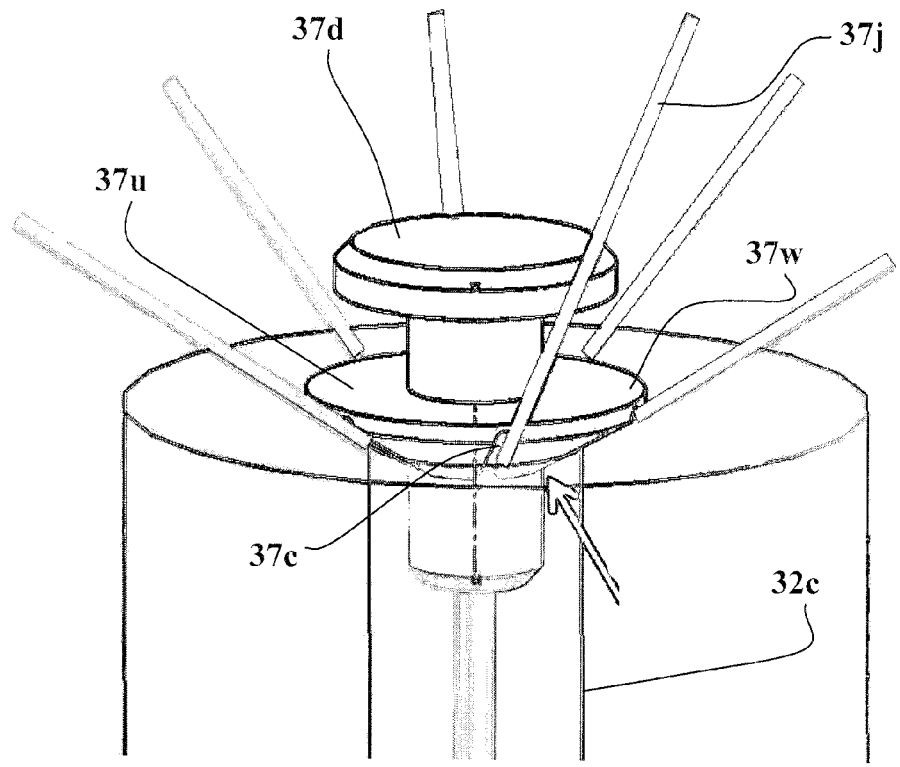
FIGS. 37A to 37C schematically illustrates an embodiment of the distal spray head of the invention which enables to control the angle of the sprayed jets, wherein FIG. 37A demonstrates adjusting the distal spray head to provide a wide-angle forward spray, FIG. 37B demonstrates adjusting the distal spray head to provide a narrow-angle forward spray, FIG. 37C demonstrates adjusting the distal spray head to provide a lateral spray.
Figure 37B:
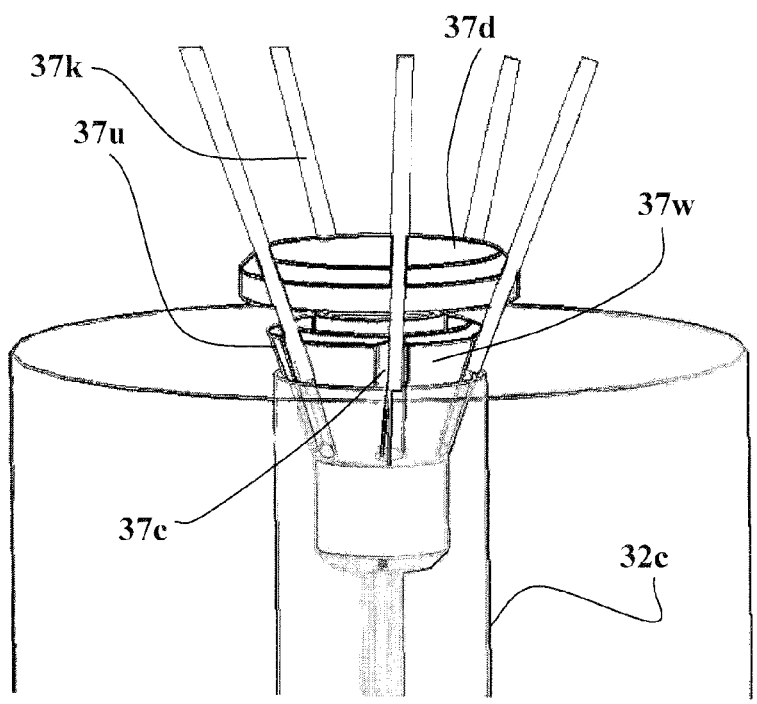
Figure 37C:
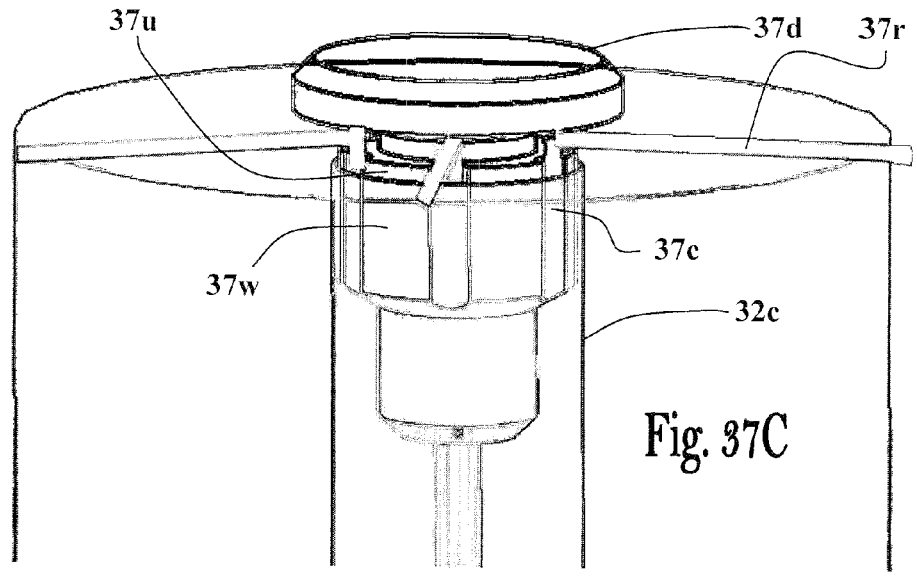

In one preferred version of the device of the present invention, depicted in FIGS. 37A to 37C, a distal spray head unit 37u is constructed such that the direction of the jet spray that leaves the nozzles may be controlled by means of pulling or pushing the distal part 37d of said unit in relation to the distal exit of the working channel 32c and thereby modifying the angle of flexible wing 37w comprising spray channels 37c. This has the effect of diverting the jet spray, such that it is possible to achieve wide-angle forward spray (37j in FIG. 37A), narrow-angle forward spray (37k in FIG. 37B) and lateral spray (37r in FIG. 37C). The latter spray direction may be usefully employed to clean the optical devices located on the distal tip of the endoscope. In order to achieve this directional effect, the distal head spray unit 37u is constructed such that it comprises a flexible wing 37w that becomes deformed upon re-entry into the working channel 32c.

Seventh Spray Head Unit Embodiment

Figure 38A:
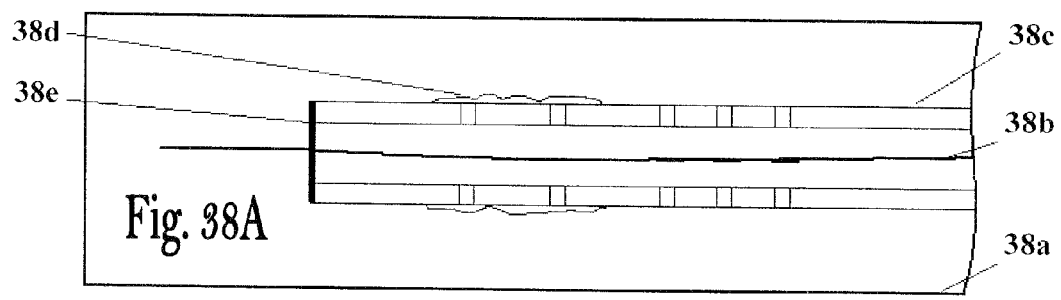
Figure 38B:
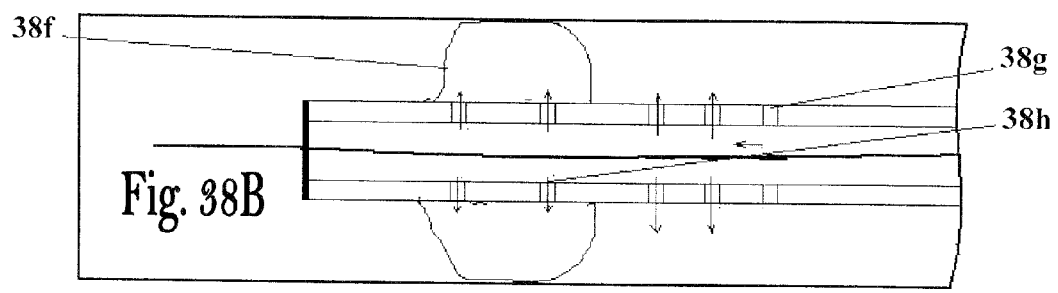
Figure 38C:
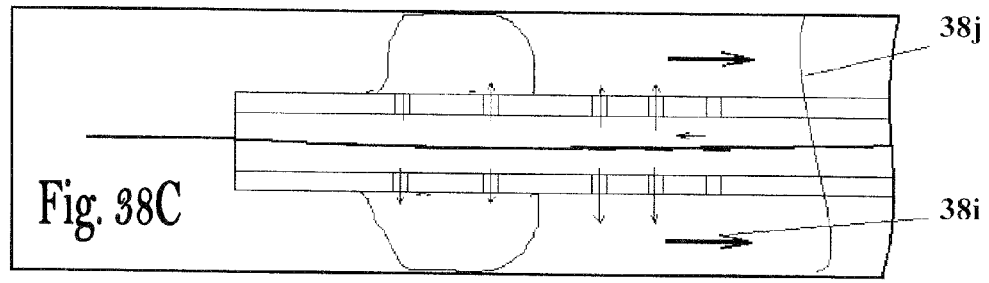

The sealing of the distal end of the endoscope working channel may be accomplished using a balloon mechanism (compliant and/or non compliant materials) using a pressure difference mechanism. This embodiment, schematically illustrated in FIGS. 38A to 38C, is characterized by the presence of two series of apertures along the distal portion of the inner tube 38c. As shown in FIG. 38B, the apertures 38h situated in the region where the inner tube 38c is overlaid with balloon 38f are larger in diameter than the second set of apertures 38g which are formed in a region of the distal tube that is not overlaid by balloon 38f. This arrangement enables balloon 38f to be inflated first and only afterwards the creation of the hydrostatic pressure that will result in jet sprays leaving the smaller apertures 38g.

This design is advantageous because it is single operating (automatic) and because no bi-lumen or additional inflation tube is required (i.e. the same conduit both inflates and irrigates backwards)

This embodiment may also be used in vascular applications where suction may collapse the arteries, or alternatively, in any case in which one requires a regulated system with a balance between the pressure in the lumen and in the balloon.

The various elements of one example of this embodiment illustrated in FIGS. 38A to 38C are as follows:
- 38a—Working channel
- 38b—Guide wire
- 38c—Inner tube (deflated)
- 38d—Sealing balloon (deflated)
- 38e—Inner tube distal end blocked
- 38f—Balloon (inflated)
- 38g—Pressure apertures
- 38h—Inflation balloon apertures
- 38i—Direction of hydrostatic positive pressure
- 38j—Hydrostatic pressure advancement Operating Handle In order to control the distal spray head-guidewire device and switch between its various modes of operation, the present invention further provides a proximal control handle, which is capable of switching between the following three modes:

1. Irrigation Mode—as described hereinabove, the nozzle (spray head unit) is located at the distal edge of the working channel creating the virtual nozzle spray. Irrigation fluid is caused to flow through the working channel in the space between the device and the channel. Control of the flow may be accomplished either semi automatically by pressing a button with predefined flow and pressure levels, or by pressing a pedal switch.

2. Aspiration Mode—the nozzle is located outside of the working channel, preferably 5-20 mm on the distal side thereof. Vacuum pressure is activated and liquid and feces remains are aspirated through the working channel while the device is still inside the body cavity that is being cleansed.

3. Working Channel Clearing ("Power Aspiration") Mode—the distal head is positioned such that it completely seals the distal exit of the endoscope working channel. In addition to the vacuum pressure, a distally-directed positive flow pressure is activated through the lumen of the partial-length tube, in order to assist in the aspiration process and prevent or clear blockage of the working channel by debris.

It may thus be appreciated from the foregoing summary of the three different operating modes that the proximal handle possesses elements that are capable of serving two key functions:

a) movement of the distal spray head between three different locations; and b) diversion of the irrigation fluid into the desired route (i.e. into the lumen of the partial-length tube during working channel clearing and directly into the working channel during irrigation).

While specifically intended for use in conjunction with the irrigation/aspiration device of the present invention, it is to be noted that the proximal control handle may also be used for other purposes during endoscopic procedures, for example the injection of ink or other marker material into the colonic lumen.

In one preferred embodiment, schematically illustrated in FIGS. 36A to 36D, the control handle 31a may be constructed such that it may be used to switch between three different positions or modes. For example, linear motion of a handle component 31h may be used to switch the device between these various modes, such that the distal head unit 31i will be fully outside the working channel 31g (i.e. distal to the distal working channel exit) in mode 2 (aspiration, shown in FIG. 36B), pulled backwards to mode 1 (irrigation, shown in FIG. 36A) and pulled further backwards to mode 3 (strong aspiration or working channel clearance, shown in FIG. 36C).

In an alternative embodiment, illustrated in FIG. 36D, a handle 31y with linear motion 31h between two mode positions and a trigger 31q to activate the third mode, may be used. In such an embodiment, the handle 31y may be moved linearly between modes 1 and 2. Mode 3 can then be activated by setting the handle in mode 2 and pressing the trigger 31q, this action causing an additional linear or rotational movement to seal the endoscope at the distal working channel exit.

The operator may recognize the position of the handle to control and switch between the modes either by: fixed linear positions, or by differentiating between the modes using different forces according to the position the distal spray head unit is located. The force feedback may be controlled by manual operator sensory feedback or by using a mechanism that is sensitive to the different forces and blocks.

Figure 40A:
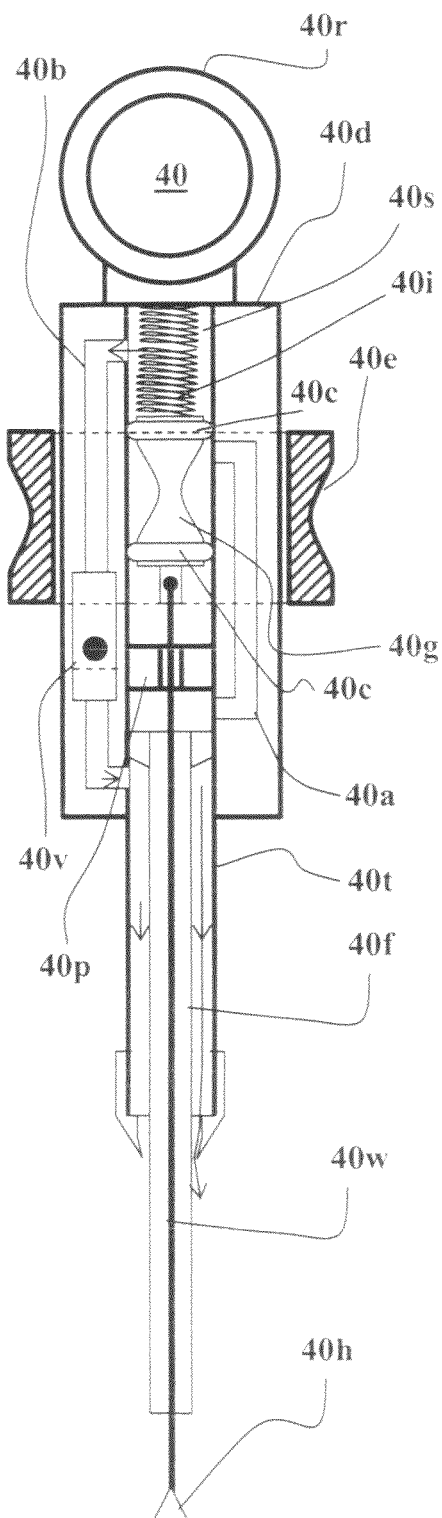
Figure 40B:
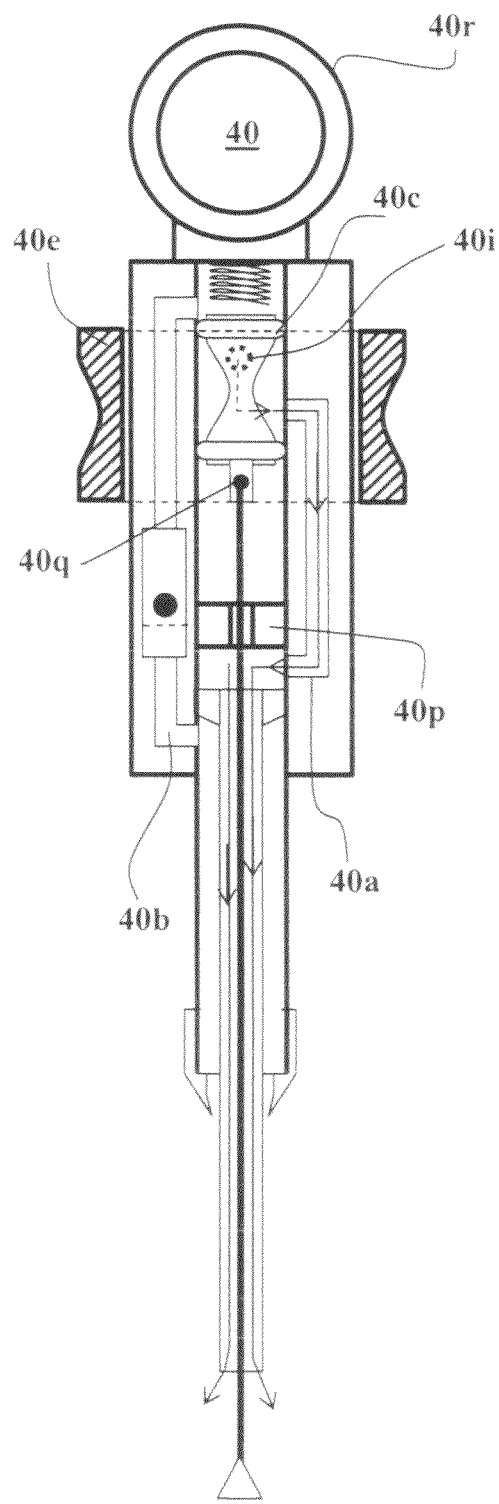

FIGS. 40A to 40B schematically illustrate one particularly preferred embodiment of a proximal control handle 40 comprising a proximal thumb ring 40r attached to a proximal housing 40d comprising a mechanism employed for changing the cleansing device of the invention between its different states of operation. An outer tube 40t, the proximal end of which is contained within proximal housing 40d, extends distally therefrom. Guidewire 40w passes distally from said proximal housing, and has distal head unit 40h mounted on its distal end. For most of its length, guidewire 40w is surrounded in a co-axial manner by partial length tube 40f which ends distally on the proximal side of head unit 40h at a distance of between 2 and 8 cm, preferably 4 cm, therefrom. In the proximal portion of outer tube 40t located within housing 40d is a slidable plunger 40g having, for example, an hourglass-like shape and comprising two seals 40c placed over each of its broad bases. The distal end of slidable plunger 40g is mechanically linked at 40q to slider element 40e placed over housing 40d, such that said slider element 40e may be used for sealably sliding plunger 40g distally or proximally inside the proximal portion of outer tube 40t.

Proximal housing 40d further comprises a spring 40s attached inside outer tube 40t to the proximal wall of housing 40d, a fluid inlet 40i, and two fluid passages 40a and 40b. The lumen of tube 40t is sealably divided into first and second sections by a sealing partition 40p through which the guidewire 40w of device 40 is sealably passed, wherein the proximal section of the outer tube comprises slidable plunger 40g and its distal section comprises a proximal portion of partial length tube 40f. The distal spray head of the invention 40h is attached at the distal end of guidewire 40w, and sidable plunger 40g is attached to the proximal end of guidewire 40w. Ideally, sealing partition 40p is provided by a dynamic seal mechanism which seals the guidewire during the channel clearing mode only (and not during normal aspiration or irrigation, wherein minimal guidewire friction is desirable and sealing at 40p is not required).

Fluid passages 40a and 40b communicate between the first and second sections of outer tube 40t, such that the inlet of fluid passage 40b is provided between fluid inlet 40i and proximal wall of housing 40d and the inlet of fluid passage 40a is located distal to fluid inlet 40i. The outlet of fluid passage 40a is provided in a portion of outer tube 40t located between sealing partition 40p and location wherein the proximal end of inner tube 40f is sealably attached to outer tube 40t.

This arrangement of proximal control handle 40 provides the mechanism required for moving the cleansing device of the invention between its different modes of operation. In the irrigation mode illustrated in FIG. 40A slider element 40e is placed distally within the proximal unit such that the proximal seal 40c of slidable planger 40g is located between fluid inlet 40i and the inlet of fluid passage 40a, thus preventing fluid flow through said fluid passage. In this state distal spray head 40h is located at the distal end of the working channel, and a stream of irrigation fluid introduced into outer tube 40t via fluid inlet 40i flows through fluid passage 40b into the lumen formed between partial length tube 40f and outer tube 40t in the proximal portion of the device, and in the space between partial length tube 40f and the working channel wall in the distal portion of the device. Finally, in the most distal portion of the device, the irrigation fluid passes through the apertures in distal head unit 40h in the form of a spray into the region of the colonic (or other body passage) lumen that is situated distal to the distal end of the colonoscope (or other endoscope).

When the operator wishes to perform aspiration of the irrigation fluid and disrupted solid debris in the colonic (or other body passage) lumen, the slider 40e is moved further distally, such that distal head unit 40h is moved beyond the distal end of the endoscope, thereby leaving the distal exit of the working channel completely open. Suction pressure is then applied in order to cause aspiration of fluid and dislodged debris into the working channel of the endoscope, and therethrough in a proximal direction, exiting the working channel of the endoscope through a one-way valve and finally being collected in an external waste container.

In the working channel clearing mode illustrated in FIG. 40B, the slider element 40e is pulled proximally until movement of the slidable plunger 40g is gradually resisted by the now-compressed spring 40s, which indicates to the operator that the device has now been placed in the clearing mode. In this mode, the proximal seal 40c is placed between fluid inlet 40i and the inlet of fluid passage 40b, thus preventing fluid flow therethrough. In this state, distal spray head 40h is pulled proximally over the exit of the working channel, into the distal portion of said channel such that said exit becomes completely blocked by the spray head. A stream of irrigation fluid is then introduced via fluid inlet 40i and fluid passage 40a into the lumen of partial length tube 40f, exiting therefrom into the distal portion of the now sealed working channel. The irrigation fluid stream introduced in this way then passes in the reverse direction (i.e. proximally) in the space between partial length tube 40f and the wall of the working channel under the dual influence of the proximal-to-distal flow through the lumen of said partial length tube and the distal-to-proximal suction pressure applied to the working channel. In this way the efficiency of the aspiration process is increased, thereby preventing the formation of blockages in the working channel and/or disrupting any such blockages that may have already formed.

Housing 40d may be manufactured from ABS, polycarbonate, Delrin and other plastic resins depending on the compatibility with the sterilization method to be used (autoclaving, Gamma radiation or ETO, preferably, by means of casting in mass production The length of housing may generally be about 80-120 mm, and the diameter of fluid passages 40a and 40b provided therein may generally be in the range of 2 mm-4 mm. Outer tube 40t may be made from ETFE, PTFE, and Nylon etc., preferably from PTFE, having a length of about 50-70 cm, depending on the endoscope length used as well as the external extension tubing length, an inner diameter generally similar to the working channel diameter in the range of 2 mm-4 mm preferably smaller to reduce hysteresis effects (around AWG8), and wall thickness of about 0.5-1 mm. Partial length tube 40f may be made from ETFE, PTFE or other plastic resins which are compatible with the applicable sterilization method with low friction coefficient and sufficient rigidity to support the device without collapsing. In an alternative flexible configuration, said partial length tube may be made of silicon or rubber resin, preferably from PTFE for low friction between the guidewire and tube as well as between the tube and the working channel, having a length of about 150 cm-210 cm, depending on the endoscope length used as well as the external extension tubing length, and having an inner diameter generally in the range of 1 mm preferably smaller to reduce hysteresis effects (around AWG16), and a wall thickness of about 0.25 mm to 0.4 mm. Guidewire 40w is preferably made from stainless steel 304V with an optional configuration of PTFE coating to reduce potential friction between the wire and the inner PTFE tube and its diameter may generally be in range of 0.5-0.7 mm, preferably about 0.6 mm.

As described hereinabove, in the channel clearing and aspiration modes the washing fluid flows proximally in the working channel. In order to prevent this stream of fluid from entering fluid passage 40b, said fluid passage preferably includes a one way valve 40v which permits flow in the distal direction only, thereby preventing washing fluid streamed inside working channel during the clearing mode from flowing therethrough in the proximal direction. It is important to include such one way flow restricting means (40v) in fluid passage 40b since the introduction of pressurized fluid into the proximal portion of the outer tube during the clearing mode could result in a rapid distal displacement of slidable plunger 40g which would cause the distal spray head 40h to move distally and out of the working channel, thereby causing an unintentional alteration in the mode of operation of the device. Examples of suitable valve devices that may be used for this purpose include ball valves and duck-bill valves.

As disclosed hereinabove, the present invention also provides further preferred embodiments of the proximal handle, including one that is particularly suitable for use in conjunction with the cleansing device that comprises both inner and outer partial length tubes surrounding the guidewire. These embodiments (which will be described in more detail hereinbelow with reference to FIGS. 42-52) are capable of enabling the cleansing device to be switched between the following three operating modes:

1. Irrigation Mode—the nozzle (spray head unit) is located at the distal edge of the working channel creating the virtual nozzle spray. Irrigation fluid (such as saline) is caused to flow through the working channel (or other instrumental or natural lumen) in the space situated between the inner tube and outer tube of the cleansing device disclosed hereinabove. Control of the flow may be accomplished either semi automatically by pressing a button with predefined flow and pressure levels, or by pressing a pedal switch.
2. Aspiration Mode—the nozzle is located outside of the working channel, preferably 5-20 mm on the distal side thereof. Vacuum pressure is activated and liquid and feces remains are aspirated through the space located between the inner and outer tubes, while the device is still inside the body cavity that is being cleansed.
3. Power Aspiration Mode—the distal head is positioned such that it completely seals the distal exit of the endoscope working channel. In addition to the vacuum pressure, a distally-directed positive flow pressure is activated through the lumen of the inner, partial-length tube, in order to assist in the aspiration process and prevent or clear blockage of the working channel by debris.

It may thus be appreciated from the foregoing summary of the three different operating modes that this second group of proximal handle embodiments possesses elements that are capable of serving two key functions:
a) movement of the distal spray head between the various locations described above; and
b) diversion of the irrigation fluid into the desired route (i.e. into the lumen of the inner partial-length tube during working channel clearing and into the space between the inner and outer tubes during regular irrigation).

Various preferred embodiments of this second group of proximal handle embodiments of the present invention will now be described, with reference to FIGS. 42-52.

Figure 42:
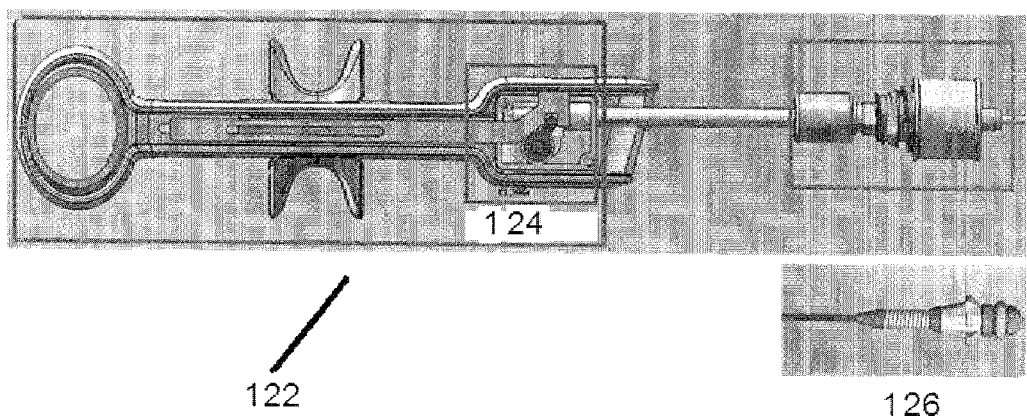
FIG. 42 provides a general view of a further preferred embodiment of the proximal handle of the present invention.

One preferred embodiment of the proximal control handle of the present invention is schematically illustrated in FIG. 42. In this embodiment, the handle comprises a main body which consists of the handle shell, as well as a slider that is used to control the axial (distal-proximal) movement of the guide wire, thereby controlling the position of the distal spray head unit. It may be seen from FIG. 42 that in addition to the externally-visible parts of the handle mechanism 122, the proximal handle also comprises, in its distal portion, a water box 124, which contains the elements required for directing the irrigation fluid flow from the pump to the distal end of the device along the relevant pathways. In particular, the mechanism housed in the water box enables routing of the irrigation fluid between irrigation and water channel clearing (power irrigation) modes As shown in the figure, the outlet of the water box is connected (by means of the guidewire) to the distal spray head 126.

Figure 43:
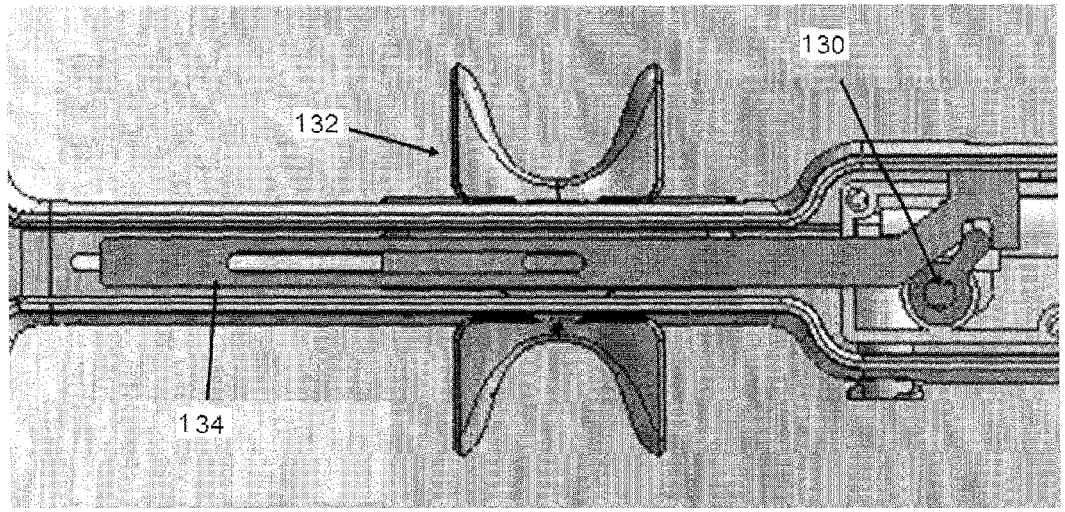
FIG. 43 provides a close-up view of valve actuator mechanism of a further preferred embodiment of the proximal handle.

FIG. 43 provides a more detailed view of the working components of the proximal handle, including the external slider 132 which is connected to an internally-located slider 134, the purpose of which is to move an actuator, which in turn causes rotation of water valve 130. In the example shown in this figure, the valve is similar to state of the art stopcock valve. The channel in which the slider moves may be notched, in order that the operator is able to receive tactile feedback concerning the position of the slider (and hence the current operating mode of the device).

Figure 44:
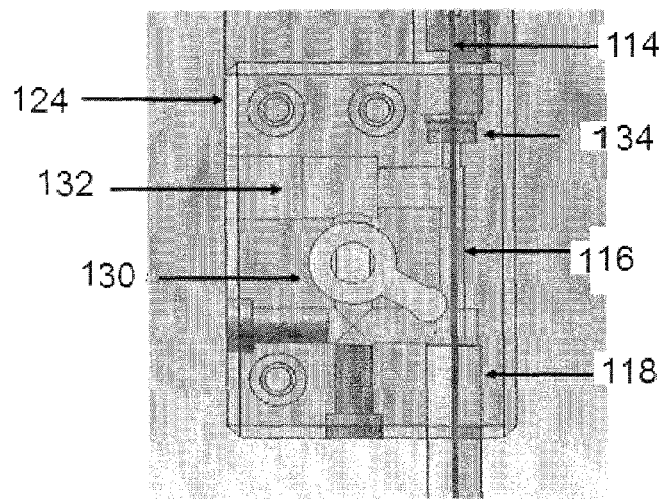
FIGS. 44-46 depict a first embodiment of a water box (manifold) of the present invention, and the way in which said water box may be used to enable a colonic cleansing device connected thereto to be switched between different operating modes.

FIG. 44 provides a detailed view of the water box 124 and of its relation to the other key components of the cleansing device of the present invention. Thus, water valve 130 is shown located close to irrigation fluid inlet 142, which receives irrigation fluid pumped from a fluid reservoir or other externally-located fluid source. This fluid input will then be directed (in accordance with the position of the water valve lever) to one or both of two fluid channel routes: the space between the inner tube 116 and the outer tube 118 and/or the lumen of said inner tube 116. Finally, this figure also illustrates the location of guidewire 114 within the lumen of inner tube 116. A guidewire sealing element 144 (e.g. an O-ring) is incorporated into the device to prevent fluid loss around the guidewire 114, while permitting the smooth axial movement of said guidewire through water box 124.

The tubing and water routing may be configured in two main modes:
1) irrigation through the inner tube lumen always open;
2) irrigation through the inner tube lumen either open or closed.

Figure 45A:
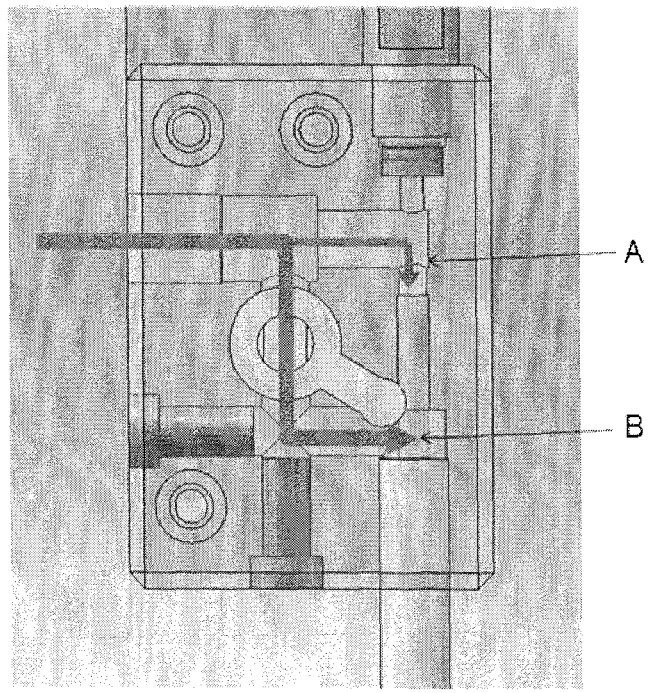
Figure 45B:
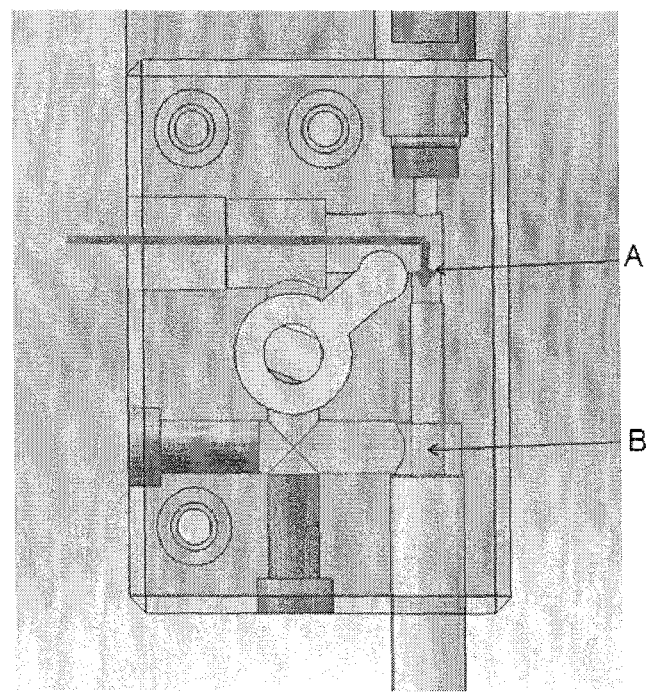

The first of these two modes ("always open mode") is illustrated in FIGS. 45A and 45B. Thus, in FIG. 45A, the water valve lever is positioned such that the irrigation fluid is caused to flow simultaneously through two channels: the lumen of the inner tube (channel A) and the space located between the inner and outer tubes (channel B). This irrigation mode is achieved by means of the operator pushing the slider forward (i.e. distally) and then retracting slightly, in order that the distal spray head comes to rest on the distal outlet of the endoscopic working channel. Simultaneously, the actuator connected to the slider will move the water valve into the desired position, whereby both channels A and B are brought into fluid communication with the irrigation fluid source. In this state, the irrigation fluid that is pumped distally through channels A and B will pass through the apertures in the distal spray head in the form of a fluid spray which may be used to cleanse the region of the body cavity (e.g. colon) that lies immediately beyond the distal end of the working channel.

The device may then be switched from the irrigation mode to the power aspiration mode (shown in FIG. 45B) by means of the operator causing further retraction (i.e. proximal movement) of the slider, such that the distal spray head is more tightly compressed against the distal working channel exit, thereby closing the distal head apertures, and thus preventing any further fluid transfer across said distal head. The corresponding movement of the actuator causes the valve to be rotated to a position in which channel B is closed, while channel A remains in the open position. In this mode, the pumped fluid passes through the lumen of the inner tube (i.e. channel A). Negative pressure is then applied to an aspiration inlet in the proximal handle that is (in this mode) in fluid contact with channel B. In this way, irrigation fluid that exits the distal end of the inner tube lumen is aspirated, proximally, through the space between the inner and outer tubes (channel B).

Figure 46:
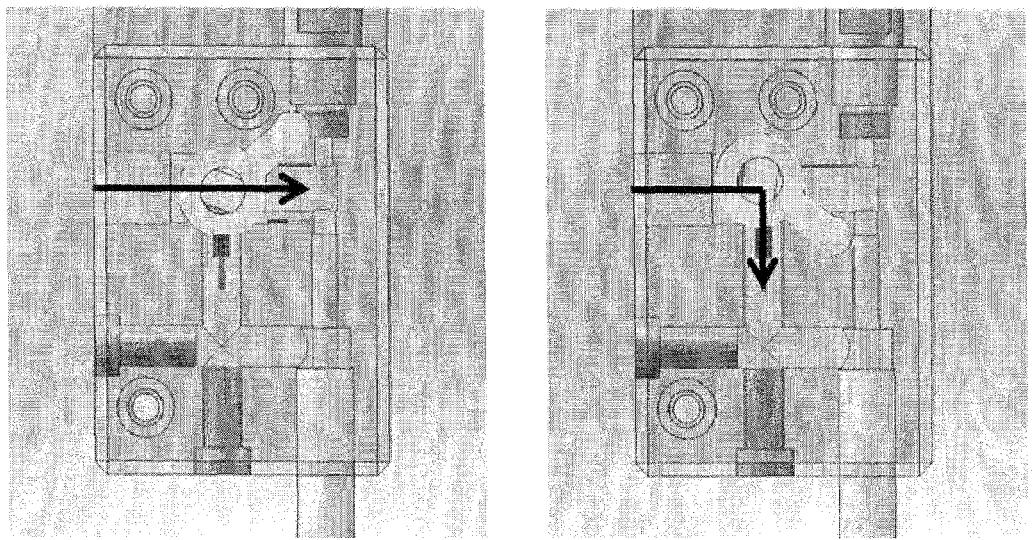

The second of the main modes mentioned hereinabove—i.e. the mode in which the inner tube lumen may be in either closed or open states (in relation to the irrigation fluid inlet) in accordance with the position of the water valve lever—is depicted in FIG. 46. The left-side panel of the figure illustrates the situation wherein channel A is open, thereby allowing irrigation fluid to pass distally through the lumen of the inner tube. In the right-side panel, however, channel A is closed and channel B is open, in which state the irrigation fluid inlet is in fluid contact only with the space between the inner and outer tubes.

Figure 47:
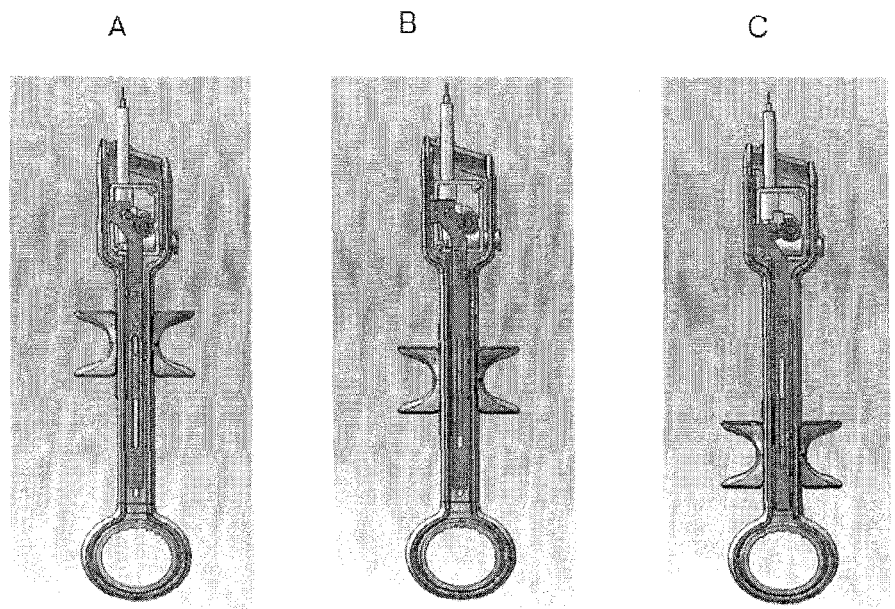
FIG. 47 illustrates the way in which the external slider is used to switch between different operating modes of a connected colonic cleansing device.

FIG. 47 illustrates the way in which manipulation of the slider by the operator is used in order to change the operating mode of the cleansing device of the present invention. Thus, in panel A, the device is in aspiration mode, in which the slider is in its forward-most position, and negative aspiration pressure is applied to the space between the inner and outer tubes. Movement of the slider into a more proximal location brings the device into irrigation mode, in which irrigation fluid is pumped distally through the space between the inner and outer tubes (and in the 'always open' mode, also through the lumen of the inner tube). Finally, further proximal movement of the slider brings the device into its power aspiration mode, in which irrigation fluid is pumped distally through the inner tube lumen against a completely sealed distal head unit, and then aspirated proximally through the space between the inner and outer tubes.

A further preferred embodiment of the proximal handle of the present invention will now be described in detail, with reference to FIGS. 48-51. This embodiment of the handle has a similar external form to the embodiment described hereinabove with reference to FIGS. 42-47, and may be used to control the operation of a connected device in a similar manner. There are, however, some important differences between the two embodiments with respect to, firstly, the valve actuator, and, secondly, the internal arrangement of the water box (also referred to herein as a manifold).

Figure 48:
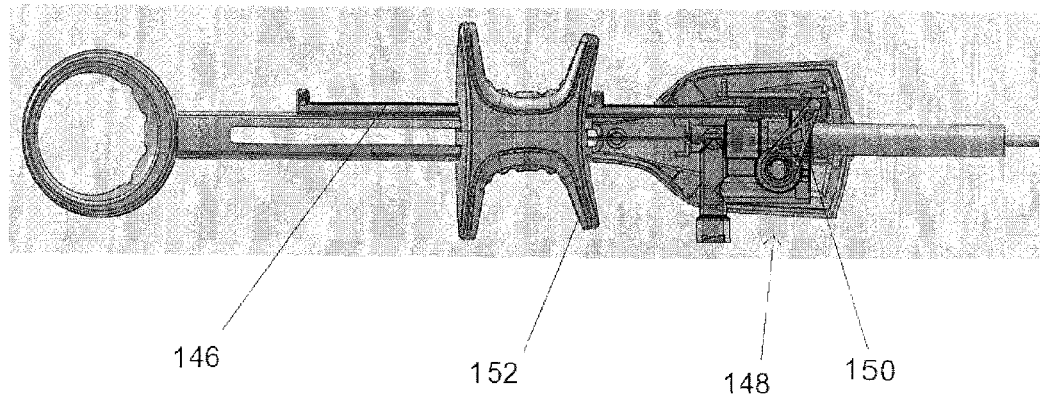
FIG. 48 illustrates a still further embodiment of the proximal handle of the present invention in which the external slider has been pushed forward distally, thereby enabling the connected cleansing device to operate in irrigation mode.
Figure 49:
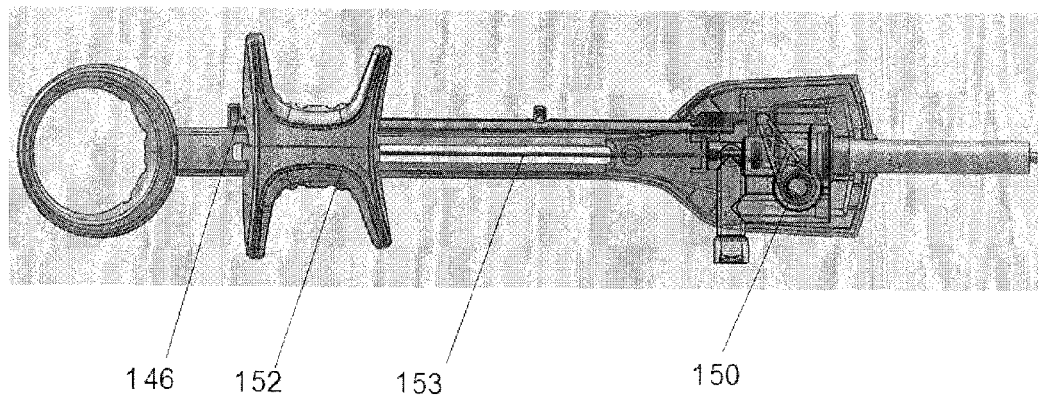
FIG. 49 illustrates the embodiment of the proximal handle shown in FIG. 48, in which the external slider has been pulled proximally, thereby enabling the connected cleansing device to operate in power aspiration mode.

FIG. 48 provides a side view of the second preferred embodiment of the proximal handle of the present invention, having a manifold 148 situated at its distal end and an external slider 152 shown in its most distal position. Also shown is the externally-placed valve actuator rod 146 (which replaces the internal slide actuator of the previously-described embodiment and represented by part number 134 in FIG. 43). This actuator rod is shown in more detail in FIG. 52, in which it may be seen that said rod is fitted with a distal stop element 166 and a proximal stop element 168, said stop elements being designed to be respectively pushed and pulled by the external slider 152. It may also be seen that the distal end of valve actuator rod 146 is fitted with a pair of jaws 170 (orientated at right angles to the actuator rod itself) which are used to grasp the movable end of valve lever 150. Thus, when external slider 152 is pushed distally, the movable end of valve lever 150 is similarly moved in a distal direction (as shown in FIG. 48). Conversely, when slider 152 is pulled by the operator in a proximal direction, the movable end of valve lever 150 is rotated in an anti-clockwise direction, and thereby moved into its proximal position, as shown in FIG. 49. It should also be noted that since the guidewire 153 of the colonic cleansing device is connected to the slider 152, movement of said slider distally or proximally will respectively cause distal advancement or proximal retreat of the distal plug that is connected to said guidewire. In this way, movement of external slider 152 is able to control two functions: the distal-proximal position of the distal plug of the connected cleansing device and the channeling of irrigation fluid through manifold 148.

As in the case of the embodiment of the proximal handle disclosed and described hereinabove with reference FIGS. 42-47, this further embodiment of the handle may be configured to operate in one or other of the following two main modes, with respect to a colonic cleansing device connected to said handle:
1) irrigation through the inner tube lumen always open;
2) irrigation through the inner tube lumen either open or closed.

Figure 50:
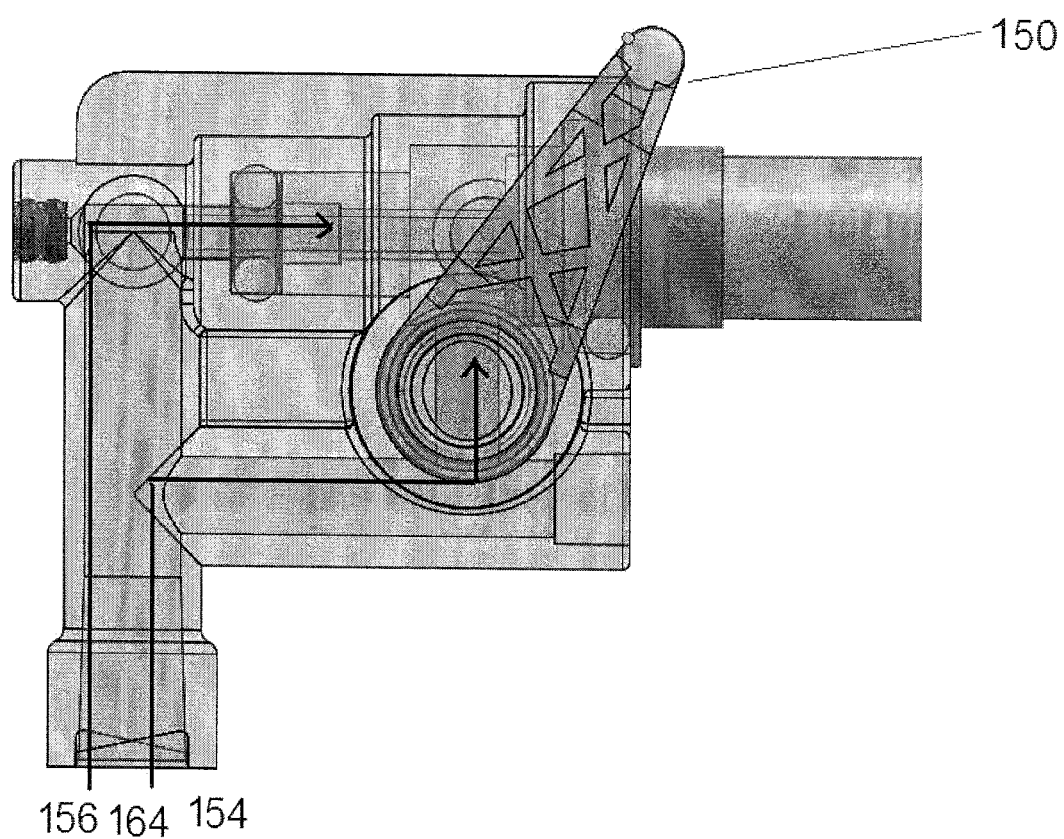
FIG. 50 provides a close-up view of the water box (manifold) of the second embodiment of the proximal handle embodiment of the proximal handle shown in FIG. 48, in a configuration which permits fluid flow into both the lumen of the inner tube of a connected colonic cleansing device and into the space between the inner and outer tubes.
Figure 51:
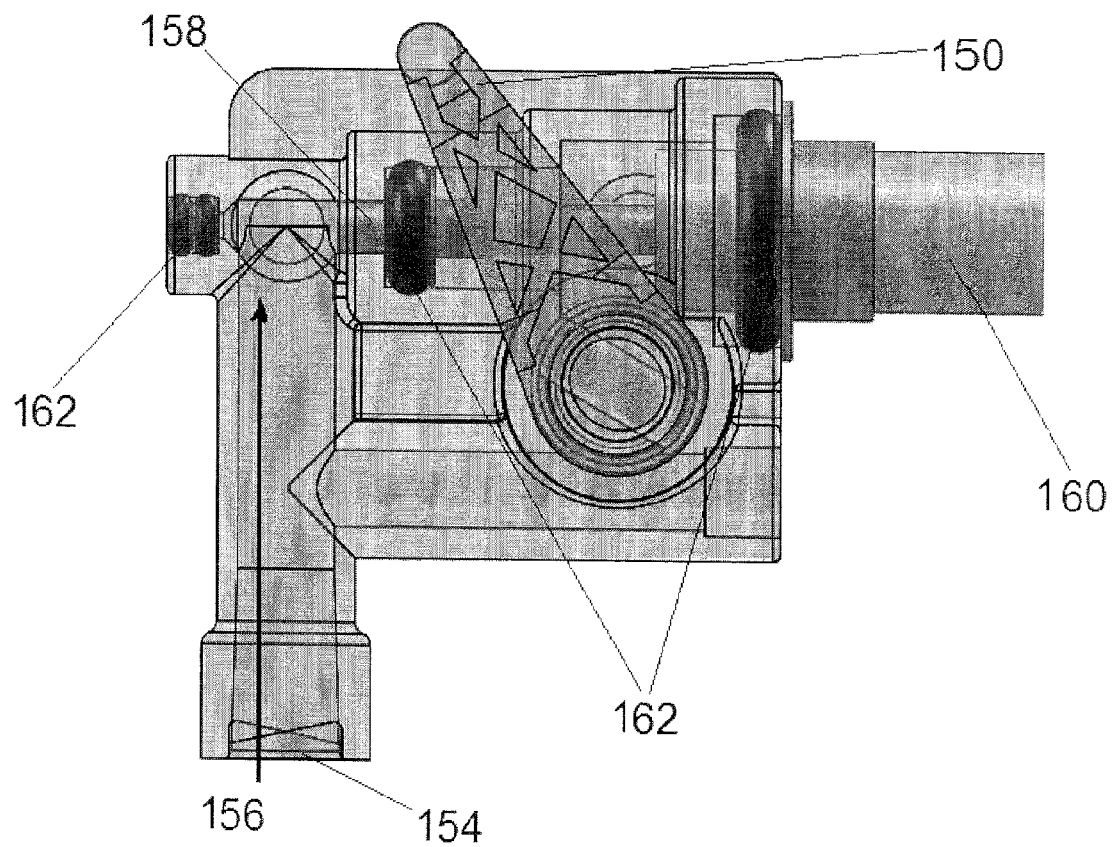
FIG. 51 provides a close-up view of the water box (manifold) in a configuration which permits fluid flow only into the lumen of the inner tube of a connected colonic cleansing device.
Figure 52:
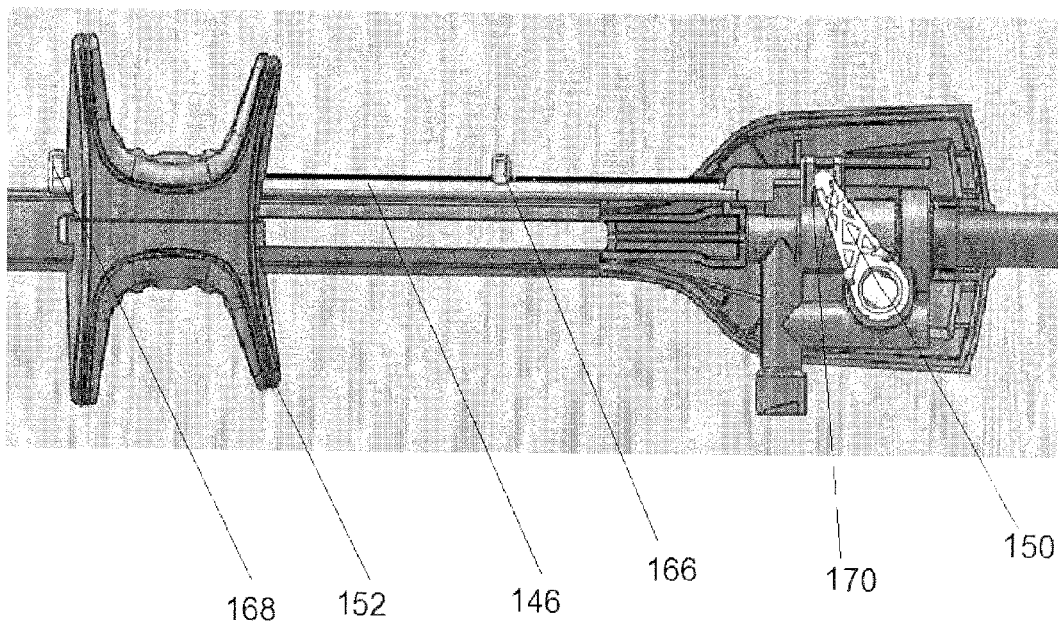
FIG. 52 illustrates the various elements employed to control the position of the manifold valve lever by means of altering the position of the external slider.

The first of these two modes ("always open mode") is illustrated in FIGS. 50 and 51. Thus, in FIG. 50, the water valve lever 150 is positioned such that the irrigation fluid (introduced via inlet 154) is caused to flow simultaneously through two channels: the lumen of the inner tube (channel A; indicated by numeral 156) and the space located between the inner and outer tubes (channel B; indicated by numeral 164). This irrigation mode is achieved by means of the operator pushing the external slider forward (i.e. distally) and then retracting slightly, in order that the distal spray head comes to rest on the distal outlet of the endoscopic working channel. Simultaneously, the actuator connected to the slider will move the water valve into the desired position, whereby both channels A and B are brought into fluid communication with the irrigation fluid inlet (via a channel formed in the pivot of the water valve lever). In this state, the irrigation fluid that is pumped distally through channels A and B will pass through the apertures in the distal spray head in the form of a fluid spray which may be used to cleanse the region of the body cavity (e.g. colon) that lies immediately beyond the distal end of the working channel.

The device may then be switched from the irrigation mode to the power aspiration mode—shown in FIG. 51—by means of the operator causing further retraction (i.e. proximal movement) of the external slider, such that the distal spray head is more tightly compressed against the distal working channel exit, thereby closing the distal head apertures, and thus preventing any further fluid transfer across said distal head. The corresponding movement of the actuator causes the valve to be rotated in an anti-clockwise direction to a position in which channel B (indicated as 164 in FIG. 50) is closed, while channel A (156) remains in the open position. In this mode, the pumped fluid that enters the manifold through fluid inlet 154 passes through the lumen of the inner tube (i.e. channel A) only. Negative pressure is then applied to an aspiration inlet in the proximal handle that is (in this mode) in fluid contact with channel B. In this way, irrigation fluid that exits the distal end of the inner tube lumen is aspirated, proximally, through the space between the inner and outer tubes (channel B). It is to be noted that that manifold used in this preferred embodiment of the proximal handle incorporates several O-rings 162 that are used to provide fluid sealing of the various components that are connected thereto, such as inner tube 158, outer tube 160 and the guidewire (not shown).

While the mode described immediately hereinabove (i.e. "inner tube always open" mode) is, for many applications, the preferred mode, it is also possible to configure the manifold such that the inner tube lumen may be in either closed or open states (with relation to the irrigation fluid inlet) in accordance with the position of the water valve lever.

It is to be noted that while the manifold (water box) of the second preferred embodiment is functionally very similar to the comparable element of the first embodiment, there are a number of differences with respect to the arrangement of the various channels within said manifold. It was found by the inventors that the channel arrangement used in the second embodiment is especially advantageous in relation to the tooling required during manufacture of the device. Thus, while several tools are required to manufacture the manifold of the first embodiment, the second embodiment requires the use of only one such tool.

It should also be noted that, as stated hereinabove, the proximal handle (in its various different embodiments) that is disclosed and described herein may be used in conjunction with several different elongate instruments that are designed for insertion into a body passage (such as the colon). Thus, in the above description of the fluid channeling within the manifold (water box) of the proximal handle, the "outer tube" is to be understood to also include within its scope other tubular structures including (but not limited to) the internal wall of a body passage (such as the colon or other part of the gastrointestinal tract), and other non-natural tubular elements such as the internal wall of an endoscopic channel (e.g. the working channel of a colonoscope).

It should be recognized that the above-described embodiments of the proximal handle constitute only one non-limiting group of possible, proximal units that may be used in conjunction with the guidewire-mounted distal spray head units of the present invention.

As mentioned hereinabove, in order to operate the colonic cleansing devices of the present invention additional items of equipment (such as a pump and a fluid tank) are required. In one embodiment, these additional items of equipment may be conveniently contained within a discrete housing. This housing is connected by suitable tubing to a water tank used for supplying the irrigation fluid to the cleansing device of the invention. In a preferred embodiment of the device of the invention may withstand irrigation pressures of up to 10 atmospheres and flow rates of about 1 liter/min. The streamed washing fluid may be controlled by the operator by means of pedal switch electrically connected to the console. The console is also connected to the working channel of a colonoscope for applying vacuum therethrough by means of a vacuum pump and aspirating debris, fecal material and other particulate matter into a waste tank.

FIG. 39 is a block diagram illustrating a preferred console implementation for the cleansing device of the invention, comprising housing 39 enclosing an irrigation pump 39$p$, (e.g. FLOJET diaphragm pump, peristaltic pump or a gear wheel pump) a vacuum pump 39$v$ (e.g. THOMAS diaphragm pump, piston pump) transformer 39$m$ (e.g., medical grade transformer Mean well/200 W Medical series), safety timer 39$t$, irrigation pump relay 39$y$ and vacuum pump relay 39$k$.

Housing 39 is connected by suitable piping to a water tank 39$a$ used for supplying the washing fluid to the cleansing device of the invention 31$k$ also being in fluid communication with the console. In a preferred embodiment of the invention irrigation pump 39$p$ is capable of providing positive pressures in the range of 2 to 10 atmospheres and flow rates of about 1 liter/min. The streamed washing fluid may be controlled by the operator by means of pedal switch 39$d$ electrically connected to the console. The console is also connected to the working channel of colonoscope 31$f$ for applying vacuum therethrough by means of vacuum pump 39$v$ and aspirating debris, fecal material and other particulate matter into waste tank 39$k$.

Additional Features of the Device and Method of the Present Invention

In a further embodiment of the present invention, the fluid spray jets produced by the distal head unit nozzles may be employed to facilitate the insertion of the endoscope into the body passage. Thus, the spray jets may assist by moving the GI tract folds and straightening the folds, thereby enabling easier pushing and pulling of the endoscope. The spray jets may also assist in endoscope insertion in some instances by means of their use to clear the GI tract lumen of large polyps, stones or other obstructions that may be located distally of the advancing distal tip of the endoscope. In addition to moving said obstructions, in some circumstances (e.g. in the case of certain stones) the fluid spray jets will also be able to cause their disintegration.

It is to be noted that although the various embodiments of the present invention have been described hereinabove as devices which may be inserted into the working channel of a colonoscope or other endoscope, all of said embodiments may equally be used in any other lumen that enables access to the body cavity (e.g. dedicated catheter).

In an alternative version of the device of the present invention, part or all of the length of the guidewire is provided in the form of a helical spring. This embodiment is advantageous in that it prevents the guidewire and attached distal head unit exerting potentially damaging forces on the colonic wall tissues, in the event that said head unit inadvertently slips laterally upon exit from the working channel during aspiration mode.

In other preferred embodiments of any of the above-described implementations of the device of the present invention, the distal head units of said device may be constructed as an integral part of a colonoscope or other endoscope, rather than as a separate, distinct instrument that is then inserted into the working channel of said endoscope.

The invention claimed is:

1. A device suitable for being passed through an internal channel of an endoscope, comprising at least one distal plug having a plurality of apertures which are capable of allowing the passage of a fluid therethrough, wherein said distal plug is connected to a distal end of an actuating element; wherein at least an outer portion of said distal plug is capable of being elastically deformed such that an external diameter thereof may be reduced in response to inwardly-directed compression forces exerted thereon from the inside of the internal channel of the endoscope as the actuating element moves inwardly in the internal channel of the endoscope closing the plurality of apertures to flow of the fluid when the apertures are in a closed conformation; and wherein said apertures are in an open conformation when said distal plug is not subject to said compression forces when the actuating element and distal plug extends out of the internal channel of the endoscope, said fluid being capable of passing through said apertures when said apertures are in said open conformation.

2. The device according to claim 1, wherein the actuating element is a wire.

3. The device according to claim 1, wherein the external diameter of the distal plug when not subjected to inwardly-directed radial compression forces is slightly larger than the internal diameter of an endoscope working channel.

4. The device according to claim 1, wherein the distal plug comprises an O-ring.

5. The device according to claim 1, further comprising a tube surrounding the actuating element in a coaxial manner,
wherein said tube extends from the proximal end of said actuating element; and
wherein the length of said tube is less than the length of said actuating element, such that a portion of the distal region of said actuating element is left unenclosed by said tube.

6. The device according to claim 5, further comprising a partial length outer tube disposed such that it surrounds an inner tube and actuating element in a coaxial manner.

7. The device according to claim 5, further comprising a proximal control handle,
wherein the proximal end of the tube is connected to said handle;
wherein the proximal end of the actuating element is movably connected to said handle;
wherein said handle comprises means for changing the distance between said handle and the distal end of said actuating element;
wherein said handle comprises one or more passages for connecting a fluid-supply channel to one of two or more fluid outlet channels; and
wherein said handle comprises means for switching between the fluid outlet channels to which said fluid-supply channel is connected.

8. The device according to claim 7, wherein the handle comprises one fluid outlet channel in fluid communication with the lumen of the tube, and a second fluid outlet channel in fluid communication with the space surrounding the external surface of said tube.

9. The device according to claim 7, wherein the means for changing the distance between the handle and the distal end of the actuating element comprises a slider.

10. The device according to claim 6, further comprising a proximal control handle, wherein the proximal ends of both the inner and outer tubes are connected to said handle;
wherein the proximal end of the actuating element is movably connected to said handle;
wherein said handle comprises means for changing the distance between said handle and the distal end of said actuating element;
wherein said handle comprises switching means for directing the output of a fluid-supply channel to one or more fluid outlet channels; and
wherein said handle comprises coupling means for coordinating the aforementioned switching between the fluid outlet channels with said means for changing the distance between said handle and the distal end of the actuating element.

11. The device according to claim 10, wherein the switching means comprises a multi-way fluid valve.

12. A system for cleansing body passages comprising:
a) a device according to claim 1;
b) an aspiration pump;
c) an irrigation pump;
d) relays, transformers and computer equipment for controlling the functioning of said device and pumps.

13. A method for cleansing a body passage comprising:
a) inserting an elongate medical device into said body passage such that the distal end thereof becomes located close to, and on the proximal side of, the area of said passage to be cleansed; b) passing a distal plug comprising a plurality of deformable, radially extending projections defining apertures therebetween through an internal channel of said elongate medical device such that said distal plug becomes located beyond a distal exit of said internal channel and in contact with the distal face of said medical device; the apertures being closed when inside the internal channel of said elongate medical device; c) introducing irrigation fluid into said internal channel at a pressure that is sufficient to cause said fluid to form a spray or jet upon passing through the apertures formed in said distal plug when said apertures are out of the internal channel of said elongate medical device; d) allowing said spray or jet to cleanse the region of the body passage that is situated immediately distal to the end of said internal channel; e) causing said distal plug to move distally such that there is no contact between said distal plug and the distal face of said elongate medical instrument within the body passage; f) applying a negative pressure to a proximal end of the internal channel of the elongate medical instrument, in order to cause aspiration of fluid and solid particulate matter through said internal channel; g) if necessary, bringing said distal plug back to the location defined in step (b) and repeating steps (c) to (f).

14. The method of claim 13, wherein the elongate medical instrument is an endoscope and wherein the internal channel is a working channel contained therein.

15. The method of claim 14, wherein the endoscope is a colonoscope and the body passage to be cleansed is a portion of the large intestine.

16. The method according to claim 13, wherein the distal plug is attached to a guidewire.

17. The method according to claim 16, wherein the guidewire is surrounded by a partial length inner tube that extends distally from the proximal end of said guidewire, and wherein the length of said tube is less than the length of said wire, such that a portion of the distal region of said wire is left unenclosed by said tube.

18. The method according to claim 17, wherein the partial length inner tube is surrounded coaxially by a partial length outer tube.

19. The method according to claim 17, further comprising the steps of: i) withdrawing the distal plug into the distal end of the internal channel such that said distal plug is radially compressed, thereby causing its external diameter to be reduced, thereby sealing the distal end of said internal channel; ii) introducing irrigation fluid into the lumen of the partial length tube such that when said fluid leaves the distal end of said tube, the positive fluid pressure provided thereby assists in preventing or removing blockages in the distal portion of the internal channel of the elongate medical device.

20. A method for cleansing a body passage comprising:
   a) inserting an elongate medical device into said body passage such that the distal end thereof becomes located close to, and on the proximal side of, the area of said passage to be cleansed;
   b) passing a device comprising a distal head spray unit comprising a plurality of deformable, radially extending projections defining a plurality of apertures therebetween through an internal channel of said elongate medical device, wherein said distal head spray unit is connected to a distal end of a collapsible catheter and to a distal end of an associated stiffening wire, such that said distal spray head unit becomes located beyond a distal exit of said internal channel; the plurality of apertures being closed when inside of said internal channel of the elongate medical device;
   c) introducing irrigation fluid into the lumen of said collapsible catheter at a pressure that is sufficient to cause said fluid to form a spray or jet upon passing through the apertures formed in said distal spray head unit when said apertures are out of the internal channel of the elongate medical device;
   d) allowing said spray or jet to cleanse the region of the body passage in which said distal spray head unit is located;
   e) closing a supply of irrigation fluid to the lumen of said collapsible catheter, and optionally applying a negative pressure to a proximal opening of said lumen, such that the walls of said catheter collapse thereby decreasing the volume of the internal channel occupied by said catheter;
   f) applying a negative pressure to a proximal end of the internal channel of the elongate medical instrument, in order to cause aspiration of fluid and solid particulate matter through said internal channel;
   g) if necessary, repeating steps (c) to (f).

21. The device according to claim 1, wherein said distal end of said distal plug comprises a plurality of deformable, radially extending projections that define said apertures therebetween such that said apertures are each spaced apart from one another.

22. The device according to claim 21, wherein said distal end of said distal plug comprises a rigid portion defining a distally-facing dome and said distal end of said distal plug comprises a deformable, angled skirt-like element, said skirt-like element being connected to said dome by a cylindrical element.

23. The device according to claim 22, wherein said cylindrical element has a maximum width that is less than that of said skirt-like element and said dome.

24. The device according to claim 22, wherein said skirt-like element has a convex portion that faces a common direction with a convex portion of said dome.

25. The device according to claim 23, wherein said apertures extend through said convex portion of said skirt-like element.

26. The device according to claim 22, wherein said skirt-like element that has a first convex portion that faces a common direction with a convex portion of said dome and a second convex portion that faces opposite the common direction.

27. The device according to claim 26, wherein said apertures extend through said first convex portion.

28. The device according to claim 22, wherein said apertures are configured to spray said fluid radially outward from said cylindrical element as said fluid passes through said apertures.

29. The device according to claim 22, wherein an O-ring is fitted on said cylindrical element.

30. A device suitable for being passed through an internal channel of an endoscope, comprising:
   at least one plug having a proximal end and a distal end, said proximal end of said plug being connected to a wire of an actuating element, said distal end of said plug comprising a plurality of deformable, radially extending projections that define apertures therebetween, said apertures being spaced apart from one another,
   wherein at least an outer portion of said plug is capable of being elastically deformed such that an external diameter of said plug may be reduced in response to inwardly-directed compression forces exerted thereon, said apertures being in a closed conformation when said distal plug is subject to said compression forces when said apertures is inside the internal channel of the endoscope, and in an open conformation when said plug is not subject to said compression forces when said aperture is out of the internal channel of the endoscope.

31. The device according to claim 30, wherein said distal end of said plug comprises a rigid portion defining a distally-facing dome and said distal end of said plug comprises a deformable, angled skirt-like element, said skirt-like element being connected to said dome by a cylindrical element.

* * * * *